(12) United States Patent
Tsekos et al.

(10) Patent No.: US 9,539,058 B2
(45) Date of Patent: Jan. 10, 2017

(54) ROBOTIC DEVICE AND SYSTEMS FOR IMAGE-GUIDED AND ROBOT-ASSISTED SURGERY

(71) Applicant: University of Houston System, Houston, TX (US)

(72) Inventors: Nikolaos V. Tsekos, Houston, TX (US); Nicholas C. von Sternberg, Spring, TX (US)

(*) Notice: Subject to any disclaimer, the term of this patent is extended or adjusted under 35 U.S.C. 154(b) by 383 days.

(21) Appl. No.: 14/010,155

(22) Filed: Aug. 26, 2013

(65) Prior Publication Data

US 2014/0058406 A1 Feb. 27, 2014

Related U.S. Application Data

(60) Provisional application No. 61/692,943, filed on Aug. 24, 2012.

(51) Int. Cl.
*B25J 3/00* (2006.01)
*A61B 19/00* (2006.01)

(52) U.S. Cl.
CPC ........... *A61B 19/2203* (2013.01); *A61B 34/30* (2016.02); *A61B 90/39* (2016.02);
(Continued)

(58) Field of Classification Search
CPC ............... B25J 3/04; B25J 3/00; B25J 9/1689; A61B 19/2203; A61B 2019/2223; A61B 2019/262; A61B 2019/5227; A61B 2019/5229; A61B 2019/5297; A61B 2090/374; A61B 2090/378; A61B 90/39
See application file for complete search history.

(56) References Cited

U.S. PATENT DOCUMENTS 6,167,292 A * 12/2000 Badano ................. A61B 19/54
600/407
2007/0156122 A1* 7/2007 Cooper .............. A61B 19/2203
606/1

(Continued)

FOREIGN PATENT DOCUMENTS

EP 2263591 A2 * 12/2010
FR 2657730 A1 8/1991
WO 2011057260 A2 5/2011

OTHER PUBLICATIONS

Ming Li, Dumitru Mazilu, Ankur Kapoor and Keith A. Horvath, MRI Compatible Robot Systems for Medical Intervention, Advances in Robot Manipulators. Edited by Ernest Hall Publisher InTech Published Apr. 1, 2010 p. 443-458.

(Continued)

*Primary Examiner* — Elmer Chao
(74) *Attorney, Agent, or Firm* — Eric P. Mirabel

(57) ABSTRACT

Provided herein are robotic systems, for example, MRI guided robots, for image-guided robot-assisted surgical procedures and methods for using the same to perform such surgical procedures on a patient. The robotic systems comprise a robotic manipulator device or global positioner, means for actuating the robotic manipulator or global positioner that is mechanically linked thereto and a computer having a memory, a processor and at least one network connection in electronic communication with the robotic system. The actuating means comprises at least one transmission line having a flexible component comprising a displaceable medium, a rigid component comprising rigid pistons or a combination through which actuation is transmitted to the robotic manipulator or global positioner. The computer tangibly stores in memory software modules comprising processor-executable instructions to provide inter- (Continued)

faces between the robotic system, an imaging system and an operator and to control operation thereof.

27 Claims, 53 Drawing Sheets

(52) U.S. Cl.
CPC ... *A61B 2034/306* (2016.02); *A61B 2090/374* (2016.02); *A61B 2090/378* (2016.02); *Y10S 901/02* (2013.01)

(56) References Cited

U.S. PATENT DOCUMENTS

| | | |
|---|---|---|
| 2008/0004632 A1 | 1/2008 | Sutherland et al. |
| 2008/0287963 A1* | 11/2008 | Rogers ............... A61B 1/00039 606/130 |
| 2009/0112082 A1 | 4/2009 | Piferi et al. |
| 2011/0077504 A1 | 3/2011 | Fischer et al. |

OTHER PUBLICATIONS

European Search report.
Translation of FR 2657730 A1.

\* cited by examiner

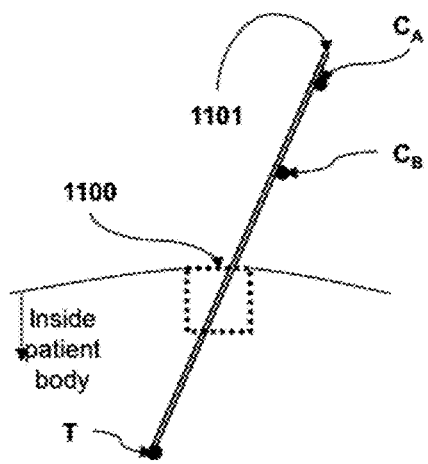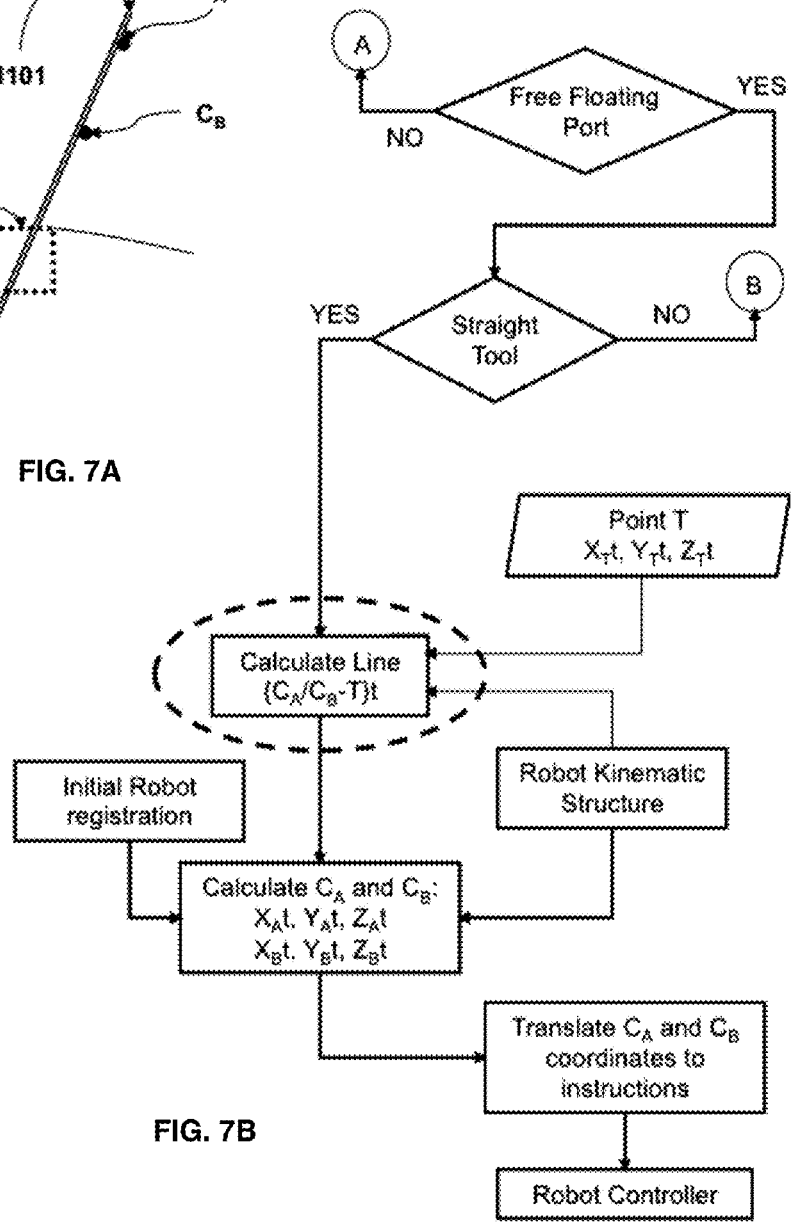
FIG. 7A
FIG. 7B

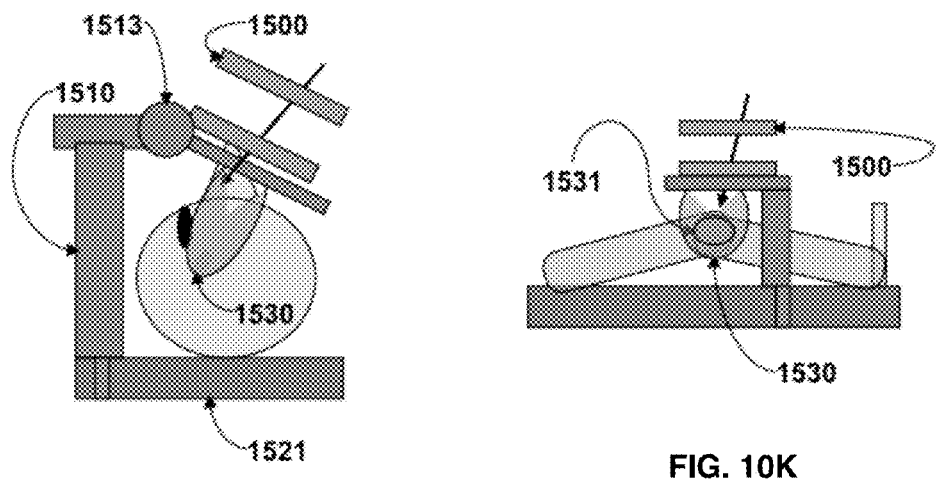
FIG. 10J
FIG. 10K
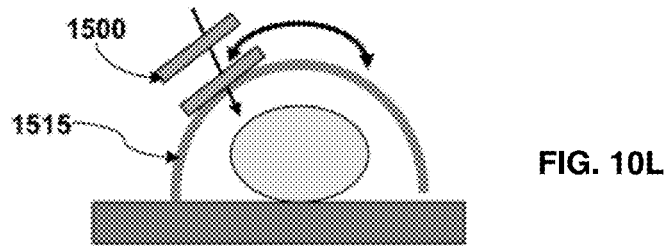
FIG. 10L
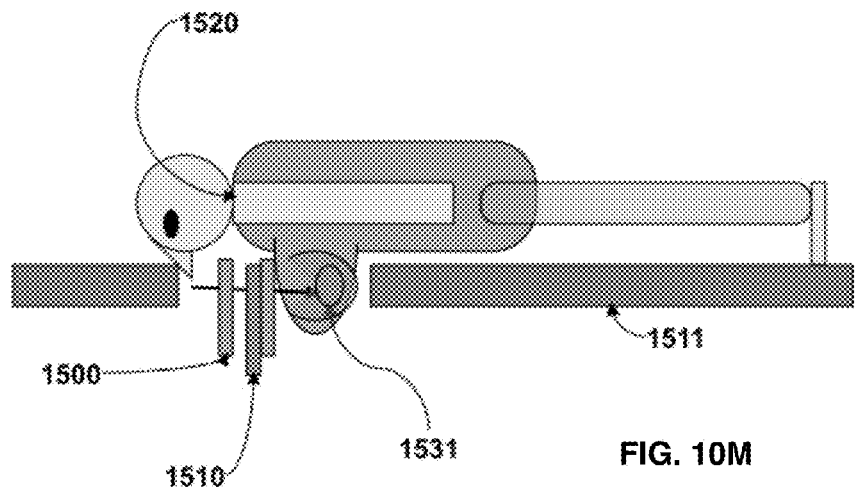
FIG. 10M

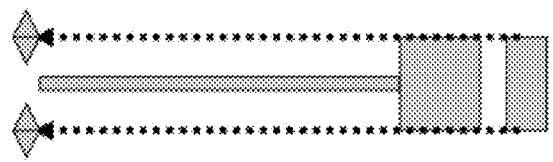
FIG. 14D
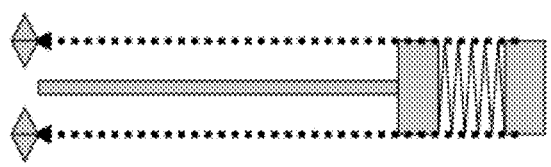
FIG. 14E
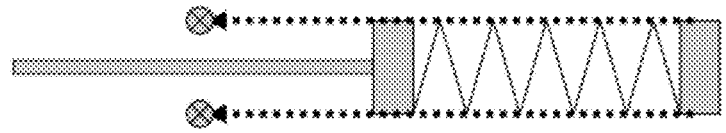
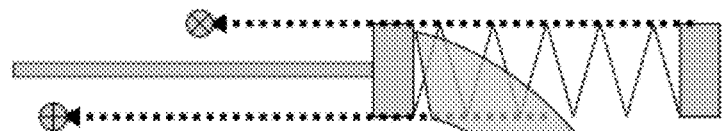
FIG. 14F
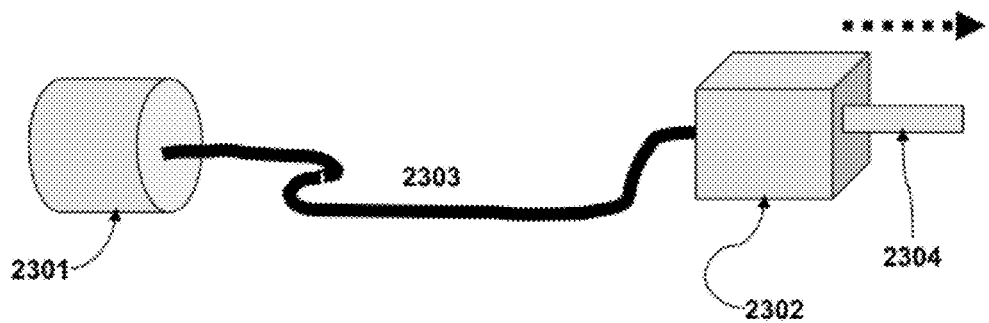
FIG. 15

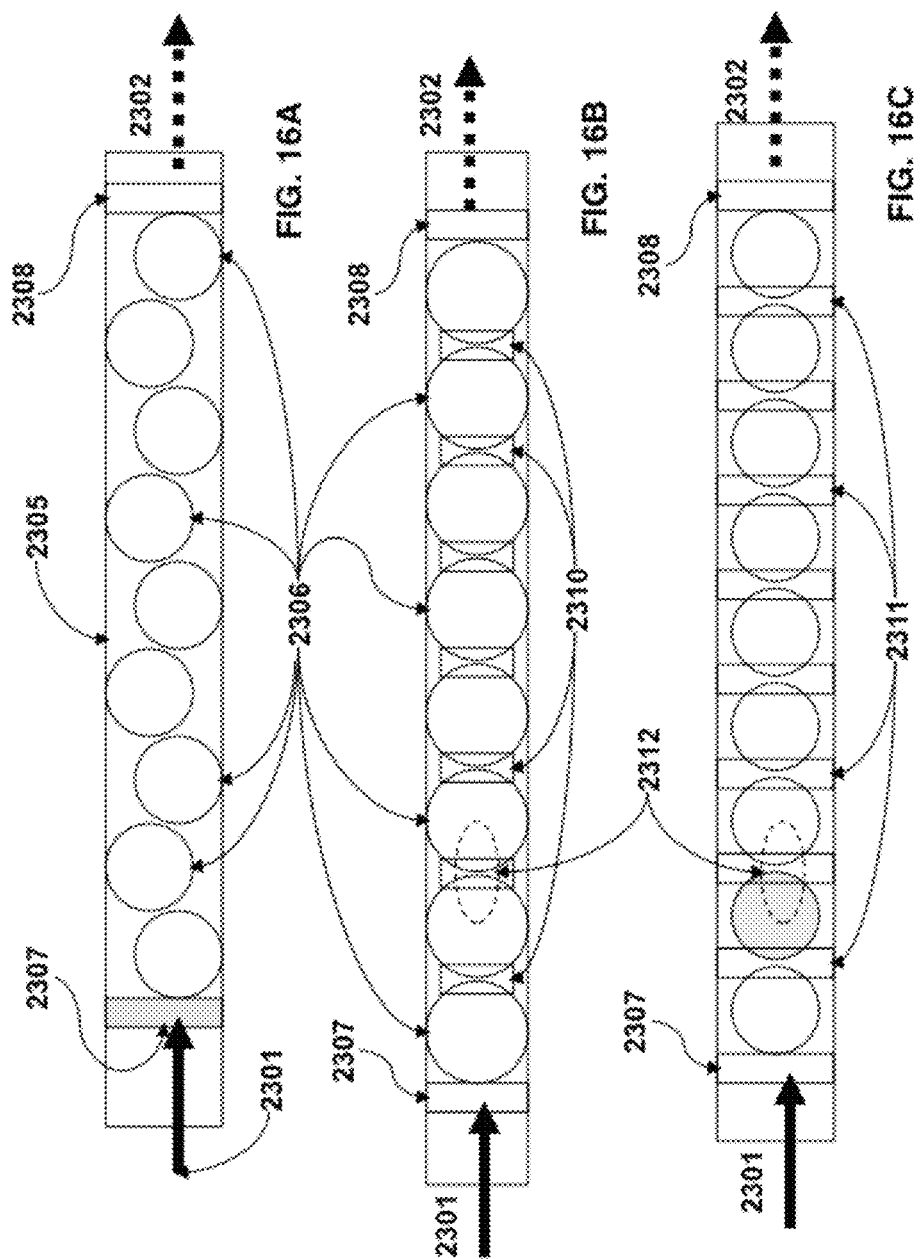

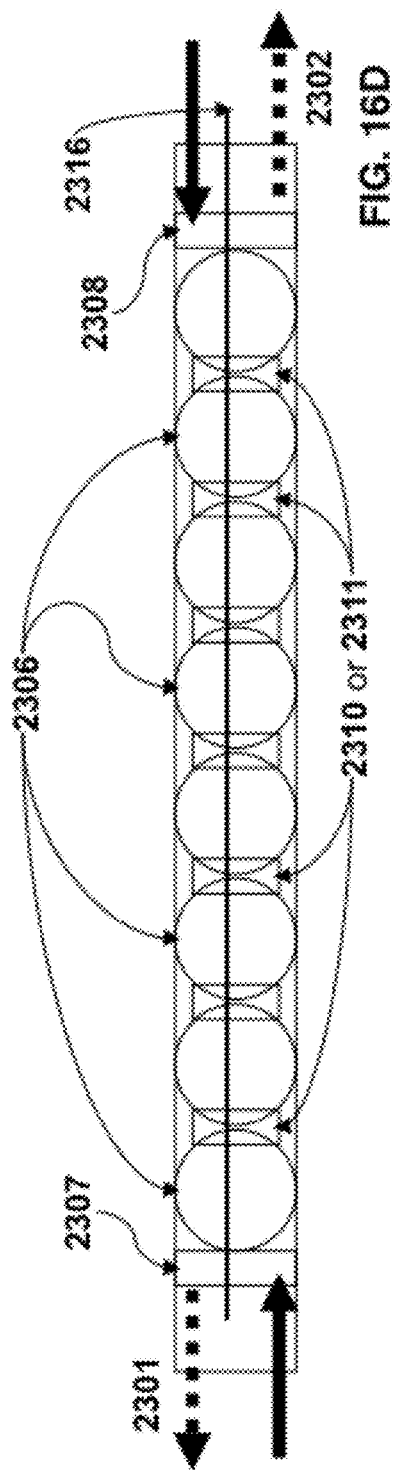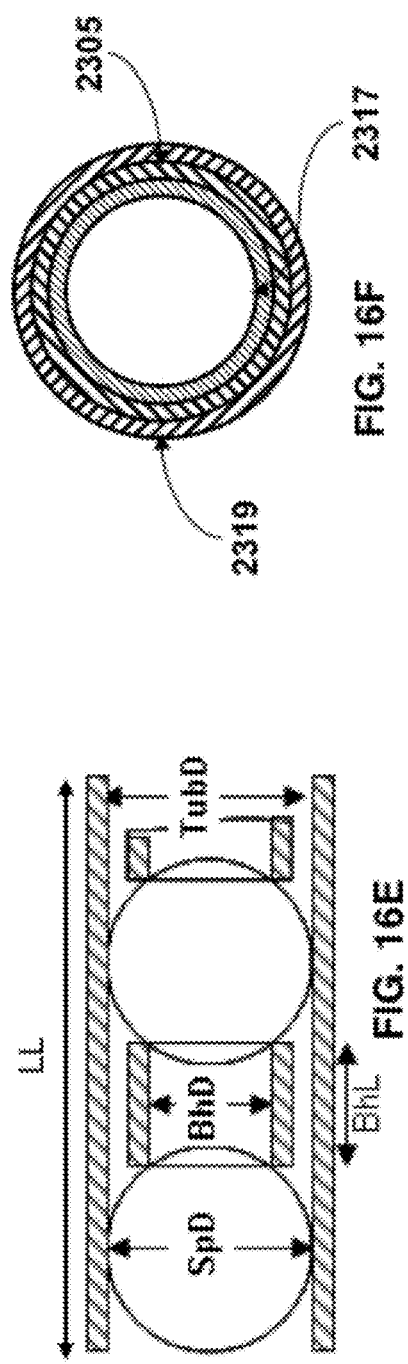

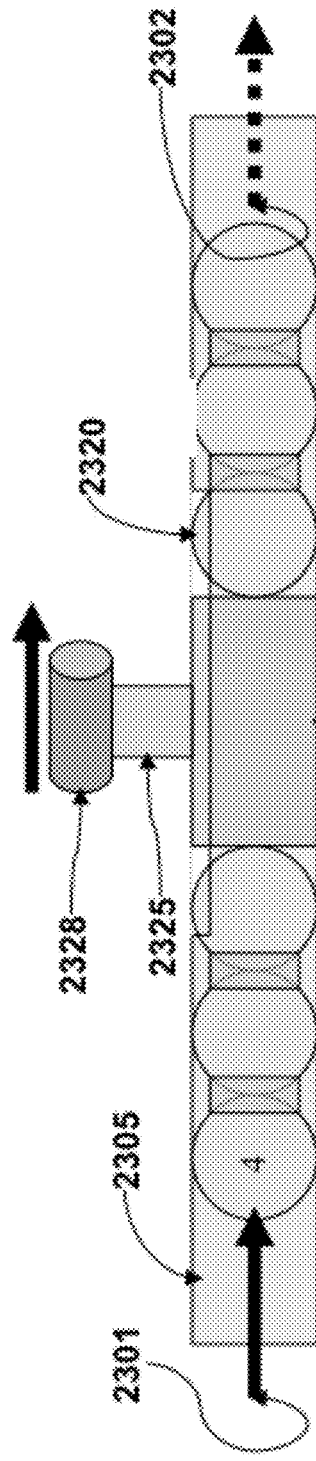
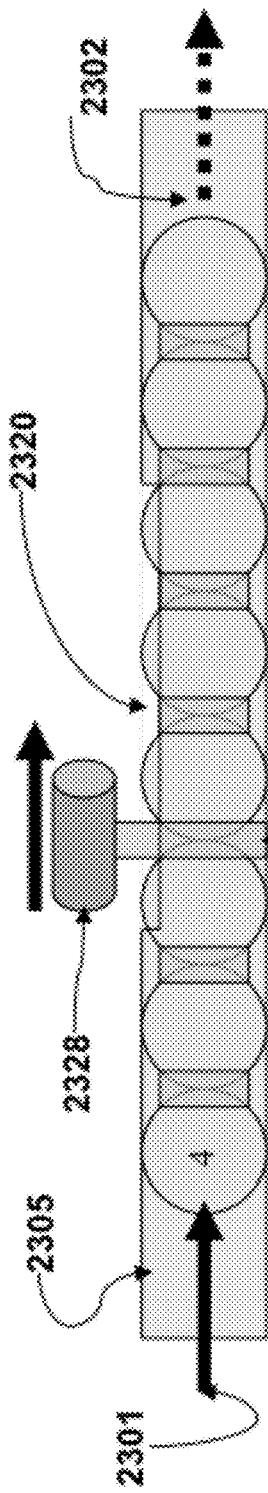
FIG. 17D
FIG. 17E

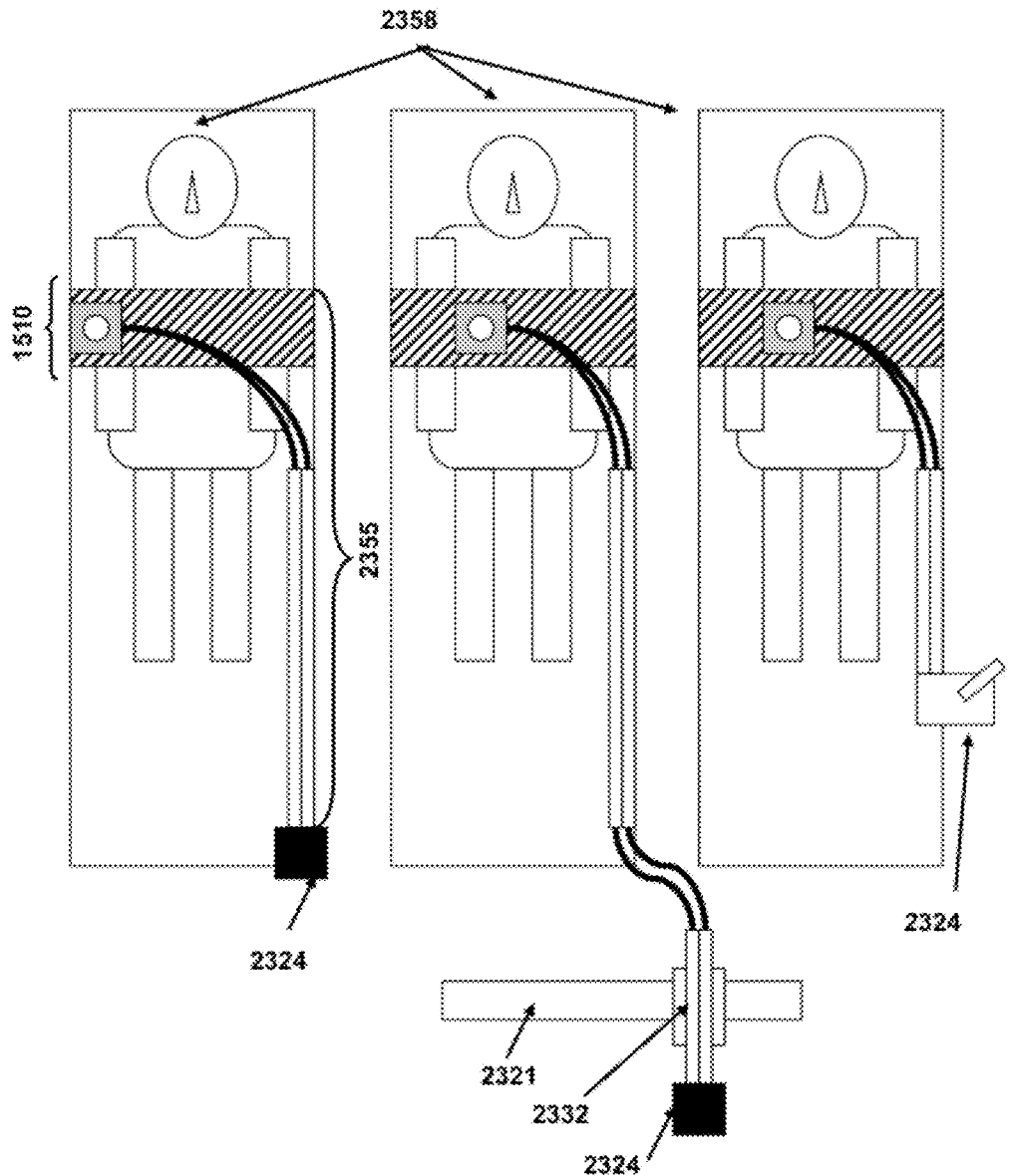

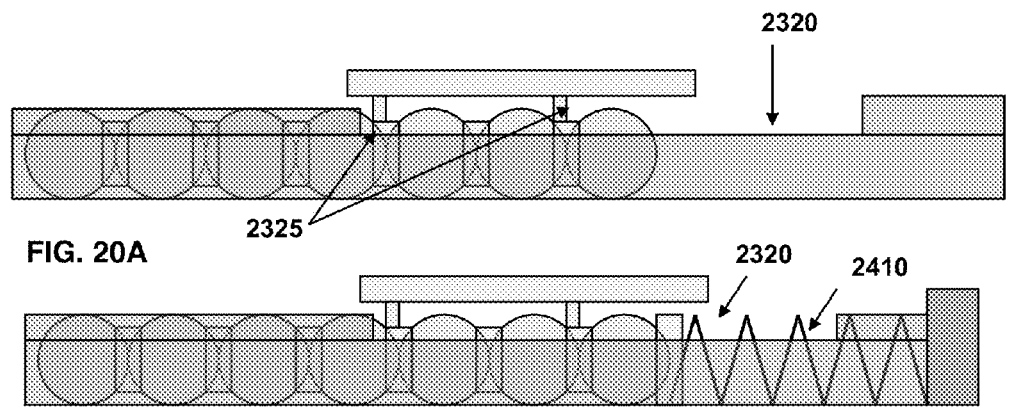
FIG. 20A
FIG. 20B
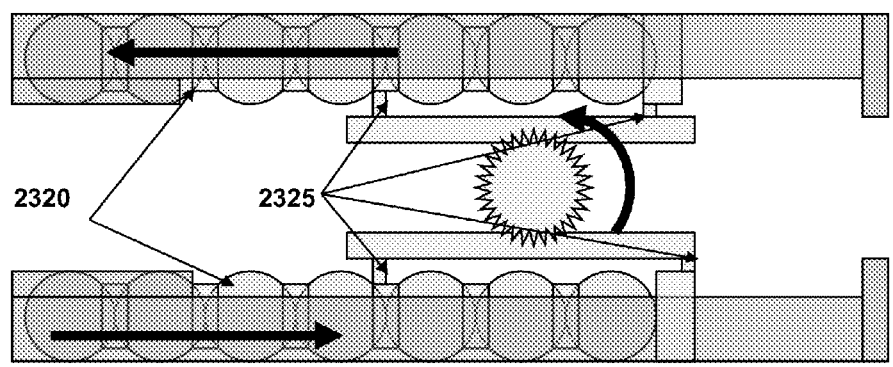
FIG. 20C
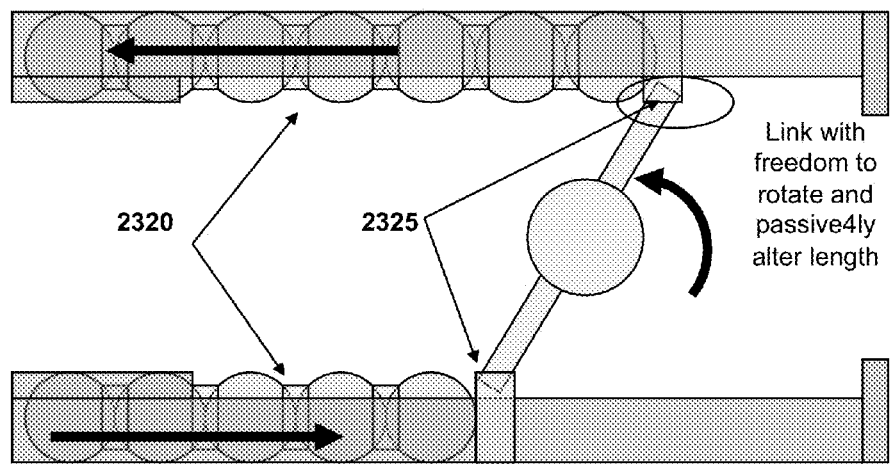
FIG. 20D

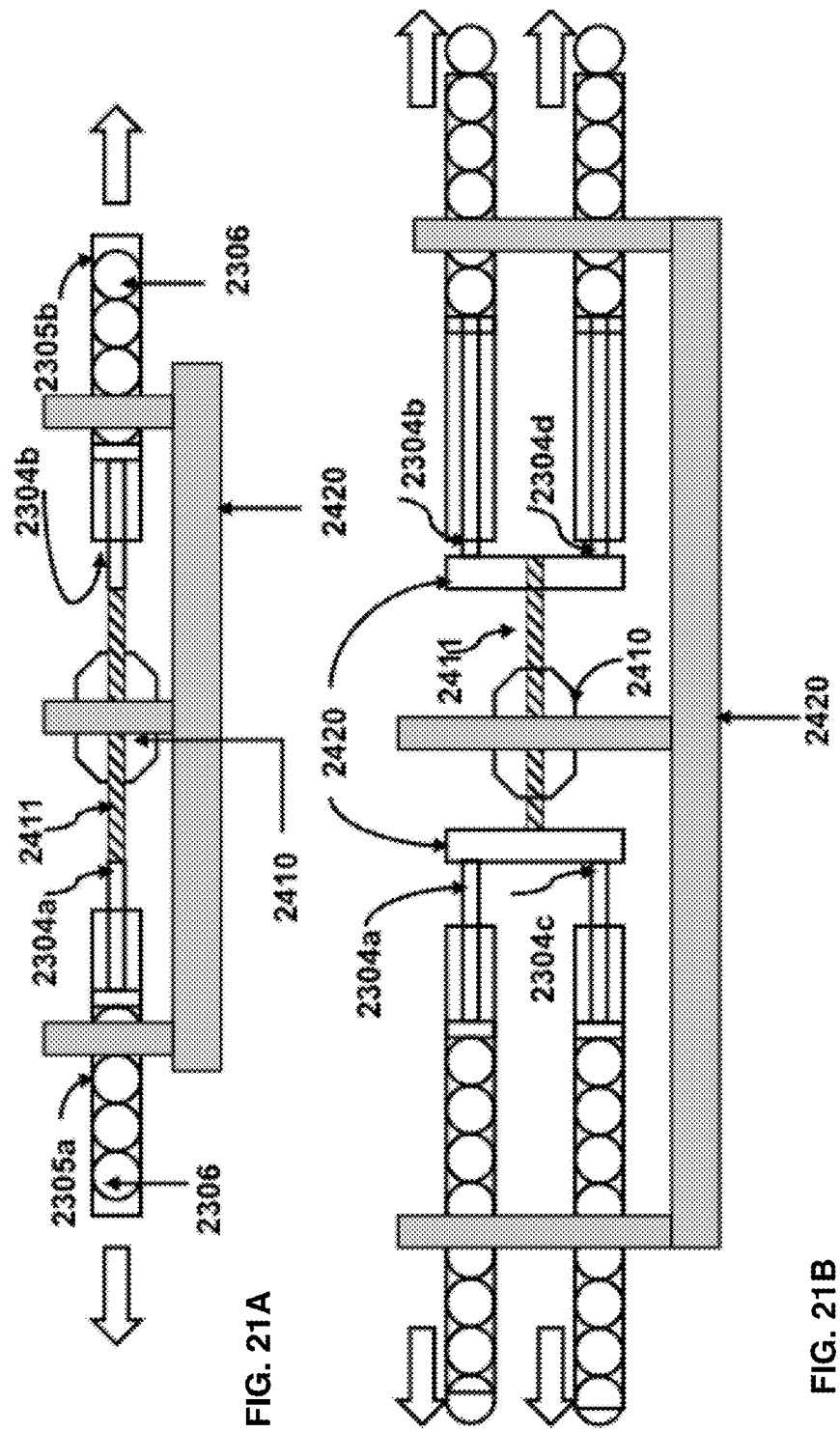

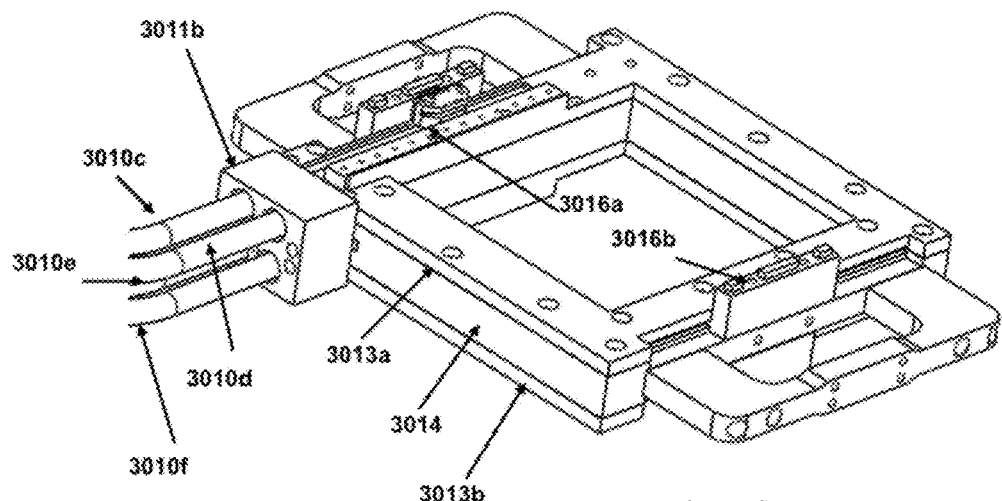
FIG. 23G
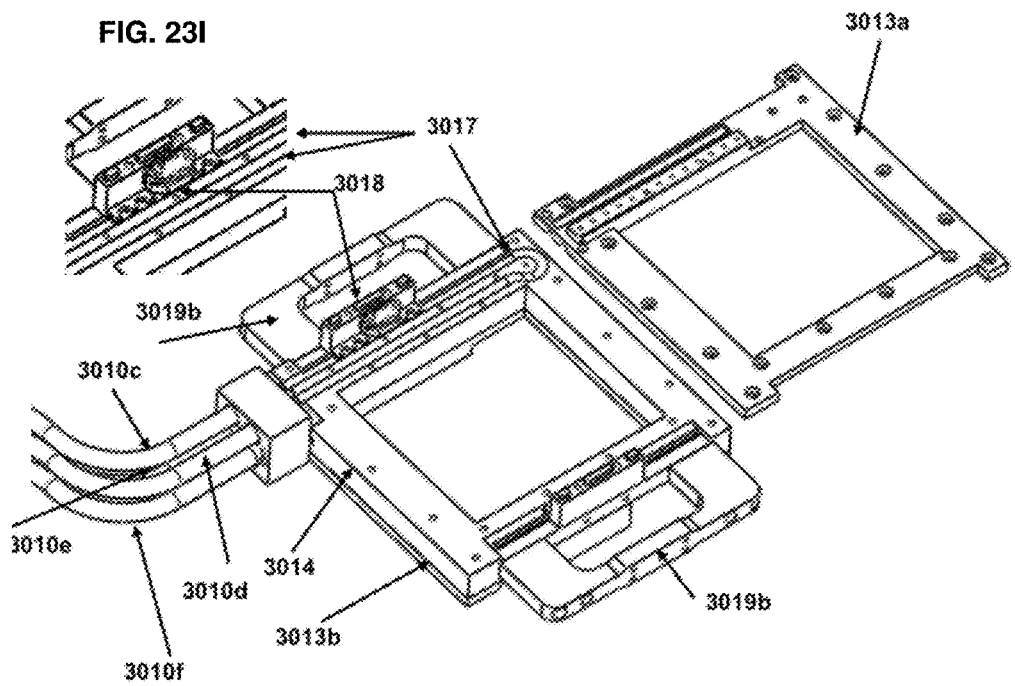
FIG. 23I
FIG. 23H

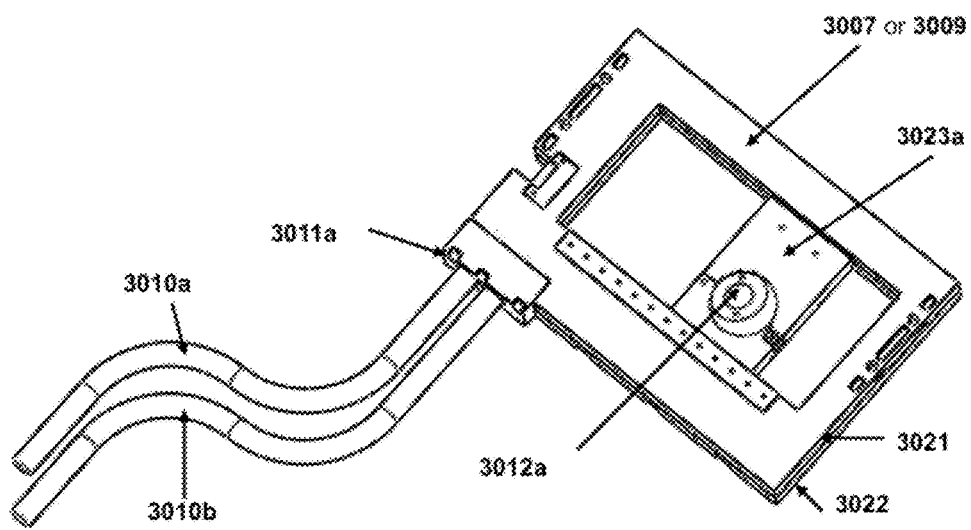
FIG. 23J
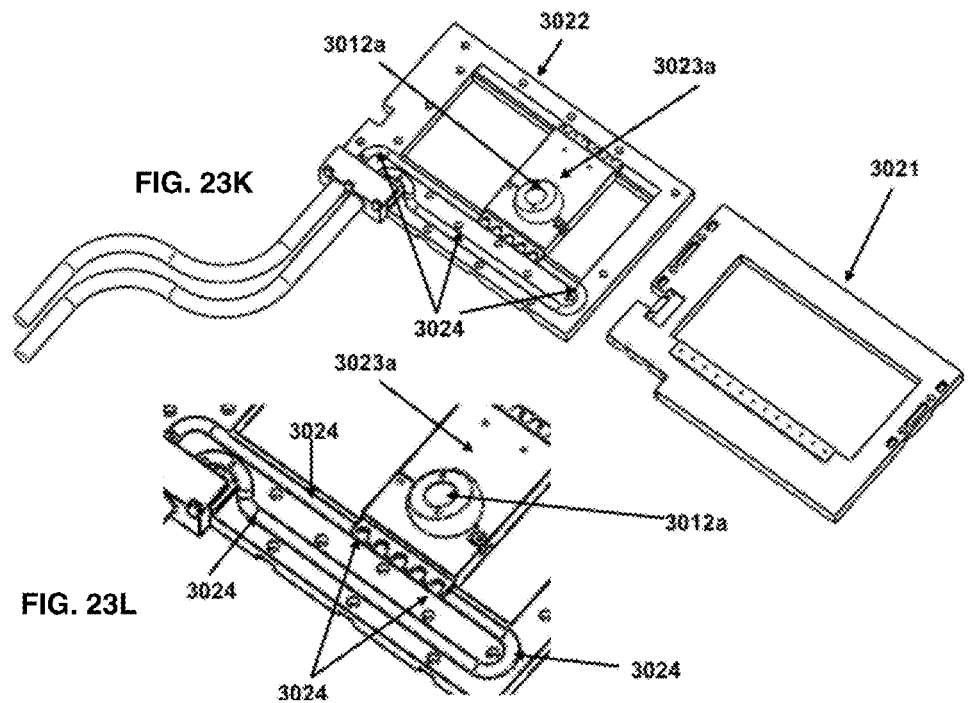
FIG. 23K
FIG. 23L

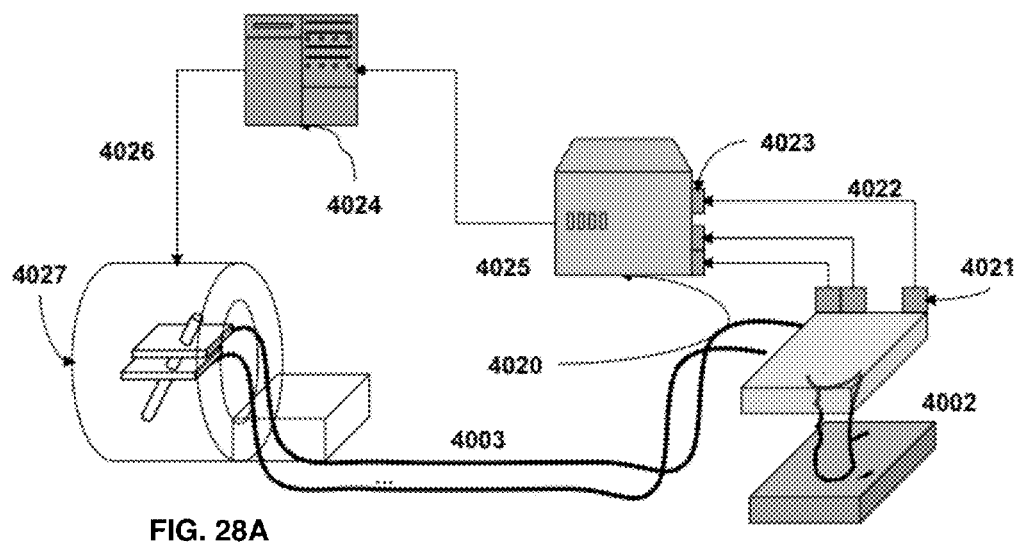
FIG. 28A
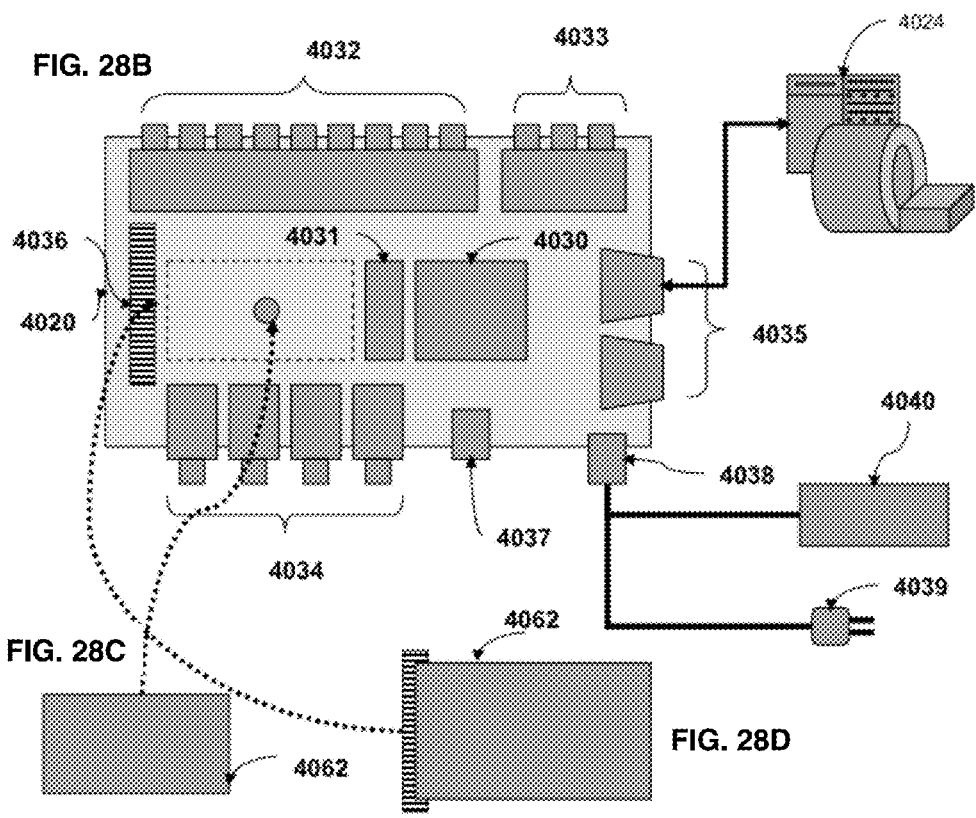
FIG. 28B
FIG. 28C
FIG. 28D

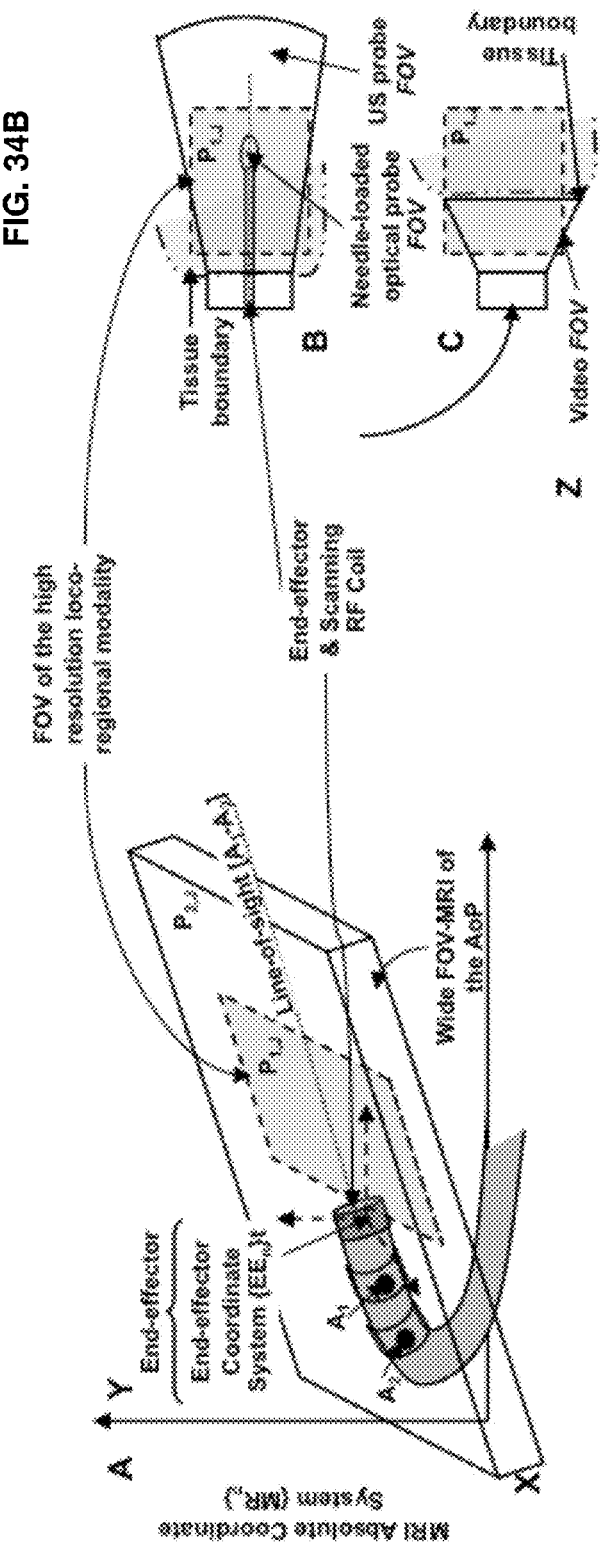

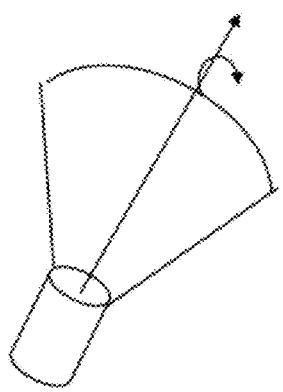
FIG. 34D
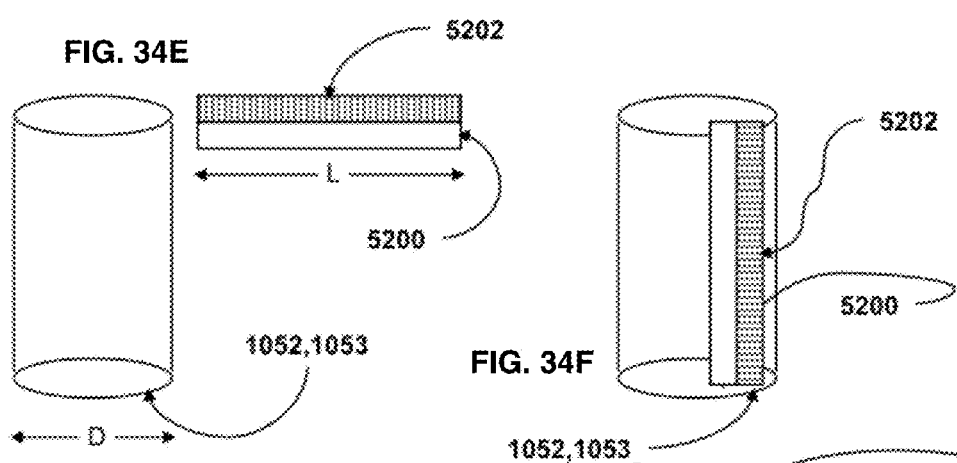
FIG. 34E
FIG. 34F
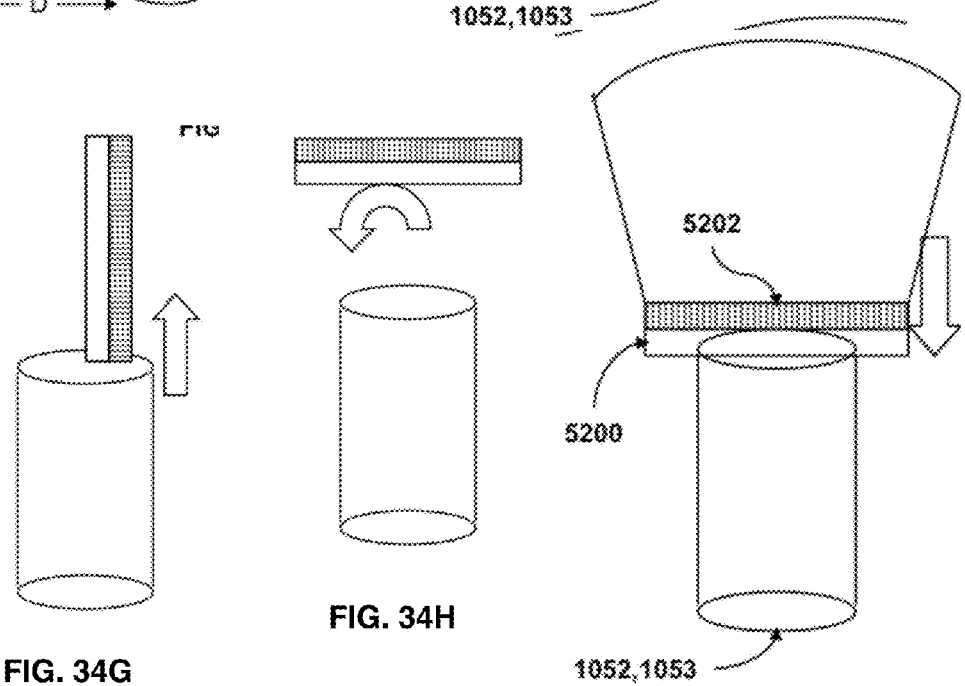
FIG. 34G
FIG. 34H
FIG. 34I

ROBOTIC DEVICE AND SYSTEMS FOR IMAGE-GUIDED AND ROBOT-ASSISTED SURGERY

FEDERAL FUNDING LEGEND

This invention was made with governmental support under Grant Number CNS-0932272 awarded by the National Science Foundation. The government has certain rights in the invention.

CROSS-REFERENCE TO RELATED APPLICATIONS

This application is a non-provisional under 35 U.S.C. §119(e) of provisional application U.S. Ser. No. 61/692,943, filed Aug. 24, 2012, the entirety of which is hereby incorporated by reference.

BACKGROUND OF THE INVENTION

Field of the Invention

The present invention relates to the fields of robotics, robot assisted surgical procedures and software for the practice thereof. Specifically, the present invention provides a robotic system, including a robotic manipulator and actuator and applicable software and hardware, comprising an MRI-compatible medical robotic platform for in situ, real time image-guided diagnosis, surgeries and minimally invasive medical interventions.

Description of the Related Art

Robotic assistance in minimally invasive procedures, including Single Port Access SPA surgeries and percutaneous interventions, is emerging as a more patient-friendly, practice-enhancing and, eventually, cost-effective alternative to traditional open surgeries or free-hand interventions. Such a paradigm shift requires robust, scalable and efficient methodology for integrating multimodal sensing, e.g., tissue and molecular level imaging, controlled systems such as robots and haptic devices, and, for example, the surgical, radiological, cardiological, etc. interventionalist. Major efforts by pioneering groups in developing innovative computational methods, robotic manipulators and haptic interfaces have paved the way toward this quantum leap. Looking into the future of image guided and robot-assisted IGRA procedures, several factors may contribute to next-generation systems, including the seamless integration of real-time image guidance that can locally assess the tissue pathology and function, with efficient operator interfacing.

Real-Time Image Guidance RTIG offers unique features for assessing the Area of Procedure AoP, including 1 assessing real-time tissue deformation and motion, secondary to the procedure or natural motion, e.g. breathing or heart beating; 2 monitoring the tools in 3D; and 3 updating the pathophysiology information of the targeted tissue. Endowed with such features, Real-Time Image Guidance may facilitate a paradigm shift and methodological leap from current approaches of "keyhole" visualization, i.e. endoscopy or laparoscopy, and pre-operative imaging guidance, to a more global and informational-rich perception of the AoP, which can enable a wider range and levels of complex surgeries. Within this context, extensive ground-breaking work has been performed with different imaging modalities, including ultrasound US, and magnetic resonance imaging MRI, for free-hand or robot-assisted procedures.

Image guided and robot-assisted procedures are challenging, highly complex and a wide range of clinical paradigms and enabling technologies have been or are currently pursued by many groups. Several image guided and robot-assisted devices have been developed or are under development. The MR-compatible NeuroArm, which may revolutionize MRI-guided surgeries, is a complex and high-cost technology, but it is unsuitable for real-time MR guidance. Another system, studied at the National Institutes of Health, is based on the Innomotion® robot, which is no longer offered commercially.

Thus, there is a recognized need in the art for improved image-guided and robot assisted procedures, particularly for real-time multimodality imaging for robot control and HIMI for man-in-the-loop autonomous or manual control of the robot. More specifically, the prior art is deficient in robotic devices, systems and methods that are designed for operation within the space constraints of imaging scanners, means for actuating the robot that can perform in the very high magnetic field of a magnetic resonance environment and enable real-time tracking of tissue. The present invention fulfills this long-standing need and desire in the art.

SUMMARY OF THE INVENTION

The present invention is directed to a robotic system for a robot-assisted surgical procedure. The robotic system comprises at least one image-guided robotic manipulator device, means for actuating the robotic manipulator device which is mechanically linked thereto and a computer having a memory, a processor and at least one network connection in electronic communication with the robotic manipulator and the means for actuating the same. The present invention is directed to a related robotic system further comprising at least one movable, rotatable and mechanically-linkable base onto which the robotic manipulator device is secured where the base is movably oriented to fit an area of the surgical procedure on a patient. The present invention is directed to a related robotic system further comprising at least one sensor configured to send and receive signals from an imaging system effective to guide an imaging modality and, optionally, a plurality of contrast markers disposed on or around the robotic manipulator device effective to accurately register the same.

The present system also is directed to a method for performing a robot-assisted surgical procedure under image guidance in real time on a patient. The method comprises positioning the robotic system, as described herein, proximate to the patient, adjusting orientation and position of at least one movable, rotatable and mechanically-linkable base onto which the robotic manipulator device is secured and then the patient is imaged via an imaging modality. The robotic manipulator comprising the robotic system is guided in real time to an area for the procedure on the patient via information electronically obtained during imaging. The surgical procedure is performed on the patient via the image-guided robotic manipulator. The present invention is directed to a related method further comprising obtaining information from one or more imaging or non-imaging sensors registered with the robotic manipulator that comprises a first global positioner unit, a second unit to the first unit and to a third unit comprising the sensors for receiving additional information about a tissue in the area of the procedure.

The present invention is directed further to a magnetic resonance image (MRI) guided robot for performance of a surgical procedure, comprising a global positioner having at least one movable stage configured to move with at least one degree of freedom and a plurality of units interfaced with a magnetic resonance imaging system; at least one movable, rotatable and mechanically linkable base on which to secure the global positioner where the base is movably oriented to fit an area of the surgical procedure on a patient; at least one actuation transmission line comprising a flexible component having a plurality of linearly disposed spheres comprising a displaceable medium, a rigid component having a plurality of linearly disposed pistons or an alternating combination thereof mechanically or electronically linked to the global positioner and to an actuation power source and electronically connected to a robot control module comprising a computer or to a manually controlled robot controller such that at least one actuation transmission line is configured for actuation of one degree of freedom of the global position; and at least one wired or wireless network link to the computer that tangibly stores in memory software modules having processor-executable instructions to operate the magnetic resonance imaging system and the robot. The present invention is directed to a related MRI guided robot that further comprises at least one radiofrequency coil disposed proximate to the global positioner or to a global positioning first unit comprising the global positioner or to any other location on the robot effective to image a workspace thereof, where the radiofrequency coil is configured to send and receive signals from the MR imaging system and, optionally, a plurality of contrast markers disposed on or around the robot effective to accurately register the same. The present invention is directed to another related MRI guided robot wherein when two or more movable stages are disposed in a parallel relationship, the robot further comprises at least one mechanical link therebetween.

The present invention is directed further still to a real time magnetic resonance image guided method for performing robot-assisted surgery on a patient. The method comprises rotating, translating or rotating and translating the base of the global positioner to correspond to the position of the patient for imaging such that a workspace of the global positioner includes the area of the procedure and securing the base comprising the robotic manipulator in the adjusted position. The MR imaging system is co-registered with the global positioner, which is then guided in real time within one or more degrees of freedom to align with an area on the patient for the surgery via a coordinate system comprising the MR imaging system. One or more surgical devices registered with the global positioner are deployed into the patient, thereby performing in real time magnetic resonance image guided surgery thereon. The present invention is directed to a related MRI guided method further comprising obtaining information from one or more imaging or non-imaging sensors registered with global positioner comprising a first global positioner unit, a second unit to the first unit and to a third unit comprising the sensors for receiving additional information about a tissue in the area of the procedure.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and, therefore, are not to be considered limiting in their scope.

FIG. 1A: Hardware components. FIG. 1B: Software components.

FIG. 5A: Device that maneuvers a straight tool and enters into the patient's body via a Point Constraint port. FIG. 5B: The flowchart of the operation of the robotic device.

FIG. 6A: Device that maneuvers a bendable tool and enters into the patient's body via a Point Constraint port. FIG. 6B: The flowchart of the operation of the robotic device.

FIGS. 7A-7B: Schematics of operation for a robotic device. FIG. 7A: Device that maneuvers a straight tool and enters into the patient's body via a non-constraint port. FIG. 7B: The flowchart of the operation of the robotic device.

FIG. 8A: Device that maneuvers a bendable tool and enters into the patient's body via a non-constraint port. FIG. 8B: The flowchart of the operation of the robotic device.

FIGS. 10A-10M: Examples of embodiments pertinent to the flexibility of the same robotic platform to be adopted for access to different anatomies and patient positioning by changing the employed base.

FIG. 12A: attaching the coil onto the robot. FIG. 12B: Attaching the coil onto the patient or on both sides one or more RF coils for improving the SNR locally at the area where the operation is performed. FIG. 12C: Two separate coils are used, a set on the robot and another on the patient, then the two sets can be implemented as two independent coil sets, i.e. each set is connected to separate dedicated RF channel on the MR scanner, or as a single RF coil unit. FIG. 12D: Current commercial RF coils can be used using appropriate software of this disclosure that maps the available access via the openings of the commercial coil and for this particular robot. Thus, the robot will have even a wider range of applicability.

FIGS. 14A-14F: Depicts configurations of the bendable third unit that enable reaching the target area.

FIG. 15: The rigid-liquid actuation transmission system components resembling a conventional hydraulic or pneumatic system.

FIGS. 16A-16F: Depict configurations of the spheres with or without a ring and parameters of the tubing and transmission lines. FIG. 16A: The diameter dl of the spheres is substantially smaller than the inside diameter h1 of the hose.

FIG. 16B: A ring is located in-between each sphere to eliminate friction forces that can drive the spheres in opposite directions. FIG. 16C: The diameter of the spheres is less than the inside diameter of the hose. The ring is located in-between each sphere and keeps the spheres centered and the spheres at distant positions and eliminates friction forces that can drive the spheres in opposite directions. FIG. 16D: Depicts a flexible wire or line through the spheres for push-pull motion. FIG. 16E: Depicts the inner diameters of the components of the actuation transmission line. FIG. 16F: A cross-sectional view of the tubing depicting an internal sleeve-like component.

FIGS. 17A-17G: Depict the actuation system including one or more openings or slits along the length of the container tubing. Those openings or slits are used for linking the rigid fluid to actuate components and the position encoder.

FIG. 18A: A rigid portion of hose at the end of the actuator where the link or piston of the system is sliding to eliminate frictions or restrictions. FIG. 18B: A substantially longer part of a rigid tube is used to reach the position of the actuated applicator to eliminate increased friction or altering the internal diameter of the tube; the distal portion can then be flexible. Multiple rigid tubes can move the actuation to the place of the robot manipulator and then use flexible ones to connect with the actuated parts of the robot.

FIGS. 19A-19E: Example implementations of the rigid liquid transmission line with a combination of spheres, pistons, straight and bendable tubing. FIG. 19A: A transmission line with rigid tubing, spheres and a piston configuration. FIG. 19B: A transmission line comprising a straight rigid tubing with spheres and pistons separated by flexible tubing with spheres. FIGS. 19C-19E: Disposition of the transmission line on the patient couch in relationship to the robot base and motor.

FIGS. 20A-20H: Examples of linking the "rigid liquid" actuation lines to the actuated components.

FIGS. 21A-21C: Methods for actuating multiple lines of rigid liquid lines.

FIG. 22A: Depicts the component parts of a staging block. FIG. 22B: Depicts the incorporation of rigid and flexible components in the container tubes.

FIGS. 23A-23L: Perspective assembled and exploded views of the stage and the robotic manipulator. FIGS. 23A-23B: Movement along the Z-axis. FIGS. 23C-23D: Movement along both the X-axis and Z-axis. FIGS. 23E-23L: Views of a working robot manipulator.

FIG. 25A: Coupling where flexible and rigid tubing have the same inner diameter. FIG. 25B: Coupling where flexible and rigid tubing have different inner diameters.

FIG. 26A: Only manual actuation depicted. FIG. 26B: Powered actuation with manual by-pass.

FIG. 27A: Architecture of the MAU composed of a handle with DoF such that they replicate those of the actual robot in an 1-to-1 ration. FIG. 27B: Arrangement of the MAU handle with the operator holding it in-between the two anchor points of the handle via which the human actuation is transferred to the actuation lines. FIG. 27C: Arrangement of the MAU handle with the operator holding it above, or equally below, the two anchor points of the handle via which the human actuation is transferred to the actuation lines.

FIGS. 28A-28D: Configuration of imaging scanner. FIG. 28A: Architecture of the system for controlling the imaging scanner directly from the manual-actuation unit (MAU). FIG. 28B: Example of a single-board electronic unit that contains all needed hardware components for performing this task. FIG. 28C: A video card is part of a single board implantation. FIG. 28D: A video card is an add-on via a suitable bus.

FIG. 29A: MAU electronic unit with the option of the position encoder signal digitization and counting component and associate software as separate from the single-board implementation. FIG. 29B: MAU electronic unit with the option of the position encoder signal digitization and counting component and associate software as a single-board implementation.

FIGS. 34A-34I: Sensing with robot mounted sensors. FIG. 34A: Schematic of combining the primary guiding modality with sensing with the robot-mounted sensors. FIG. 34B: Schematic showing an extendable needle carried by the robot end-effector and guided by the robot-mounted sensor for tissue penetration. FIG. 34C: Schematic showing a sensor on the surface of the end-effector for tissue-to-tissue contact. FIG. 34D: Depicts probe actuation to produce cone-like or funnel-like 3D imaging. FIGS. 34E-34I: Depicts various mechanisms of deploying a sensor or a tool.

FIGS. 36A-36B: Control of the robot using both MRI and ultrasound data collected in real-time. FIGS. 36C-36D and generation of dynamic virtual fixtures on-the-fly from the real-time collected data.

FIG. 37A: Arrangement of straight tubing on known positions onto the stage of the robot that are visible with MR imaging. FIG. 37B: A preferred version of the tubing that is wrapped around by an inductively coupled RF coil (as example, but not limited to, a spiral (upper) or a rectangular (lower)) for use with low flip angle (1-2 degrees) imaging. FIGS. 37C-37D: registration based on the collection of three projections of three volumes along the a=es of the MR scanner. FIGS. 37E-37G: registration based on the collection of imaging planes.

DESCRIPTION OF THE PREFERRED EMBODIMENTS

Figure 1A:
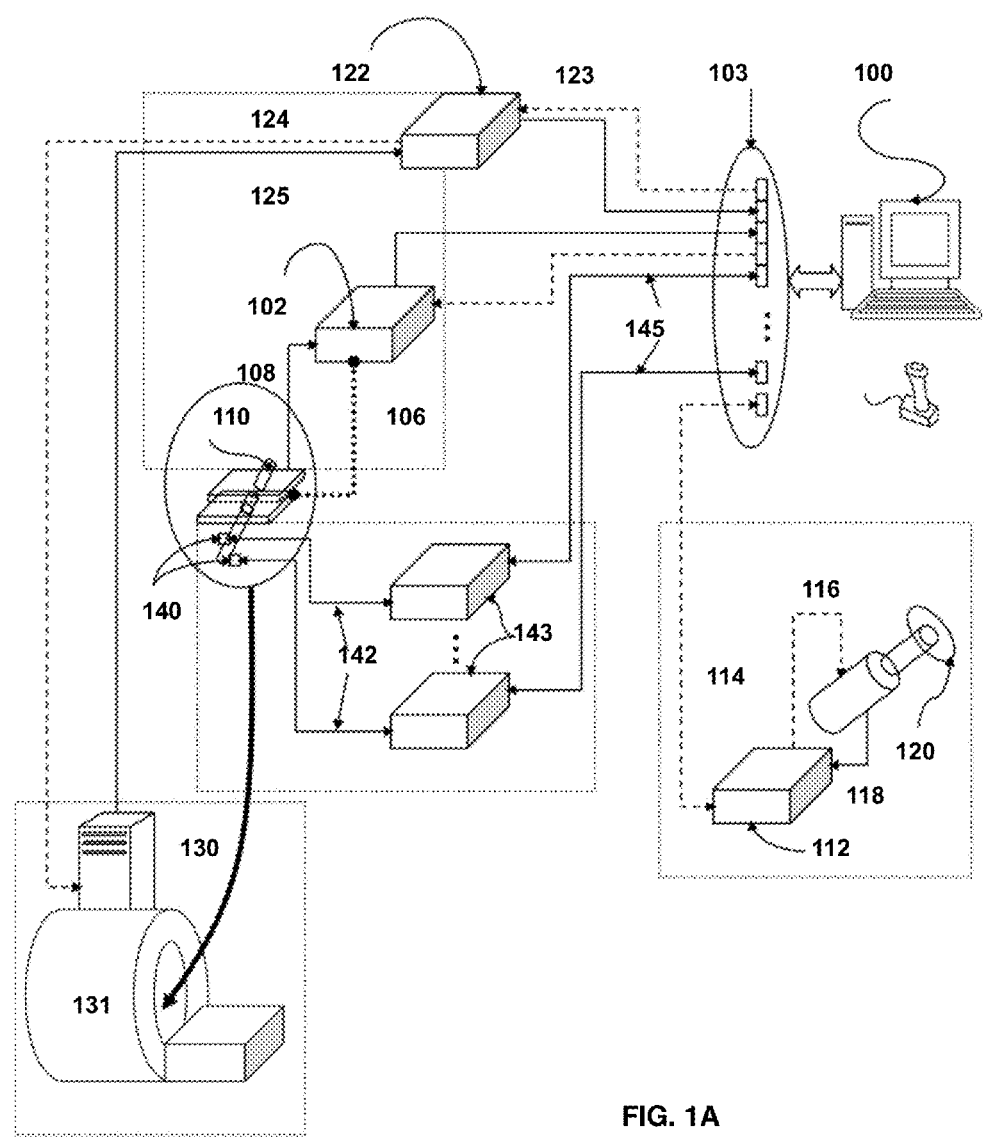
FIG. 1A-1B: Block diagrams of the system components and their interconnectivity.

As used herein, the term "a" or "an", when used in conjunction with the term "comprising" in the claims and/or the specification, may refer to "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

As used herein, the term "or" in the claims refers to "and/or" unless explicitly indicated to refer to alternatives only or the alternatives are mutually exclusive, although the disclosure supports a definition that refers to only alternatives and "and/or."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the terms "computer" refers to one or more machines that comprise at least a memory, a processor and at least one wired and/or wireless network connection. A computer may comprise a desktop or laptop machine or other electronic media, for example, a smartphone or tablet, as are standard and currently known in the art. Without being limiting, any software, modules, applications, add-ons, plug-ins, programs and/or databases, etc. necessary for implementation of, but not limited to, the robot system, including the robotic manipulator, robotic sensors, etc., may be programmed into one or more computers, may be retrieved over the network connection or may be retrieved from a media storage device tangibly storing the same, may be tangibly stored in computer memory or other electronic media memory and are executable by the processor.

As used herein, the terms "robot" or "robotic manipulator" interchangeably refer to the remotely actuated manipulator for performing, for example, but not limited to, manipulator-assisted surgical, minimally invasive surgical and interventional diagnostic or therapeutic or a combination of diagnostic and therapeutic procedures, as described herein.

As used herein, the term "patient" refers to any mammal, preferably a human, that is the subject of a surgical procedure, surgery or minimally invasive procedure utilizing the image-guided robotic device and system described herein.

In one embodiment of the present invention there is provided a robotic system for a robot-assisted surgical procedure, comprising at least one image-guided robotic manipulator device; means for actuating the robotic manipulator device mechanically linked thereto; and a computer having a memory, a processor and at least one network connection in electronic communication with the robotic manipulator and the means for actuating. Further to this embodiment the robotic system may comprise at least one movable, rotable and mechanically-linkable base onto which the robotic manipulator device is secured where the base is movably oriented to fit an area of the surgical procedure on a patient. In another further embodiment, the robotic system may comprise at least one sensor configured to send and receive signals from an imaging system effective to guide an imaging modality; and, optionally, a plurality of contrast markers disposed on or around the robotic manipulator device effective to accurately register the same. In all embodiments components comprising the robotic system comprise materials are compatible with an imaging modality configured for use in the surgical procedure.

In all embodiments the robotic manipulator device comprises at least one movable stage configured to move with one or more degrees of freedom. Particularly, when two or more of the movable stages are disposed in a parallel relationship, the robotic system further may comprise at least one mechanical link therebetween In all embodiments the robotic manipulator device may comprise at least one first unit configured for global positioning; at least one second unit, one of the second units movably linked to the first unit; at least one third unit comprising one or more surgical devices or modalities, one of the third units movably linked to one of the second units and deployable into a body via the second unit; and a plurality of interfaces in electronic communication with the first, second or third units or a combination thereof and the computer, each of the units independently or in combination configured for co-registration thereof over the interface. The robotic manipulator device further may comprise one or more imaging or non-imaging sensors internally or externally disposed in relationship to a patient's body, where the sensors are registerable with the first, second or third units or a combination thereof. Further still the second unit, the third unit or both of the robotic manipulator device may comprise a rotating element rotatably linked to the one or more sensors. Also the robotic manipulator device may be image-guided during the surgery via registration with an imaging system coordinate system. Representative non-limiting examples of an imaging system are magnetic resonance imaging or spectroscopy or a combination thereof, ultrasound imaging, x-ray computed tomography, x-ray mammography, optical imaging, or video.

In all embodiments the means for actuating the robotic manipulator device may comprises at least one actuation transmission line mechanically or electronically linked to the robotic manipulator; and an actuation power source mechanically connected to the actuation transmission line and electronically connected to a robot control module comprising the computer or to a manually controlled robot controller. Also, in all embodiments at least one actuation transmission line may be configured for actuation of one degree of freedom of the robotic manipulator device.

In one aspect of these embodiments the actuation transmission line may comprise a plurality of spheres comprising a displaceable medium; a movable, flexible tubing containing the plurality of spheres; and a linearly translatable first plug-like component disposed at one or both ends of the flexible tubing, where the first plug-like component is in mechanical communication with the flexible tubing and the actuation power source such that actuation thereof is transmitted through the plurality of spheres to the robotic manipulator device or to at least one base securing the same.

Further to this embodiment the flexible tubing may comprise one or more openings disposed along the length thereof; and a second plug-like link positioned between two adjacent spheres and extending through the opening; or a structure external to the flexible tubing movably engaged with one or more spheres through the opening, where the second plug-like component or the external structure is directly or indirectly in mechanical communication with the actuation power source such that actuation is transmitted therethrough. Further still to this aspect the flexible tubing may comprise a plurality of rings disposed within the flexible tubing, where each of the rings is disposed between one or more pairs of adjacent spheres where the plurality of rings replaces one or more spheres within the flexible tubing, where the rings comprise means for centering the spheres and reducing friction within the tubing. Further still the flexible tubing may comprise an internal lubricating sleeve disposed between an inner surface of the flexible tubing and the plurality of spheres; and an external transversely stiffening sleeve disposed around an outer surface of the flexible tubing and extending partially or completely along the length thereof.

In another aspect the actuation transmission line may comprise a plurality of rigid pistons; a rigid tubing containing one or more pistons linearly disposed therein, where the tubing is in mechanical communication with the actuation power source such that actuation thereof is transmitted through the plurality of pistons to the robotic manipulator device or to at least one base securing the same; and means for maintaining rigidity and friction in the linear displacement of the pistons disposed linearly within the rigid tubing. Further to this aspect the rigid tubing may comprise one or more of the spheres, as described supra, linearly disposed therein and an internal lubricating sleeve disposed between an inner surface of the rigid tubing and the one or more spheres.

In yet another aspect the actuation transmission line may comprise in alternating sequence one or more rigid tubing segments containing a plurality of rigid pistons and means for maintaining rigidity and friction in the linear displacement of the pistons, both linearly disposed within the rigid tubing, where the pistons are in mechanical communication with the actuation power source actuated parts of a base securing the robotic manipulator device or actuated parts of an implement; and one or more movable, flexible tubing segments containing in linear disposition a plurality of spheres comprising a displaceable medium and a plurality of rings each positioned between adjacent spheres, where the flexible tubing is attached to the rigid tubing such that actuation of the rigid tubing is transmitted through the rigid pistons to the plurality of spheres and to the robotic manipulator device or the base or the implement.

In both embodiments the computer may tangibly store in memory software modules having processor-executable instructions to establish a plurality of interfaces among at least the robotic manipulator, an imaging modality to guide and operate the robotic manipulator, a plurality of imaging or non-imaging sensors to collect data about a condition of a tissue at an area of the procedure, a plurality of sensors to collect data about the robotic manipulator and to measure a motion of one or more degrees of freedom, and an operator of the system; receive data collected from the imaging modality and the plurality of sensors and generate in real-time a model of the area of the procedure and, if needed, process the data; generate and regulate type and timing of data collection and communicate instructions about the same to the data collection imaging or non-imaging sensors; and generate static or dynamic paths and trajectories for the robotic manipulator effective to avoid or resolve collisions and to accurately reach the tissue; generate instructions for the control of the robotic manipulator and communicate the same to a robot control module; send force and visual feedback to the operator; and receive commands from the operator.

In another embodiment of the present invention there is provided a method for performing a robot-assisted surgical procedure under image guidance in real time on a patient, comprising the steps of positioning the robotic system, as described supra, proximate to the patient; adjusting orientation and position of at least one movable, rotatable and mechanically-linkable base onto which the robotic manipulator device is secured; imaging the patient via an imaging modality; guiding in real time the robotic manipulator comprising the robotic system to an area for the procedure on the patient via information electronically obtained during imaging; and performing the surgical procedure on the patient via the image-guided robotic manipulator. Further to this embodiment the method may comprise obtaining information from one or more imaging or non-imaging sensors registered with the robotic manipulator comprising a first global positioner unit, a second unit to the first unit and to a third unit comprising the sensors for receiving additional information about a tissue in the area of the procedure.

In both embodiments the adjusting step may comprise rotating, translating or rotating and translating the base of the robotic manipulator to correspond to the position of the patient for imaging such that a workspace of the robotic manipulator includes the area of the procedure; and securing the base comprising the robotic manipulator in the adjusted position. In an aspect of these embodiments the imaging modality may be magnetic resonance where the robotic system is positioned proximate to the patient within the MRI chamber. Particularly, positioning of the robotic manipulator may be computer controlled or controlled manually by an operator. Also in both embodiments the imaging step may comprise co-registering the imaging modality with the robotic manipulator prior to the guiding step. In addition the guiding step may comprise actuating the robotic manipulator within one or more degrees of freedom based on a coordinate system of the imaging modality via the actuation transmission lines mechanically linked thereto. Furthermore the performing step may comprise deploying one or more surgical devices registered with the robotic manipulator into the patient.

In yet another embodiment of the present invention there is provided a magnetic resonance image (MRI) guided robot for performance of a surgical procedure, comprising a global positioner having at least one movable stage configured to move with at least one degree of freedom and a plurality of units interfaced with a magnetic resonance imaging system; at least one movable, rotatable and mechanically linkable base on which to secure the global positioner, where the base is movably oriented to fit an area of the surgical procedure on a patient; at least one actuation transmission line comprising a flexible component having a plurality of linearly disposed spheres comprising a displaceable medium, a rigid component having a plurality of linearly disposed pistons or an alternating combination thereof mechanically or electronically linked to the global positioner and to an actuation power source and electronically connected to a robot control module comprising a computer or to a manually controlled robot controller such that at least one actuation transmission line is configured for actuation of one degree of freedom of the global positioner; and at least one wired or wireless network link to the computer that tangibly stores in memory software modules having processor-executable instructions to operate the magnetic resonance imaging system and the robot. Further to this embodiment the MRI guided robot may comprise at least one radiofrequency coil disposed proximate to the global positioner or to a global positioning first unit comprising the global positioner or to any other location on the robot effective to image a workspace thereof, where the radio frequency coil is configured to send and receive signals from the MR imaging system; and, optionally, a plurality of contrast markers disposed on or around the robot effective to accurately register the same. In both embodiments the robot and components comprising the same comprise materials compatible with a magnetic resonance imaging modality.

In both embodiments two or more of the movable stages may be disposed in a parallel relationship, where the robot further comprises at least one mechanical link therebetween. Also the plurality of units may comprise at least one first unit configured for global positioning; at least one second unit, one of the second units movably linked to the first unit; at least one third unit comprising one or more surgical devices or modalities, one of said third units movably linked to one of the second units and deployable into a body via the second unit; and a plurality of interfaces in electronic communication with the first, second or third units or a combination thereof and the computer, each of the units is independently or in combination configured for co-registration thereof over the interface. In another further embodiment the MRI guided robot may comprise one or more imaging or non-imaging sensors internally or externally disposed in relationship to a patient's body, said sensors registrable with the first, second or third units or a combination thereof. Further still the second unit, the third unit or both of the global positioner may comprises a rotating element rotatably linked to the one or more sensors.

In both embodiments the plurality of spheres may be contained within a movable, flexible tubing further comprising a plurality of rings disposed between one or more pairs of adjacent spheres, wherein the plurality of rings replaces one or more spheres within the flexible tubing where the rings comprise means for centering the spheres and reducing friction within the tubing; and a linearly translatable first plug-like component disposed at one or both ends of the flexible tubing where the plug is in mechanical communication with the flexible tubing and the actuation power source such that actuation thereof is transmitted through the plurality of spheres to the robotic manipulator or to at least one base securing the same. Further still the flexible tubing may comprise one or more openings disposed along the length thereof; and a second plug-like link positioned between two adjacent spheres and extending through the opening; or a structure external to the flexible tubing movably engaged with one or more spheres through the opening, where the second plug-like component or the external structure directly or indirectly in mechanical communication with the actuation power source such that actuation is transmitted therethrough. Further still to this embodiment the flexible tubing may comprise an internal lubricating sleeve disposed between an inner surface thereof and the plurality of spheres and an external transversely stiffening sleeve disposed around an outer surface and extending partially or completely along the length thereof.

In both embodiments the plurality of the plurality of rigid pistons may be contained within a rigid tubing in mechanical communication with the actuation power source such that actuation thereof is transmitted through the plurality of pistons to the robotic manipulator device or to at least one base securing the same where the rigid tubing may further comprise bearings disposed linearly within such that rigidity and friction in the linear displacement of the pistons is maintained. Further to this embodiment the rigid tubing may comprise one or more spheres disposed between adjacent rigid pistons; and an internal lubricating sleeve disposed between an inner surface of the rigid tubing and the one or more spheres. Related to these embodiments in the combination of flexible and rigid components in the actuation transmission line, the flexible component may be attached to the rigid component such that actuation of the rigid component is transmitted linearly therethrough to the flexible component and thereby to the global positioner or to at least one base securing the same.

In both embodiments the software modules tangibly stored in the computer memory may comprise processor-executable instructions to establish a plurality of interfaces among at least the global positioner, the MRI imaging system to guide and operate the global positioner, a plurality of imaging or non-imaging sensors to collect data about a condition of a tissue at an area of the procedure, a plurality of sensors to collect data about the robotic manipulator and to measure a motion of one or more degrees of freedom, and an operator of the system; receive data collected from the imaging modality and the plurality of sensors and generate in real-time a model of the area of the procedure and, if needed, process the data; generate and regulate type and timing of data collection and communicate instructions about the same to the data collection imaging or non-imaging sensors; and generate static or dynamic paths and trajectories for the robotic manipulator effective to avoid or resolve collisions and to accurately reach the tissue; generate instructions for the control of the robotic manipulator and communicate the same to a robot control module; send force and visual feedback to the operator; and receive commands from the operator.

In yet another embodiment of the present invention there is provided a real time magnetic resonance image guided method for performing robot-assisted surgery on a patient, comprising the steps of rotating, translating or rotating and translating the base of the global positioner to correspond to the position of the patient for imaging such that a workspace of the global positioner includes the area of the procedure; securing the base comprising the robotic manipulator in the adjusted position; co-registering the MR imaging system with the global positioner; guiding in real time the global positioner within one or more degrees of freedom to align with an area on the patient for the surgery via a coordinate system comprising the MR imaging system; and deploying one or more surgical devices registered with the global positioner into the patient, thereby performing in real time magnetic resonance image guided surgery thereon. Further to this embodiment the method comprises obtaining information from one or more imaging or non-imaging sensors registered with the global positioner comprising a first global positioner unit, a second unit to the first unit and to a third unit comprising the sensors for receiving additional information about a tissue in the area of the procedure. In both embodiments the global positioner may be computer controlled or controlled manually by an operator.

The present invention provides a robotic device and system utilizable for a wide range of surgical and other interventional procedures and methods for actuating the same. Generally, without being limiting or held to theory, the robotic device, systems and uses thereof are applicable to radiology, cardiology, urology, neurosurgery and/or general surgery to operate any interventional or surgical device and in conjunction with real-time imaging to guide a procedure, such as MRI or CT. The system enables multimodality sensing, modeling of the area-of-procedure, robot control, and human-interfacing. The robotic system comprises a generic robotic manipulator that is highly adaptable for increased applicability, versatility in manufacturing and lower cost.

Generally, the robotic system comprises an MRI-compatible robotic manipulator that can operate within the space constraints of imaging scanners and an actuator that can operate in the very high magnetic field of the MR environment. The actuator provides means to obviate limitations of systems known in the art, such as in the case of pneumatic or hydraulic actuators, special valves or mechanisms, compressibility, leaking fluids, additional space to accommodate the stroke of piston assemblies, and cost. The robotic system is useful for performing surgeries or interventions with real-time magnetic resonance imaging MRI. This technology facilitates performing the procedure with the patient inside the MRI scanner thereby offering the interventionalist or surgeon the information-rich MRI data in real-time or at any point during the procedure.

Thus, also provided are imaging methods and software for the fast registration and monitoring of the maneuvering of the robotic manipulator. More particularly, the robotic manipulator described herein is configured for performing procedures with real-time image guidance and in particular with magnetic resonance imaging MRI and moreover with real-time MRI. It is therefore designed to operate inside the bore of an MRI scanner while the patient resides inside the MRI scanner or any other object on which as example a simulated intervention is performed, such as a phantom, or in vivo on an animal model or ex vivo on a tissue sample. Within this context, intraoperatively real-time MRI is used to guide the operator to maneuver the robot and perform the particular procedures. As such preoperative images collected with MRI or other imaging modalities, such as, but not limited to computed tomography CT or positron emission tomography PET or ultrasound US, can be used preferentially to further enhance the information available for guiding the robot assisted procedure.

Moreover, intraoperatively, the robotic manipulator carries on its end-effector additional sensors to collect local information about the pathology, morphology and function of tissue to supplement real-time MRI. Those imaging or non-imaging sensors preferentially provide information about the pathology of tissue unavailable by conventional real-time MRI, such as assessment of the molecular signatures of cancer, and/or with higher specificity or signal sensitivity. Such examples of Intraoperative sensing are, but not limited to, ultrasound (US), optical spectroscopy, optical imaging (such as optical coherence tomography), MRI with micro-coils, tactile or haptic sensing, or video. The robotic manipulator functions as the means to co-register all of the different modalities or sensors. This is enabled because the location of the sensing element and, thus, of the interrogated tissue, is known relative to the robot by its particular design and manufacture, the position of the robot is known relative to the MR scanner coordinate system, since the robot is initially registered to the MR scanner, and each subsequent position also is known relative to the MR scanner coordinate system.

The robotic manipulator provided herein has a plethora of advantages. It has a low profile, i.e. small size, so is suitable to reside inside the bore of an imaging scanner. The robotic manipulator is secured onto a base, for example, that does not exhibit a long-arm type-like cantilever structure so does not require a large sized and heavy structures to achieve rigidity. As a result, the entire robot is of a smaller construction with a lower weight and a lower cost of manufacturing.

The robot can be positioned at different orientations relative to the object by means of interchangeable bases or mechanically changing bases that have different sizes and designs. This further allows for "one robot" to access different anatomies or different orientations or positioning of the patient thereby further increasing its applicability. It can be utilized by different specialists for different types of procedures at a single clinical site. This flexibility and adaptability further enhances its commercial value. A two-parallel-stage robotic manipulator further reduces manufacturing cost since it can be produced of different dimensions, shapes, actuation strokes etc to better fit the particular applications The actuator comprising a "rigid liquid" for remote actuation of the robot also further enhances the commercial value of the robot for MRI-guided procedures. The rigid liquid actuator does not require the use of expensive piezoelectric actuators, or complex, prone to malfunctions or expensive pneumatic or compressible hydraulic actuators.

The robotic manipulator is a generic global positioner that can be easily adopted to carry and manipulate interventional or surgical implements of third party original equipment manufacturers OEM. As such it is not meant to compete with existing technologies, rather to be a tool that cooperates with them, such as by maneuvering the tool produced by an OEM. The robotic manipulator comprises an end-effector that has interchangeable interfaces suitable for attaching, carrying and manipulating virtually any currently used device or any device that may be produced in the future or any straight or bendable or steerable device. The robotic manipulator can be utilized with devices for procedures, such as, but not limited to, tissue cryo-ablation, thermal ablation by means of laser or radiofrequency, biopsy, including, but not limited to core, vacuum assisted or fine-needle aspiration FNA, multi-site FNA with the combination of a multi-sample holder, such as a rotating or linearly advancing carrousel, and/or local delivery of therapeutic or diagnostic agents.

Moreover, the robotic manipulator can be utilized in devices configured for scanning where the sensors are placed externally to the patient's body, such as for robot-mounted ultrasound. In this instance the robot is both the carrier and mechanical scanner of the robot-mounted sensors. The robot also is the mechanical link for co-registering the primary guidance modality, such as MRI, and the robot-mounted modality, such as US or optical, by means of an initial and/or intermittent registration of the robotic manipulator to the inherent coordinate system of the primary guidance modality. If such exists, and/or to an external means of spatial co-registration, such as optical tracking as is well-known in the art. The robotic manipulator also can be utilized in devices for scanning with sensors internally to the patient's body, such as robot-mounted US, optical imaging, optical spectroscopy, localized MRI, etc.

Furthermore, the robotic manipulator can carrying surgical tools or other implements to perform single-port access surgical procedures. Multiple robotic manipulators may be combined, with each carrying complementary surgical or interventional tools, to perform multi-port access surgical procedures.

As described below, the invention provides a number of advantages and uses, however such advantages and uses are not limited by such description. Embodiments of the present invention are better illustrated with reference to the Figure(s), however, such reference is not meant to limit the present invention in any fashion. The embodiments and variations described in detail herein are to be interpreted by the appended claims and equivalents thereof.

Figure 1B:
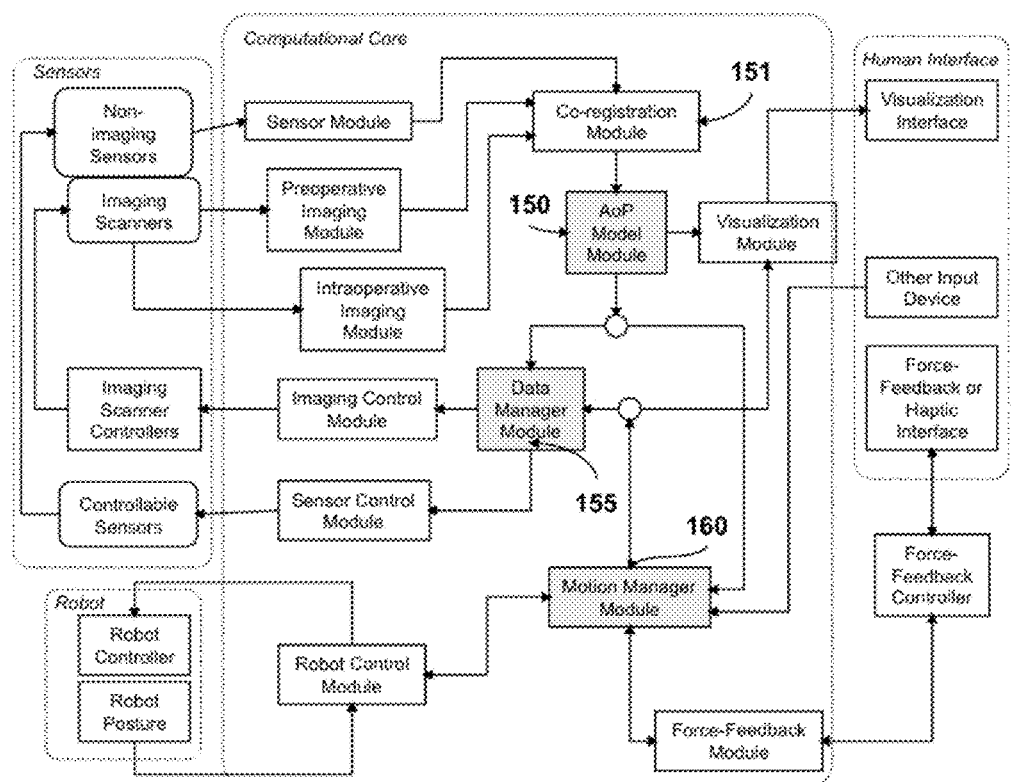
Figure 2A:
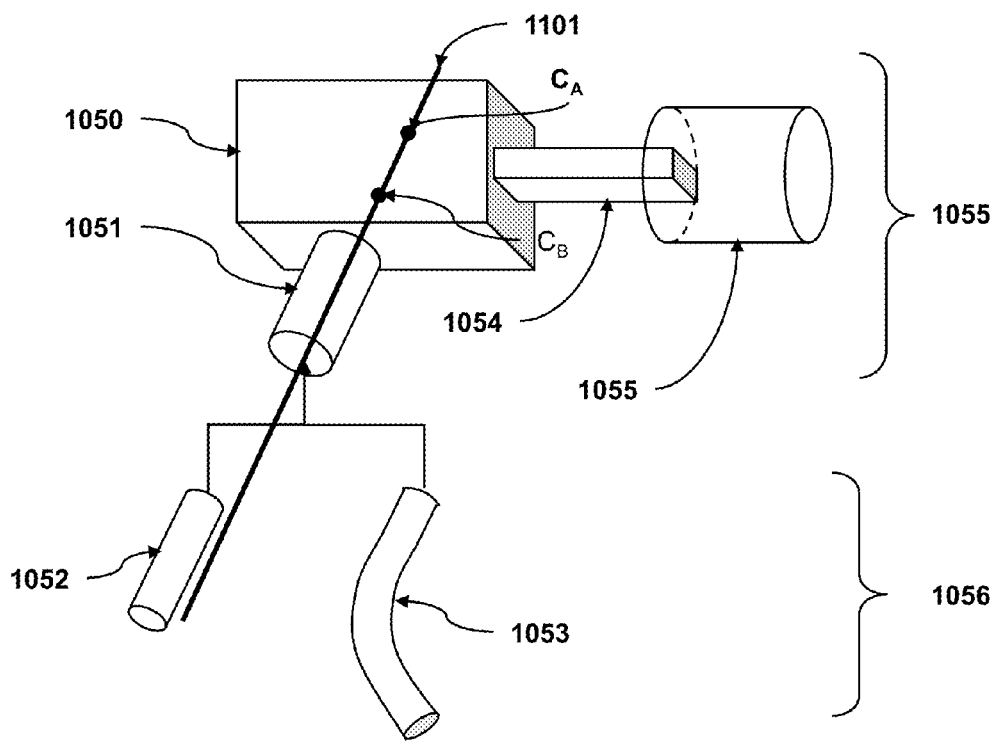
FIGS. 2A-2B: Schematics of the robotic device and its components
Figure 2B:
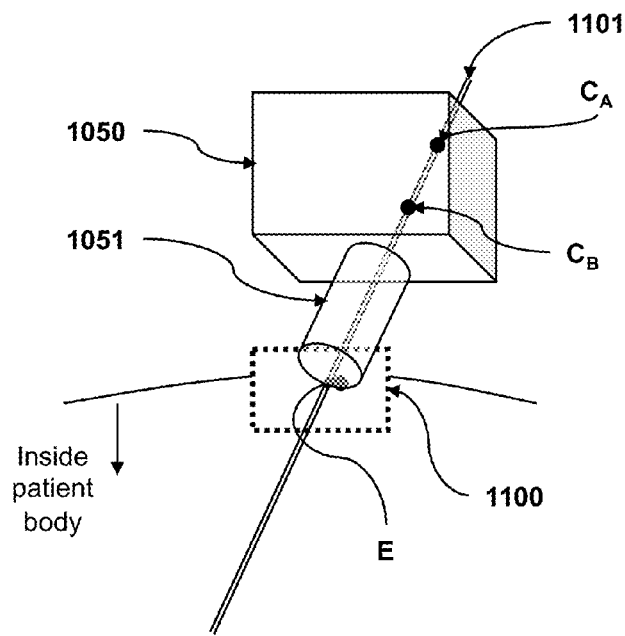

In preferred embodiments of the present invention and as depicted in FIGS. 1 and 2A-2B, the robotic system comprises a plurality of hardware components that are connected to a central computer 100 that hosts software 103 and has a central computational core 150 which processes data, generates commands to the different components, synchronizes their operation and interfaces the human to the system. The system comprises a plurality of hardware and software components for the control of the robotic manipulator that includes an electronic unit 102, with associated resident software 103, which receives commands from the central computer 100 for the control of the robotic manipulator 110. Unit 102 may be, for example, an embedded computing unit that further includes a plurality of analog-to-digital converters, counters, digital-to-analog converters, and digital input/output interfaces.

In one preferred embodiment and particularly in reference to FIG. 1A, unit 102 is connected via a link 104, such as one or a bundle of wires, to the central computer and its associated software module and is dedicated to the control of the robot, to receive control commands in the form of appropriately modulated electronic signals. The electronic control signals received via link 104 are generated are generated by the central computational core 150 via autonomous operation of the robotic manipulator, via manual operation by commands entered by the operator; or by a combination of autonomous and manual operation.

Unit 102 is connected via an actuation transmission link 106 with the robotic manipulator 110 for the remote and controlled actuation of the latter. Unit 102 is connected via a link 108, such as one or a bundle of wires, with the robotic manipulator 110, for receiving signals from one or a plurality of position encoders, and, preferentially, optical encoders, that are appropriately placed on the actuated degree-of-freedom or DoF of the robot 110 to measure the degree of actuation linearly or rotationally. The computational component, i.e., software, of unit 102 further regulates the actuation of the robot 110 via a closed loop scheme by comparing the position encoder signals 108 to the commanded signals 104 and generate internally appropriate commands to adjust the degree of actuation provided via the actuation transmission link 106 to accurately maneuver the robotic manipulator 110.

Also in this preferred embodiment the system includes a plurality of hardware and software entities for the control of a force-feedback unit that entails an electronic unit 112, with associated resident software 113, that links the central computer 100 and a force-feedback or haptic device 120 to interface the operator to the control of the robotic manipulator 110 and/or a plurality of sensors of this manipulator. Unit 112 can be, for example, an embedded computing unit that further includes a plurality of analog-to-digital converters, counters, digital-to-analog converters, digital input/output interfaces, and further links to the motor controllers of the force-feedback unit 120. The computational component software of unit 112 further regulates the actuation of the force-feedback unit 120 to exert forces on the operator to provide information about the procedure as they are generated by the "central computing core" and ii receive guidance commands from the operator for a human-in-the-loop manual or semi-autonomous operation of the robotic manipulator 110.

Unit 112 is connected via a two-way link 114, such as one or a bundle of wires, with the central computer and its associated software module dedicated to the control of the force-feedback unit, to receive and send commands in the form of appropriately modulated electronic signals. Unit 112 also is connected via a link 116, such as one or a bundle of wires, to the motor controllers of the force-feedback unit 120 for the actuation of those motors. Unit 112 is connected further via a link 118, such as one or a bundle of wires, with the force-feedback unit 120, for receiving signals from one or a plurality of position encoders, that are appropriately placed on the actuated DoF of the force-feedback unit 120 to measure the degree of actuation induces generated by the motors and induced by the operator.

In addition in this embodiment, the system comprises a plurality of hardware and software entities for communication with the imaging scanner of the primary guidance modality, such as, preferably, an MRI scanner for i) the real-time control of the scanner by the dedicated module of the central computing core and ii) for receiving in real-time imaging data from the scanner for processing by the dedicated module of the central computing core, that may entail an electronic unit 122, with associated resident software 123, that links the central computer 100 and the scanner's computer 130 that is further connected to the scanner 131 in which resides the patient or object of operation and the manipulator 110. Unit 122 can be, for example, a hub for connecting to the local-area network (LAN) of the scanner to perform the two-way communication and/or a digital signal processing DSP board that preferentially used for real-time and computing efficient processing of the real-time imaging data.

This part of the system comprises a one way link 123,124, that may or may not pass through the unit 122, such as one or a bundle of wires that connects the central computer and its associated software module dedicated to the control of the primary imaging scanner and the scanner to send commands to the scanner in the form of appropriately modulated electronic signals to adjust on-the-fly, i.e. as the interventional procedure evolves, image acquisition parameters that include, but are not limited to, the number, position and orientation of the imaging planes, the contrast of the images, preparatory phases that modulate the magnetization of the tissue to further enhance anatomies or tissue motion or tracking the robot. The system also comprises a one-way link 125,126 for transferring in real-time imaging data from the scanner's computer 130 to the central computing core 101. This one-way link can be implemented as a direct physical connection 125,126 that does not entail the presence and use of the unit 122. Thus, the imaging data are processed at the central computing core. Alternatively, the one-way link can be implemented via a unit 122, such as a DSP, that receives the imaging data via 125 and hosts software for processing of the imaging data. The processed data are sent then via 126 to the central computing core. Utilizing unit 122 is a preferred method for further speeding up imaging data processing.

Furthermore in this embodiment, the system further comprises a plurality of robot-mounted sensors 140, that are not the primary guidance modality(-ies), and a plurality of hardware and software entities for the communication of those sensor(s) with the central computing core of the system. These sensors are, but not limited to imaging-type of sensors, such as, sensors for endoscopic optical imaging, e.g., optical coherence tomography, localized ultrasound, opto-acoustic imaging, and localized MRI with micro-coils, etc., spectroscopy-type, such as sensors for endoscopic optical spectroscopy, e.g., light-induced fluorescence, Raman spectroscopy, MR spectroscopy with RF micro-coils, etc., visual-type sensor, such as cameras, force/tactile-type sensors, and localization-type sensors, such as with RF micro-coils for MR-based localization. The plurality of robot-mounted sensors 140 are further connected by appropriate means 142, such as cables and optical fibers, to a plurality of electronic units 143, with associated resident software 144, that are further connected via appropriate cables to the central computer 100. Units 143 can be, for example, the particular board for the generation and processing of the signals generated by the sensors, a hub for connecting to the local-area network (LAN) of the sensor electronics to perform a two-way communication or a digital signal processing (DSP) board that preferentially used for real-time and efficient computing processing of the real-time sensor data.

In all these embodiments and based on based on manufacturing, commercialization or financial preferences, the plurality of electronic units 102, 112, 122, 143 i) may be individual units that are connected with appropriate interfaces, as known in the art of electronic hardware; ii) may have all or part of them integrated on a single unit and function as a "plug-in to existing personal computers and iii) may be combined into an expandable form factor, such as the PC104, that allows additions of specialized boards in rugged, compact and expandable form. Configurations ii) and iii) may be preferred from the manufacturing point of view to produce units that are commercially more desirable In another preferred embodiment and particularly in reference to FIG. 1B, the central computational core 150 of the robotic system comprises a plurality of pieces of software code that is dedicated to a particular task, known herein as modules, that exchange data among themselves and operate in synchrony for the intended operation and functionality of the system. These modules can be implemented in any manner deemed appropriate for computationally efficient operation, such as, but not limited to, each as a dedicated thread running on a core of a multi-core central processing unit, or part of those modules running to a dedicated hardware, such as an embedded computing unit. The central computing core has three primary modules. These three modules generate instructions and information used by the other modules of the central computational core 150.

The AoP Model Module 152 receives processed data from the primary guiding modality and a plurality of robot-mounted sensors and generates in real-time a realistic model of the area-of-the-procedure (AoP). The data received and used by the AoP Model Module have been processed on-the-fly by software modules dedicated to processing preoperative and intraoperative imaging data from the primary guidance scanner(s) and the robot mounted sensors. These data are processed further by the co-registration module 151 that registers all those data to the same coordinate system preferentially the coordinate system of the primary guidance imaging scanner, relative to which is the robot registered.

The Data Manager Module 155 selects on-the-fly the type of and regulates timing of data collection that needs to be collected by the primary guidance modality and the robot-mounted sensors in order to generate a realistic model of the AoP by the AoP Model Module 150. This module actively controls the imaging scanner and sensors when the latter are of the controllable type. This module can be a dendrite-like scheme based on "if" statements, a machine-learning based code that uses for training data the preoperative data and a scout set of intraoperative data or a combination thereof.

The Motion Manager Module 160 includes routines that generate paths and trajectories for the robot, detect collisions, resolve collisions, and generate instructions for the Data Manager Module 155.

In other preferred embodiments of the present invention, the robot or robotic manipulator comprises a plurality of units that, individually or combined, provide different choices for accessing inside the body of a patient to perform different procedures, as described herein. Generally, the robot comprises at least one first unit 1050 that remains substantially outside the patient's body, at least second unit 1051 that is carried and maneuvered by the first unit 1050 and remains partially outside and partially inside the patient's body and at least one third unit 1052, 1053 that is deployed by the second unit 1051 and can be of straight 1052 or bendable 1053. For example, at 1055 a plurality of units are deployed and maneuvered outside the patient's body and at 1056 a plurality of units are deployed and maneuvered inside the patient's body or both. The position of any of its points, including points on static pieces and points on moving pieces, is known relative to a coordinate system, herein referred to as the global coordinate system. The units 1050, 1051, 1052 also comprise a guidance line 1101 (see FIG. 3).

In one preferred embodiment and particularly in reference to FIGS. 2A-2B, the robot is composed of a first unit 1050, herein referred to as the robotic global positioner unit (rGPU) or global positioner that substantially remains outside the patient's body throughout a procedure. The rGPU comprises a plurality of actuated mechanical subassemblies that carry by means of a permanent or preferentially detachable mechanical means the second unit 1051. The rGPU also comprises a physical or mechanical link 1054 to a generally remotely located source of actuation 1055 for controllably actuate its mechanical subassemblies. The link 1054 is a means for transmitting actuation to the first unit 1050 from a remote actuation source 1055 that operates with energy supplied by an actuator, such as, electromagnetic or piezoelectric motors, hydraulics, pneumatics or other such means or by manual effort of an operator.

Figure 3:
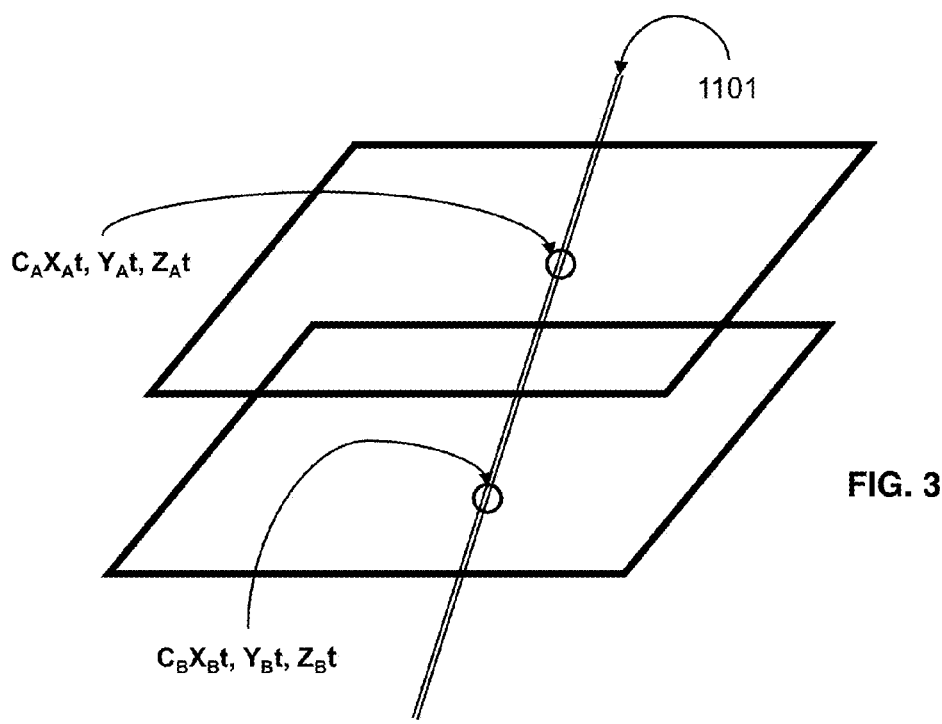
FIG. 3: Schematic of the two actuated points $C_A$ and $C_B$ of the robotic device

In this embodiment and with continued reference to FIGS. 2A-2B, FIG. 3 depicts the mechanical design and kinematic structure of the actuated subassemblies of the first unit 1050 which can perform a combined motion and synchronized motion to maneuver in the 3-dimensional (3D) space and can align the second unit 1051 along a line 1101, herein referred to as the guidance line. The guidance line is defined by two points $C_A$ and $C_B$ where their spatial coordinates $C_A(X_A(t), Y_A(t), Z_A(t))$ and $C_B(X_B(t), Y_B(t), Z_B(t))$ change over time and are known over time relative to the global coordinate system. Points $C_A$ and $C_B$ are subjected to continuous dynamic 3D motion and thus the guidance line 1101 is dynamic. Alternatively, in the specific case, two statically and temporally unchanged, i.e. static, points $C_A$ and $C_B$ and their static spatial coordinates $C_A(X_A, Y_A, Z_A)$ and $C_B(X_B, Y_B, Z_B)$ are known relative to the global coordinate system. Points $C_A$ and $C_B$ are fixed in space and thus the guidance line 1101 is static.

In another alternative embodiment the exact position of any part of the first unit 1050 and the second unit 1051 are now relative to the global coordinate system, and this knowledge is preferentially extracted based on steps that performed manually or preferentially by the computer that controls the robot: 1) initial registration of the robot to the global coordinate system; 2) sampling of position encoders of the robot continuously and in real-time; and 3) feeding the position encoder data to the plurality of the forward kinematic equations that describe the robot. In another alternative embodiment the second unit 1051 remains outside the patient's body and the third unit 1052 is substantially thin at sizes used in needles for transcutaneous procedures via the unbroken skin, such as radio or thermal or cryo ablations, biopsies etc.

Preferably, the robot accesses inside the patient's body via a cut on the patient's skin, and in particularly using a third party port 1100, as known and standard in the art, for single port access surgeries or laparoscopic surgeries or other such type of minimally invasive surgeries, and in generally allows maneuvering a surgical or interventional tool through it as known to the art of the specialists in those types of ports, having mechanical means for providing free angulation or pivoting of the say surgical or interventional tool in a 3D volume, say of a cone shape for accessing different areas in the patient's body according to the design of the particular port. Moreover, and depending on the specific design and manufacturing of the third party port, the port allows pivoting around a specific point (E), herein referred to as "point constraint" port and pivoting and lateral motion, herein referred to as "free-floating" port.

Figure 4A:
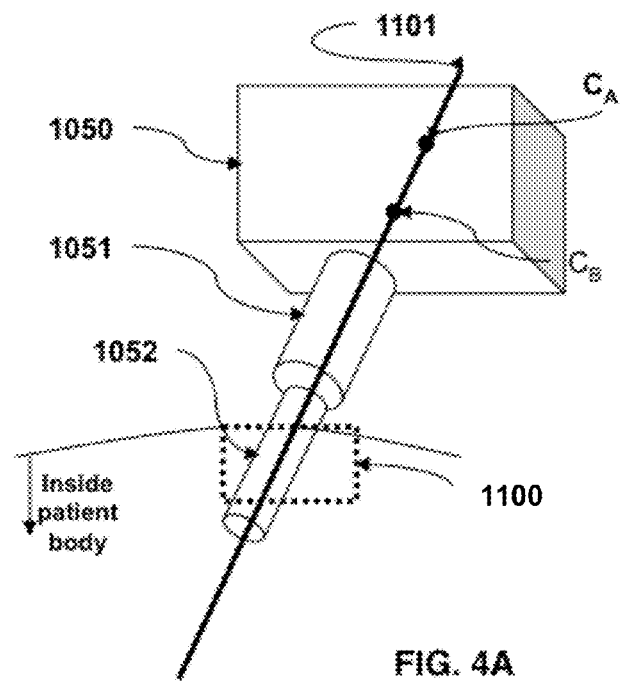
FIGS. 4A-4C: Schematics of the robotic device relative to the access port to the patient body for three cases of entrance of the robotic device into the patient body.
Figure 4B:
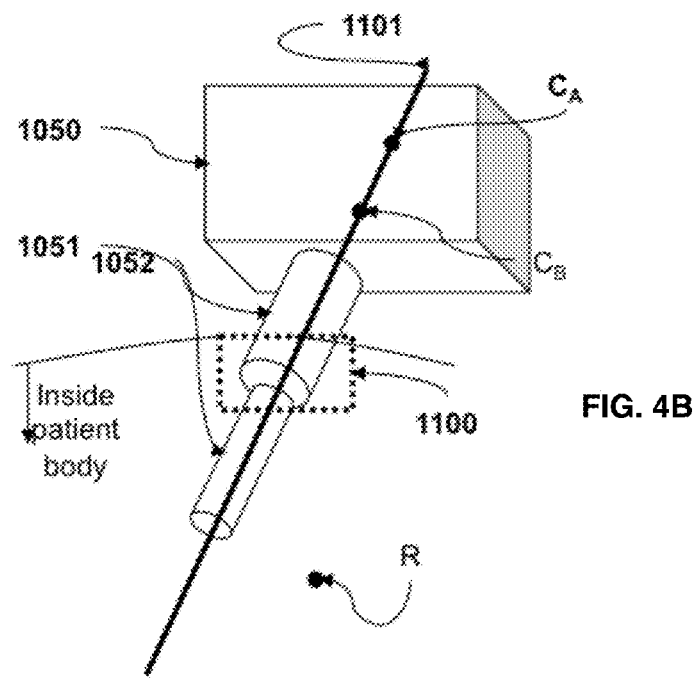
Figure 4C:
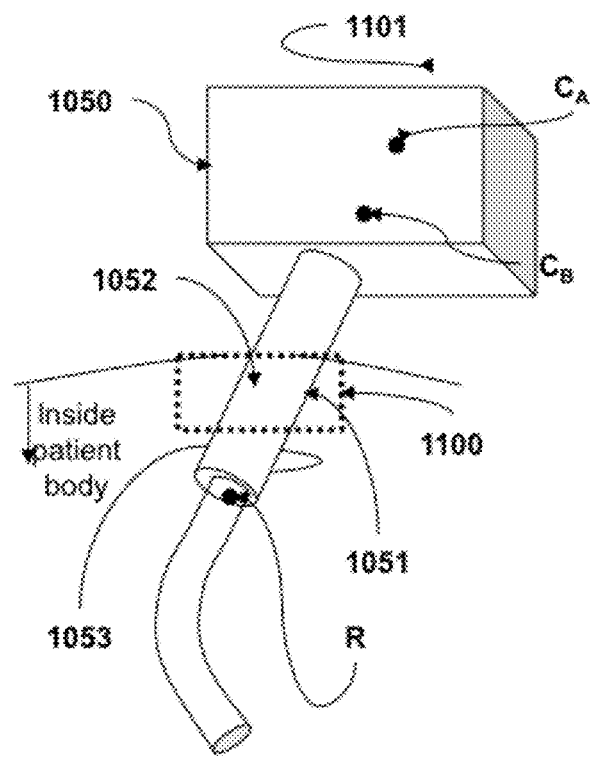

In another preferred embodiment and in reference to FIGS. 4A-4C, depending on the particular needs of the procedure, or the particular design of the third unit 1052, 1053, or the design and operation method of the particular combination of the second unit 1051 and the port 1100, or the design and operation method of the particular combination of the unit 1051 and the third unit 1052, 1053 or any combination of the above, the robot access inside the patient's body via such a port in at least, although not limited to, three alternative ways.

First, in reference to FIG. 4A, the second unit 1051 remains substantially outside the port and a third straight unit 1052 passes in its entirety through the port and extends into the patient's body. Secondly, in reference to FIG. 4B, the distal portion of the second unit 1051 enters into the port and a third straight unit 1052 extends in its entirety into the patient's body. Thirdly, in reference to FIG. 4C, the distal portion of the second unit 1051 enters into the port and further extends beyond the edge of the port, defining a point R in space, to maneuver a preferentially bendable/steerable third unit 1053 that extends in its entirety into the patient's body as to maneuver around an anatomical entity, such as a vital structure or a structure that according to the art of the surgical procedure should not be hit or punctured or penetrated or the same.

Figures 5A, 5B:
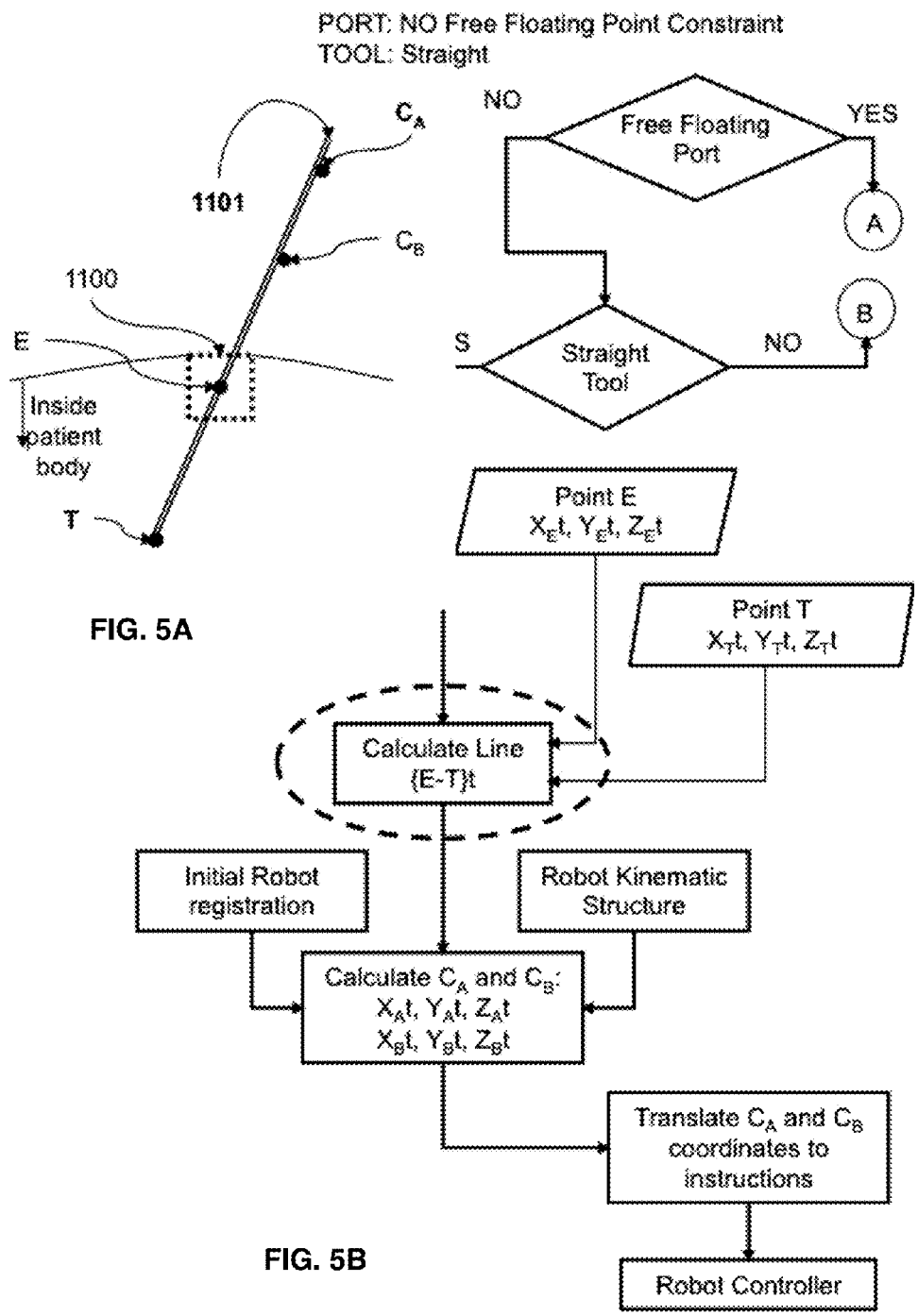
FIGS. 5A-5B: Schematics of operation for a robotic device.

Preferably, the it is known in real-time that the coordinates $X_T(t)$, $Y_T(t)$, $Z_T(t)$ of the target point (T) are known relative to the global coordinate system from imaging or other same methods, the coordinates $X_E(t)$, $Y_E(t)$, $Z_E(t)$ of the say constraint point in the port point (E) are known relative to the robot from tracking methods or if it is static relative to the robot and in turn known to the global coordinate system and the coordinates $X_R(t)$, $Y_R(t)$, $Z_R(t)$ of the say distal point of the say partially extending into the patient's body second unit 1051 from the forward kinematics of the robot, or imaging based tracking methods or the same In another preferred embodiment and in reference to FIG. 5A, the second unit 1051 maneuvers a straight third unit 1052 via an (E) point-constraint port 1100 to reach a target tissue (T) based on the flowchart in FIG. 5B composed of processes performed manually or preferentially in real-time, and on-the-fly, by the say computer or controller of the robot in order the third unit 1052 aligns and advances along the straight trajectory 1101. This is accomplished by first calculating the arithmetic parameters relative to the global coordinate system for defining, i.e. making known, static or dynamic straight line that connects points (E) and (T), referred to as "line {E-T}(t)", using: 1) the coordinates $X_T(t)$, $Y_T(t)$, $Z_T(t)$ of the target point (T) substantially calculated relative to the global coordinate system from imaging or other same methods; and 2) the coordinates $X_E(t)$, $Y_E(t)$, $Z_E(t)$ of the say constraint point in the port point (E) substantially calculated or known relative to the robot from tracking methods or if it is static relative to the robot that in turn is known to the global coordinate system.

The next step comprises calculating the updated coordinates of points $C_A$ and $C_B$ relative to the global coordinate system, i.e. $X_A(t)$, $Y_A(t)$, $Z_A(t)$ and $X_B(t)$, $Y_B(t)$, $Z_B(t)$, respectively, using the 1) specific kinematic design of the robot, and in particular but not limited to the kinematic structure of the first unit 1050, as it is know by the design and construction of this robot, including the design presented later in this invention or any other third party robot that maneuvers an implement based on maneuvering of say two points $C_A$ and $C_B$ in space and 2) the initial registration of the robot to the global coordinate system. Then the updated calculated $C_A$ and $C_B$ coordinates are converted to instructions for the further actuation of the actuated parts of first unit 1050. Finally, those instructions are supplied to the robot controller that further controls the actuators of the robot.

Figure 6A:
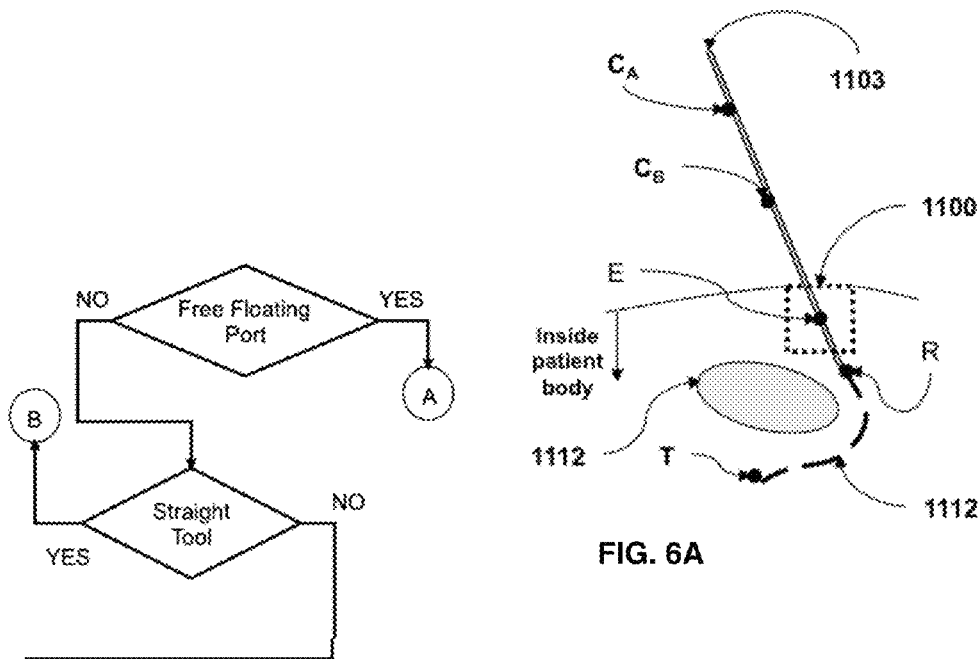
FIGS. 6A-6B: Schematics of operation for a robotic device.
Figure 6B:
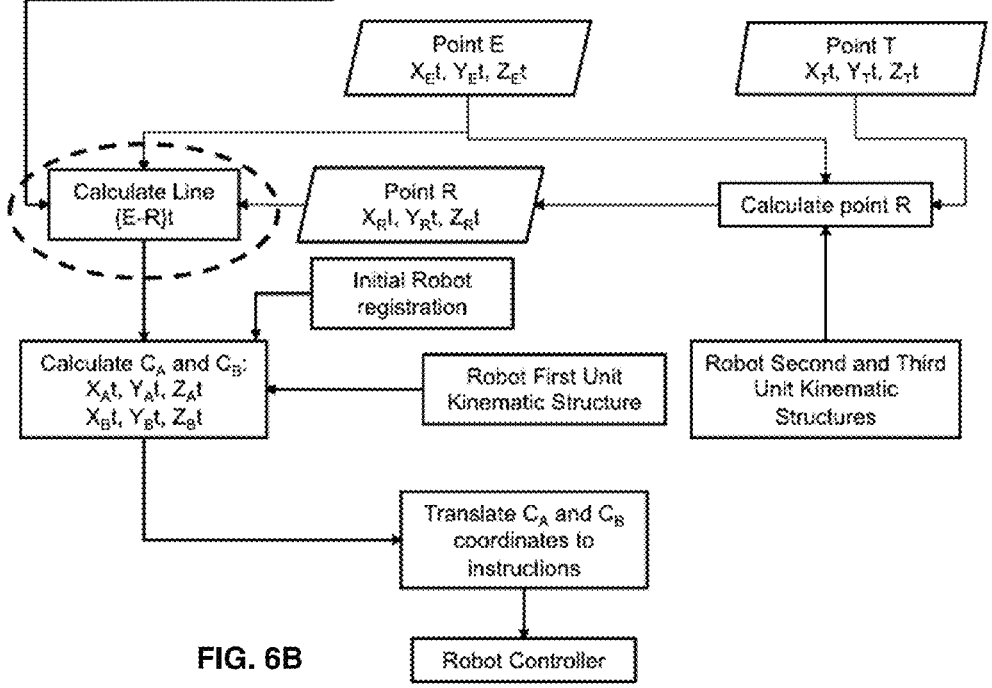

In another preferred embodiment and in reference to FIG. 6A, the second unit 1051 maneuvers a bendable/steerable third unit 1052 via an (E) point-constraint port 1100 to reach a target tissue (T) along a generally curved path 1112, as example to avoid object 1112, based on the flowchart in FIG. 6B composed of processes performed manually or preferentially in real-time, and on-the-fly, by the computer or the controller of the robot so that the third unit 1052 follows the generally curved path 1112. This comprises substantially calculating the coordinates relative to the global coordinate system $X_R(t)$, $Y_R(t)$, $Z_R(t)$ of point (R) at the distal end of the second Unit 1051, based on the coordinates $X_T(t)$, $Y_T(t)$, $Z_T(t)$ of the target point (T) substantially calculated relative to the global coordinate system from imaging or other same methods, the coordinates $X_E(t)$, $Y_E(t)$, $Z_E(t)$ of the say constraint point in the port point (E) substantially calculated or known relative to the robot from tracking methods or, if it is static relative to the robot that in turn is known to the global coordinate system, the specific kinematic design of the robot, and in particular, but not limited to the kinematic structure of the second unit 1050 and the bendable/steerable third unit 1053 as it is known by the design and construction of this robot, including the design presented later in this invention or any other third party robot posses the properties of a bendable/steerable tubular-like extension part.

The next step comprises substantially calculating the arithmetic parameters relative to the global coordinate system for defining, i.e. making known, static or dynamic straight line relative to the global coordinate system that connects points (E) and (R), referred to as "line {E-R}(t)", using the the coordinates $X_T(t)$, $Y_T(t)$, $Z_T(t)$ of the target point (T) substantially calculated relative to the global coordinate system from imaging or other same methods, the coordinates $X_E(t)$, $Y_E(t)$, $Z_E(t)$ of the say constraint point in the port point (E) substantially calculated or known relative to the robot from tracking methods. If it is static relative to the robot that in turn is known to the global coordinate system the step comprises calculating the updated coordinates of points $C_A$ and $C_B$ relative to the global coordinate system, i.e. $X_A(t)$, $Y_A(t)$, $Z_A(t)$ and $X_B(t)$, $Y_B(t)$, $Z_B(t)$, respectively, using the specific kinematic design of the robot, and in particular but not limited to the kinematic structure of the first unit 1050, as it is know by the design and construction of this robot, including the design presented herein or any other third party robot that maneuvers an implement based on maneuvering of two points $C_A$ and $C_B$ in space and the initial registration of the robot to the global coordinate system. The next two steps comprise converting the updated calculated $C_A$ and $C_B$ coordinates to instructions for the further actuation of the actuated parts of first unit 1050 and supplying those instructions to the robot controller that further controls the actuators of the robot.

In yet another preferred embodiment and in reference to FIG. 7A, the second unit 1051 maneuvers a straight third unit 1052 via a free floating (non-constraining) port 1100 to reach a target tissue (T) based on the flowchart in FIG. 7B. These processes are performed manually or preferentially in real-time, and on-the-fly, by the computer or controller of the robot to order the third unit 1052 with a straight trajectory 1101. The first step comprises calculating the arithmetic parameters relative to the global coordinate system for defining (i.e. making known) static or dynamic straight line that passes through (T) and points $C_A$ and $C_B$, referred to as "line $\{C_A/C_B\text{-}T\}(t)$", using 1) the coordinates $X_T(t)$, $Y_T(t)$, $Z_T(t)$ of the target point (T) substantially calculated relative to the global coordinate system from imaging or other same methods; 2) specific kinematic design of the robot, and in particular but not limited to the kinematic structure of the first unit 1050, as it is know by the design and construction of this robot, including the design presented later in this invention or any other third party robot that maneuvers an implement based on maneuvering of say two points $C_A$ and $C_B$ in space and/or 3) specific design and size of the port 1100, in particular but not limited to the say dimensions of the channel of the port that the say second unit 1051 and/or third unit 1052 via which the manipulator access the inside the body of the patient or animal or other structure.

The second step comprises calculating the updated coordinates of points $C_A$ and $C_B$ relative to the global coordinate system, i.e. $X_A(t)$, $Y_A(t)$, $Z_A(t)$ and $X_B(t)$, $Y_B(t)$, $Z_B(t)$, respectively, using the 1) specific kinematic design of the robot, and in particular but not limited to the kinematic structure of the first unit 1050, as it is know by the design and construction of this robot, including the design presented later in this invention or any other third party robot that maneuvers an implement based on maneuvering of say two points $C_A$ and $C_B$ in space and 2) the initial registration of the robot to the global coordinate system. The next two step comprise converting the updated calculated $C_A$ and $C_B$ coordinates to instructions for the further actuation of the actuated parts of first unit 1050 and supplying those instructions to the robot controller that further controls the actuators of the robot.

Figure 8A:
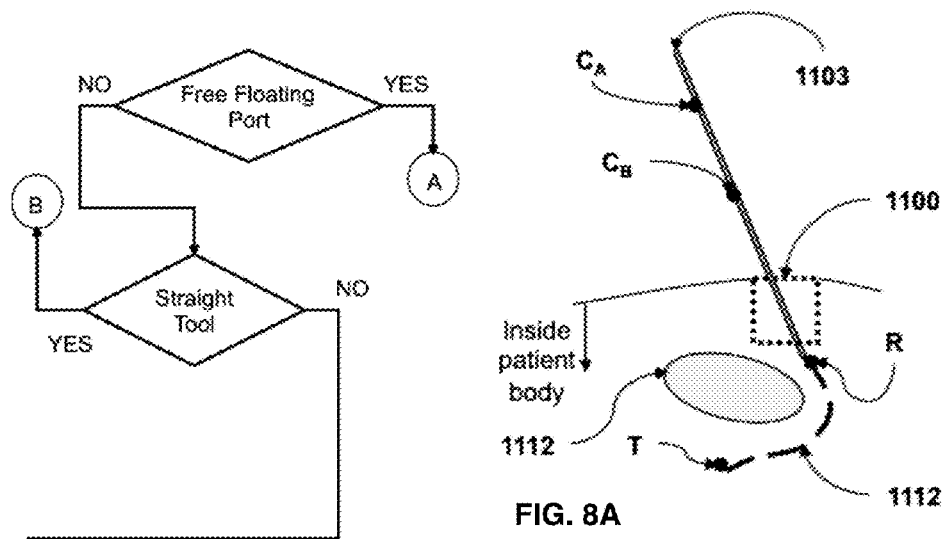
FIGS. 8A-8B: Schematics of operation for a robotic device.
Figure 8B:
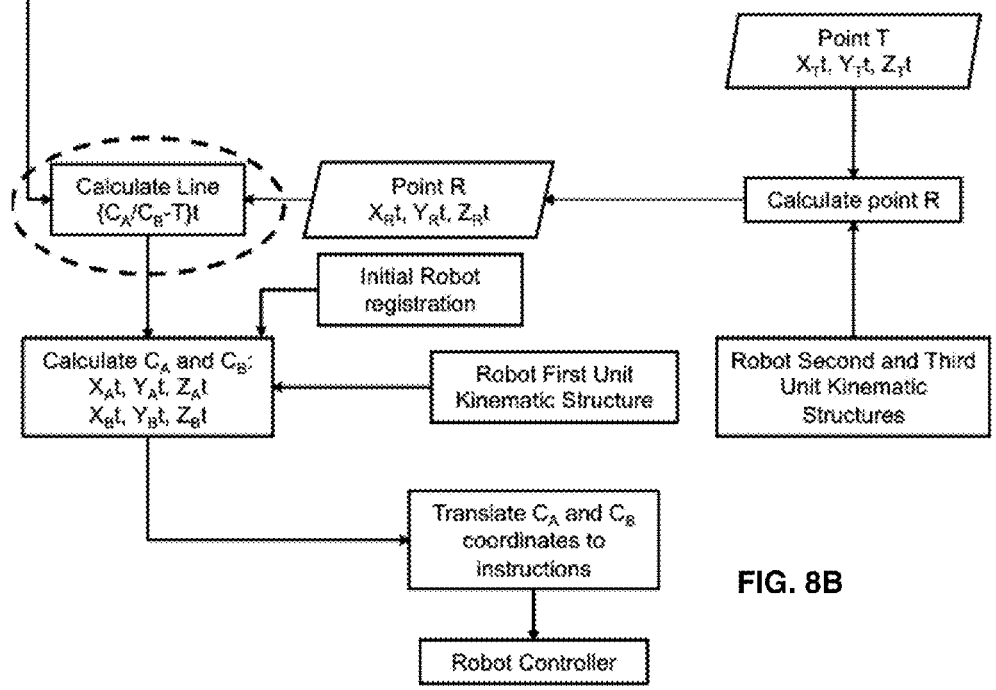

In yet another preferred embodiment and in reference to FIG. 8A, the second unit 1051 maneuvers a bendable./steerable third unit 1052 via a free floating (non-constraining) port 1100 to reach a target tissue (T) along a generally curved path 1112, as example to avoid object 1112, based on the flowchart in FIG. 8B composed of processes performed manually or preferentially in real-time, and on-the-fly, by the say computer or controller of the robot in order the third unit 1052 to follow the generally curved path 1112. The first step comprises substantially calculating the coordinates relative to the global coordinate system $X_R(t)$, $Y_R(t)$, $Z_R(t)$ of point (R) at the distal end of the second unit 1051, based on 1) the coordinates $X_T(t)$, $Y_T(t)$, $Z_T(t)$ of the target point (T) substantially calculated relative to the global coordinate system from imaging or other same methods; 2) the specific kinematic design of the robot, and in particular but not limited to the kinematic structure of the second unit 1050 and the bendable/steerable third unit 1053 as it is know by the design and construction of this robot, including the design presented later in this invention or any other third party robot posses the properties of a bendable/steerable tubular-like extension part; and 3) the specific design and size of the port 1100, in particular but not limited to the say dimensions of the channel of the port that the say second unit 1051 and/or third unit 1053 via which the manipulator access the inside the body of the patient or animal or other structure.

The second step comprises substantially calculating the arithmetic parameters for defining relative to the global coordinate system, i.e. making known, static or dynamic straight line that passes through (T) and points $C_A$ and $C_B$, referred to as "line $\{C_A/C_B\text{-}R\}(t)$", using 1) the coordinates $X_R(t)$, $Y_R(t)$, $Z_R(t)$ of the target point (R) substantially calculated relative to the global coordinate system from imaging or other same methods; 2) specific kinematic design of the robot, and in particular but not limited to the kinematic structure of the first unit 1050, as it is know by the design and construction of this robot, including the design presented later in this invention or any other third party robot that maneuvers an implement based on maneuvering of say two points $C_A$ and $C_B$ in space; and 3) the initial registration of the robot to the global coordinate system. The next two steps comprise converting the updated calculated $C_A$ and $C_B$ coordinates to instructions for the further actuation of the actuated parts of first unit 1050 and supplying those instructions to the robot controller that further controls the actuators of the robot.

Figure 9:
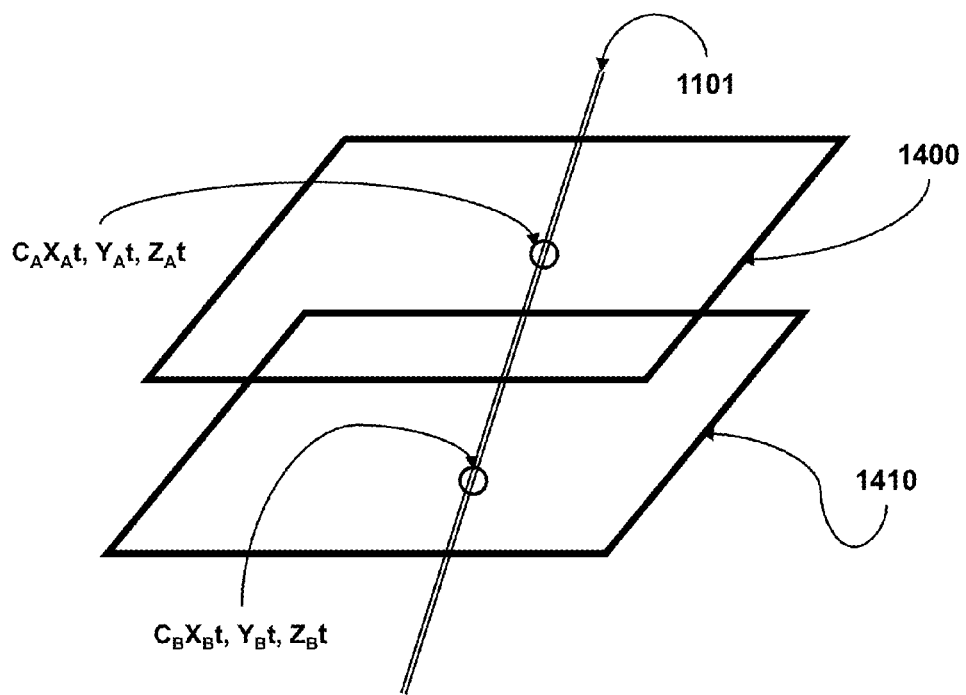
FIG. 9: Schematic of the two actuated points $C_A$ and $C_B$ of the robotic device.

In yet another preferred embodiment and in reference to FIG. 9, the actuated first unit 1050 is manufactured as a two parallel plane structure comprising a first parallelogram 1400 that contains mechanical means for the two-dimensional translation of point $C_A$ and a second parallelogram 1410 that contains mechanical means for the two-dimensional translation of point $C_B$. Preferably, the dual-stage robot is anchored onto a structure or frame, herein referred to as the "robot base", to provide positioning and orientation of the plane of the robot relative to the patient. This position and orientation is further determined by the specific needs of the interventional procedure as this is determined by, but not limited to, 1) the size of the patient, 2) the size of the interventional tool (applicator) that the robot will maneuver, 3) the location of the targeted anatomy, 4) the general direction of the access corridor or access path or access trajectory, and 5) other reasons known to those skilled in the art of surgery and interventional medicine. Anchoring also provides stability and rigidity for the robot as needed to perform the procedure Also in these preferred embodiments the robot base is a frame comprising 1) an interface that provides a preferred mechanical way to anchor the robot onto the "robot base", such as but not limited to means of screws or fasteners, 2) a preferred mechanical way for the robot base to be anchored onto the patient couch or the imaging scanner or onto the operating table on which the procedure is performed, 3) an alternative preferred way for the "robot base" to be anchored onto yet another base or frame that is laying on the floor of the room, and does not use any part of the imaging scanner or the operation table, and 4) an alternative preferred way for the "robot base" to be anchored onto yet another base or frame that is handing from the ceiling of the room, and does not use any part of the imaging scanner or the operation table. In addition, preferably, the robot base interface, onto which the robot is anchored, that is, set in position, as made during fabrication, or which is anchored in place by the operator relative to the patient to adjust the access workspace of the robot, this placement can be determined based on preoperative images or on the experience of the operator.

In addition, preferably, the robot base has a mobile interface onto which the robot is anchored and which can be manually and pre-operatively adjusted or manually re-adjusted during the procedure. That provides "global" adjustment of the position of the robot pre-operatively by the operator by means of vernier or plane sliding or angulation and securing to this position for the entirety or part of the procedure. Such adjustments comprise, but are not limited to orthogonal rails onto which the interface slides to adjust the relative position of the robot onto the plane of the interface and a rotation axis to adjust the angle of the interface, and thus the plane of the robot, relative. Alternatively, the robot base has a mobile interface, onto which the robot is anchored, that can be remotely actuated pre-operatively and manually re-adjusted intraoperatively by means of actuating a remote actuator during the procedure. That provides global adjustment of the position of the robot. Such adjustments are as described herein for manual adjustment.

Figure 10A:
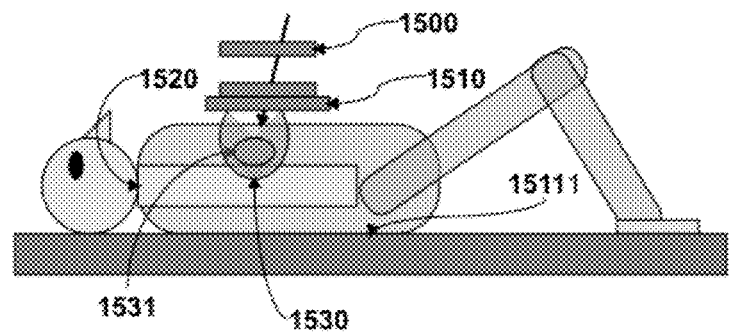
Figure 10B:
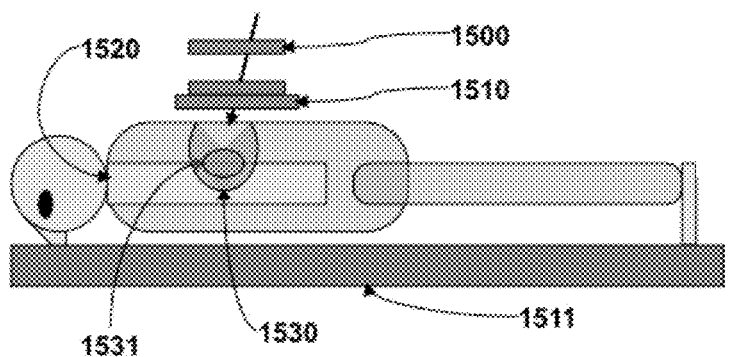
Figure 10C:
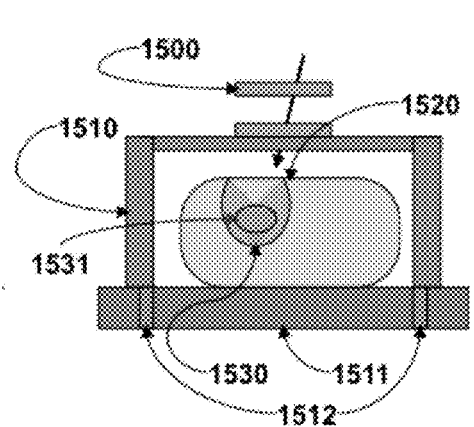
Figure 10D:
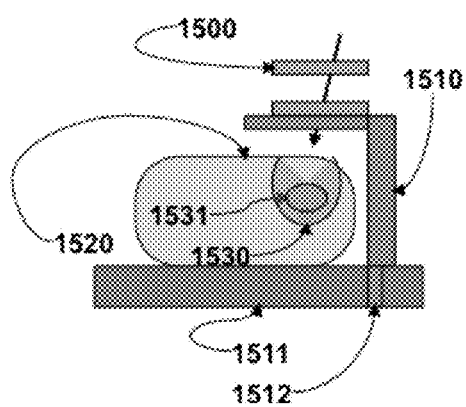

In yet another preferred embodiment and in reference to FIGS. 10A-10D, the flexibility of robotic platform to accommodate positioning of the patient is depicted. Generally, the patient 1520 may be positioned at a prone or supine position onto the operation table or imaging scanner couch 1511 and/or the robot 1100 may be anchored onto a base 1510 that substantially places the robot over the patient body in a way that the workspace 1530 of the robot substantially provides access to the targeted area of tissue 1531. In one aspect of this embodiment, as shown in FIGS. 10A-10B the patient 1520 is positioned at a prone or supine position onto the operation table or imaging scanner couch 1511, the robot base 1510 is anchored onto the operation table or imaging scanner couch 1511 by means of appropriate mechanical means 1512 that may include but not limited to, keys, fasteners and screws/bolds based on the particular design of the patient couch. In another aspect the patient 1520 is positioned at a prone or supine position onto the operation table or imaging scanner couch 1511, the robot base 1510 has the shape of a bridge, as shown in FIG. 10C, that goes over the entire width of the patient body and is stabilized by means of two legs or extensions of its structure with one on each side of the patient. In yet another aspect the patient 1520 is positioned at a prone or supine position onto the operation table or imaging scanner couch 1511, the robot base 1510 has the shape of a one-leg overhang over part of the patient body, as shown in FIG. 10D, and further this shape of robot base can be anchored to the left or the right of the patient side depending on the position of the targeted tissue 1531.

Figure 10E:
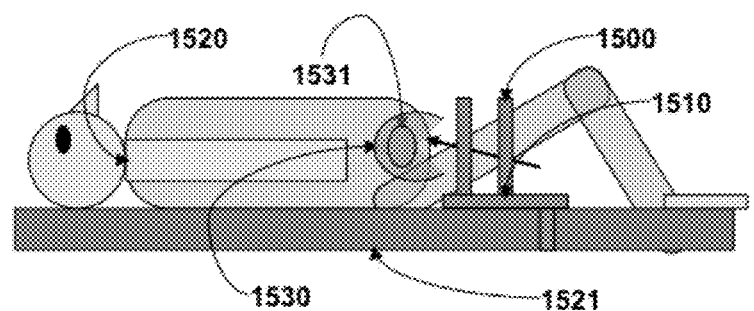
Figure 10F:
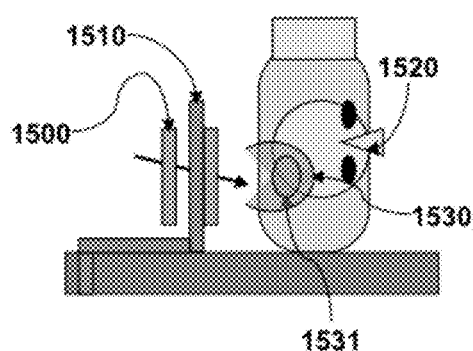
Figure 10G:
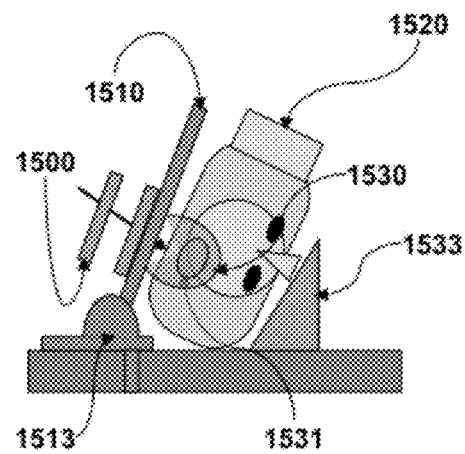

In this embodiment and in reference to FIGS. 10E-10M, further positions of the patient relative to the robotic device are depicted. In one aspect, as shown in FIG. 10E the patient 1520 is positioned in a supine or prone position onto the imaging scanner couch or operating table 1521 and the robotic device 1500 is orthogonally placed relative to the patient couch or operating table 1521 with a robot base 1510 manufactured such as the interface the robot anchors on places the robot at this orientation, and in a way the workspace 1530 of the robot assesses the pelvic area, for example for interventions in the prostate or cervix. In another aspect, as shown in FIG. 10F, the patient 1520 is laying on her/his side at an orthogonal orientation relative to the imaging scanner couch or operating table 1521 and the robotic device 1500 is orthogonally placed relative to the patient couch or operating table 1521 with a robot base 1510 manufactured such as the interface the robot anchors on places the robot at this orientation, and in a way the workspace 1130 of the robot assesses the patient at this position. In yet another aspect, as shown in FIG. 10G, the patient 1520 is laying on an angulated supine or prone position relative to the imaging scanner couch or operating table 1521, supported onto a wedged or otherwise appropriately shaped cushioned support 1533, and the robotic device 1500 is placed on an appropriate angle, selected by the operator based on the arts of surgery or interventional medicine, with a robot base 1510 manufactured with a mechanical assembly 1513 that allows angulation of the interface the robot anchors onto in a way the workspace 1530 of the robot assesses a particularly desired area of the patient that is better accessible or better revealed to access at this orientation of the patient.

Figure 10H:
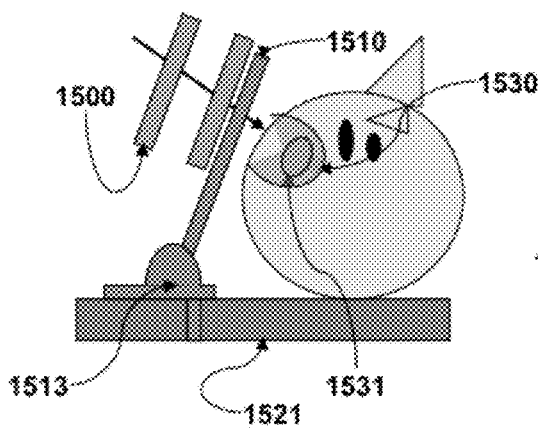
Figure 10I:
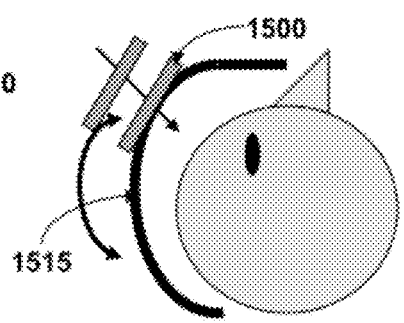

In yet another aspect, as shown in FIG. 10H, the patient 1520 is laying on a supine or prone position relative to the imaging scanner couch or operating table 1521, and the robotic device 1500 is placed on an appropriate angle, selected by the operator based on the arts of surgery or interventional medicine, with a robot base 1510 manufactured with a mechanical assembly 1513 that allows angulation of the interface the robot anchors onto in a way the workspace 1530 of the robot assesses a particularly desired area of the patient head for a neurosurgical procedure. In yet another aspect, as shown in FIG. 10I, the patient 1520 is laying on a supine or prone position relative to the imaging scanner couch or operating table 1521, and the robotic device 1500 is anchored onto the interface of a robot base 1515 that is manufactured providing an arched rail for the robot to globally positioned around the head of the patient in order to provide appropriate workspace for neurosurgical procedures. In yet another aspect, as shown in FIG. 10J, the patient 1520 is laying on a supine position relative to the imaging scanner couch or operating table 1521, and the robotic device 1500 is placed on an appropriate angle, selected by the operator based on the arts of surgery or interventional medicine, with a robot base 1510 manufactured with a mechanical assembly 1513 that allows angulation of the interface on which the robot anchors, in a way the workspace 1530 of the robot assesses the nasal cavity of the patient for trans-nasal operations, e.g., procedures to the pituitary gland.

In yet another aspect, as shown FIG. 10K and FIG. 10L, the patient 1520 is laying on a supine or prone position relative to the imaging scanner couch or operating table 1521, and the robotic device 1500 is anchored onto the interface of a robot base 1515 that is manufactured providing an arched rail for the robot for its global positioned around a part of the patient body that has a shape and anatomy such that requires a surrounding access and this part of the body is of a rather small size such as limps or shoulders for orthopedic procedures, such as arthroscopic procedures with image guidance. In yet another aspect, as shown in FIG. 10M, the robotic device 1500 is further used for procedure to the breast (as example biopsy, breast concerning therapy, etc.

Generally, in these embodiments and aspects the construction of the robot, robot base and any other component of the robotic system, based on the knowledge of those skilled in this art all material used is preferentially compatible and safe for use with the particular imaging modality. Also, material is selected to minimize friction between all surfaces or points that two objects that move relative to each other touch. In a non-limiting example, the contact surface of any parts that move relative to each other (there is low friction layer that can be permanent or re-applicable.

In yet another preferred embodiment and in reference to FIGS. 11A-11H, the two stage robot is reconfigurable and versatile in regard to the specifics of the actuated part. These configurations can be implemented at the level of are manufacturing where the customer acquires different sizes of the manipulator, depending on patient size, procedure etc. Also, these configurations can be implemented in the design of the manipulator and manufactured in a way that the operator (customer) can select them at-the-field (depending on patient size, procedure etc. These different configurations require different static or varying parameters in the software of control without necessarily requiring changing the kinematic equations. Those parameters can be loaded a priori by the manufacturer or selected by the operator depending on the selection at-the-field.

Figures 11A, 11B:
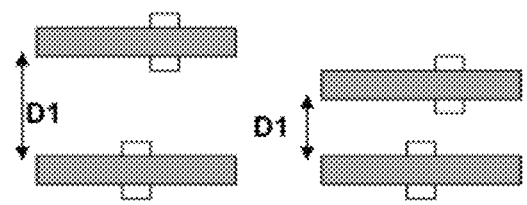
FIGS. 11A-11H: Schematics of reconfigurability and adaptability of the robot configuration.
Figures 11C, 11D:
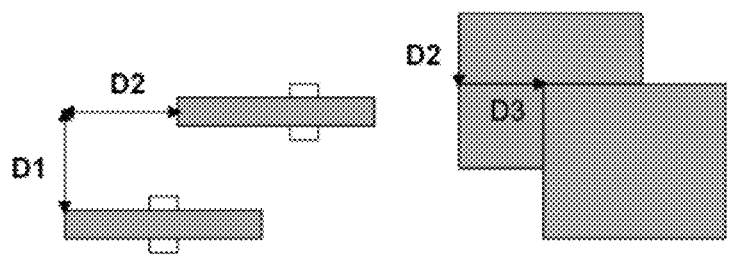
Figures 11E, 11F:
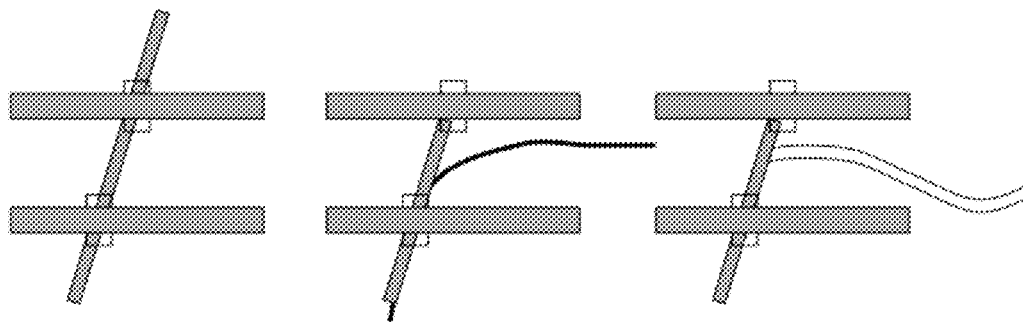
Figures 11G, 11H:

One reconfigurable option may be the distance between the two stages, as shown in FIG. 11A and FIG. 11B. Another reconfigurable option may be the relative position of the two stages which can be adjusted along one or two axis allowing for a wide range of offset angles, as shown in FIG. 11C and FIG. 11D. Yet other reconfigurable options may be that the interventional tool can be dispensed to transverse the planes of both stages, shown in FIG. FIG. 11E or may be limited between the two stages as shown in FIG. 11F. Yet more reconfigurable options, as shown in FIG. 11G and FIG. 11H, may be that the length of the stages can be produced in different sizes as to accommodate wider or narrower workspace and/or reduce the size of the manipulator. These reconfigurations and any other conceivable shape and/or size altering actions for reconfiguring the manipulator in-the-field, can further be performed manually preoperatively and, in this instance, certain options can be selected, or can e performed intraoperatively using additional remote actuation lines.

In yet another preferred embodiment and in reference to FIGS. 12A-12D, and with particular reference to when the imaging modality is magnetic resonance imaging (MRI), appropriate arrangements for the radiofrequency (RF) coil with respect to the manipulator can be made to further enhance the quality of the MR images. These arrangement include consideration of the size, positions, or combination of RF coils or any other means. Those RF coil arrangements are used to improve the sensitivity of signal reception and resultant improvement of the SNR of the MR images and in particular in the area of the procedure secondary to proximity and to locally deliver RF power, in the for of pulse or pulse sequences of RF pulses, for selective manipulation of the magnetization of the tissue at the area or at the proximity of the area of the procedure, as example but not limited to signal suppression for FOV reduction, bands for tracking motion or other such applications.

Figure 12A:
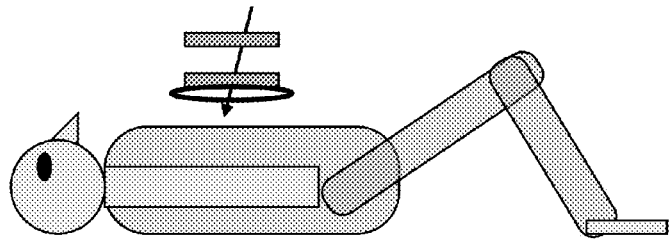
FIGS. 12A-12D: Incorporation of RF coils with the robot.
Figure 12B:
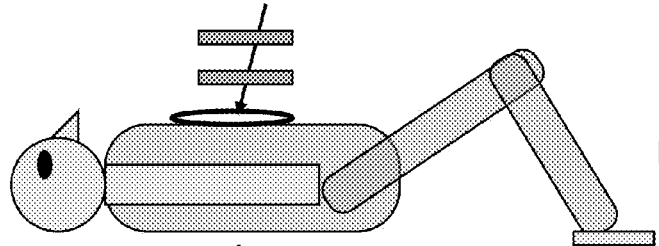
Figure 12C:
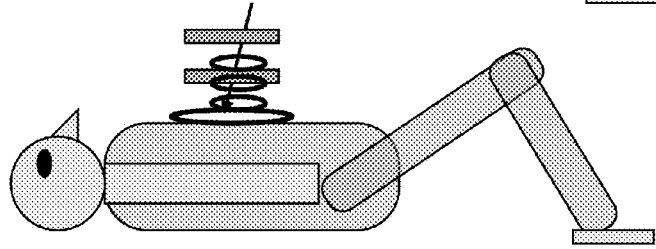
Figure 12D:
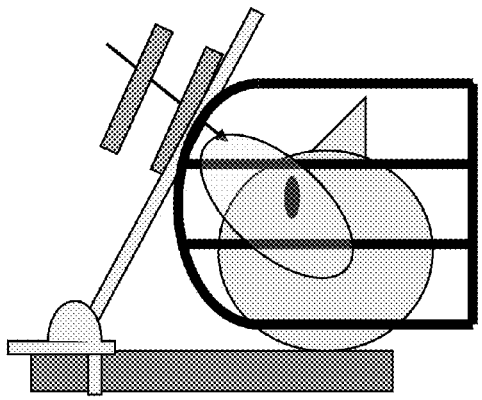

In one aspect of this preferred embodiment, as shown in FIG. 12A, the RF coil is attached onto the base of the robot and at a set position relative to the patient's body. Alternatively, the RF coil is attached onto the moving part of the robot and preferentially onto its second Unit and being mobile relative to the patient's body. In another aspect, as shown in FIG. 12B, the RF coil is attached onto the patient or on both sides one or more RF coils for improving the SNR locally at the area where the operation is performed. In yet another aspect, as shown in FIG. 12C, there are plurality of RF coils sets, with one set preferentially placed onto the body of the patient and another set preferentially placed onto the manipulator. In this aspect the two sets can be implemented as two independent coil sets, i.e. each set is connected to separate dedicated RF channel on the MR scanner. Furthermore, the two RF coil sets are used for collecting one image or complementary images from each set in an alternating manner. For this case the two images can be superimposed or farther processed by means known to the art in order to fuse them together. Alternatively, the two sets can be implemented as a single RF coil unit. In yet another aspect, as shown in FIG. 12D, the manipulator can further be used with current commercial RF coils using appropriate software of this invention that maps the available access via the openings of the commercial coil and for this particular robot. Thus, the robot will have even a wider range of applicability.

In yet another preferred embodiment of this invention the software of the robotic manipulator further includes a software module dedicated to pre-operative analysis for the selection of the type of base 1510 and the determination of the position of base relative to the patient's body so that the workspace 1530 of the robotic manipulator is substantially placed as to include the targeted area 1531. This takes into consideration the anatomy of the area of the intervention, the dynamic motion of the tissue at the area of the intervention and the constraints of the robotic manipulation motion secondary to its specific kinematic characteristics.

Figure 13:
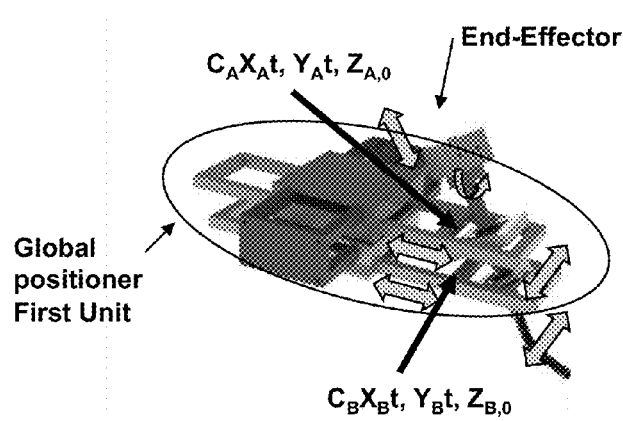
FIG. 13: Illustrates the orthogonal Cartesian state of the robotic manipulator.

Exemplary of all these preferred embodiments and with reference to FIG. 13, a robotic manipulator compatible with magnetic resonance imaging is depicted and demonstrates that the robotic manipulator operates as a two parallel dual-axes orthogonal Cartesian stage with multiple degrees of freedom (DoF), as shown to scale. can be placed at any orientation relative to the coordinate system of the MR scanner to better fit to a particular procedure. The robotic manipulator may be constructed from non-metallic and conductive material, such as, titanium carbon reinforced composites, fiberglass and plastics. The device is designed to be utilized with image-guided endoscopic surgeries or other Single Port Access surgeries.

Figures 14A, 14B:
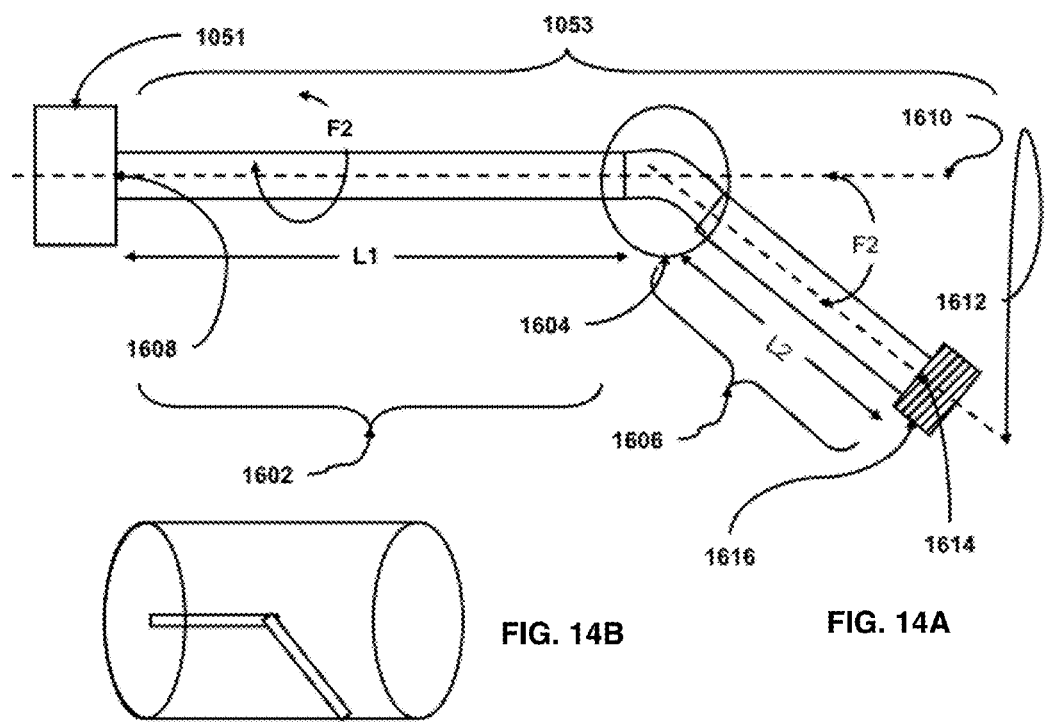

In yet another preferred embodiment and in reference to FIGS. 14A-14D, the third Unit of the robot 1053 is bendable to reach the target area. Alternative means of generating the bending may comprise tubes with angulated slider, a rigid flexion regulator or pre-bend elements. In one aspect of this embodiment, as shown in FIG. 14A, the third unit 1053 is composed of three parts in tandem: 1) the first straight part 1602 one that extends from the distal tip 1608 of the second unit 1501 of the robot and has a length L1 measured relative to point 1608, 2) the second bendable part 1604 that bends by an angle F1 defined as the angle of intersection of the long axis 1610 of first part 1602 and the axis 1612 of the third part 1606, and 3) the third straight part 1606 that has a length L2. Furthermore, the third unit 1053 has a plurality of components that are independently actuated to adjust 1) the length L1 of the first straight part 1602, 2) the degree of bending F1, 3) the length L2 of the third straight part 1606, and 4) the rotation F2 of the entire third unit around axis 1610. In another aspect, as shown in FIG. 14B, those four actuated entities define four degree-of-freedom DoF that allow for the tip 1614 of the third unit to reach any point on a cylinder, thereby delivering and positioning an interventional tool or therapeutic element, such as a prosthetic valve or an applicator, (616 to the targeted area or tissue.

Figure 14C:
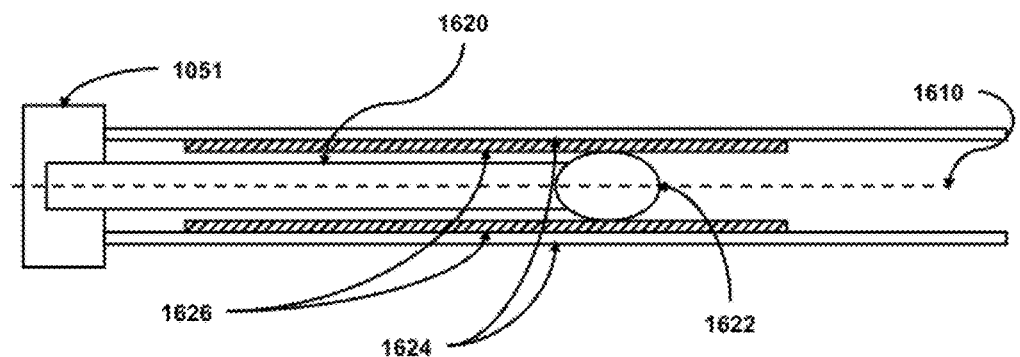

In yet another aspect and in reference to FIG. 14C, the third unit 1053 is composed of a component 1620 that is substantially more rigid than its other components and its axial motion along axis 1610 defines length L1 that substantially corresponds to the portion that the bending occurs along the long axis of the third unit. At its distal tip, component 1620 further carries another component 1622, which it will be referred to as the "flexion" element, which has mechanical or by other means actuated elements for inducing a bending or angulation relative to the axis 1610. The flexion element further bends the outside sheath 1624 of the third unit directly or by first bending a shorter sleeve 1626. The outside sleeve further is translated along its long axis and as it extends defines the length L2.

In yet another aspect and in reference to FIG. 14D, the flexion element is composed of a pre-bent element that controllably extends to define the degree and extend of bending. In yet another aspect and in reference to FIG. 14E, the flexion element is composed of a single-string pull arrangement that when pulled by an actuator induces controllable degree and extent of bending. In yet another aspect and in reference to FIG. 14F, the flexion element is composed of two cylinders that are cut at an angled way and they rotate one relative to each other as to induce controllable degree and extent of bending.

In yet another preferred embodiment there is provided a remote actuator for robotic manipulators and means for remote actuation. Remote actuation describes the arrangement with which the power to actuate the robot is generated remotely from the robot and then transferred from this site to the robot via "actuation lines". This power can be provided to the actuation lines from computer- or electronic-controlled actuators that require the input of from an energy source, such as electric power, and examples include, but not limited to, electromagnetic or piezoelectric or hydraulic or pneumatic or any other type of actuator or manually, by the manual power of the operator.

As used herein, "rigid-liquid" refers to a remote actuator. The rigid-liquid is a central aspect of this invention and is based on the operation principal of a hydraulic or pneumatic actuation and transmission systems in which the liquid or gas is substituted with rigid elements, such as, but not limited to, spheres and pistons and any combination thereof. The term "container tube/tubing" describes the tubes that provide the conduits in which the "rigid-liquid" moves. The term "actuation line(s)" describes the link between the power source and the robot to transmit actuation. Preferably, the robotic manipulator is remotely actuated by means of an actuator, such as, but not limited to an electromagnetic motor (EMM) that is at a distance from the robotic manipulator and actuation is transmitted by means of a plurality of transmission lines or, as herein referred to as actuation lines or actuation transmission lines. At least one transmission line is configured for actuation of one degree of freedom of the robotic manipulator or robot.

In this preferred embodiment and in reference to FIG. 15, the entirety of the actuation lines or a portion thereof resemble a conventional hydraulic or pneumatic system, in that it is composed of a controlled actuator 2301 that is actuating, in generally, a remotely located applicator 2302, by means of displacing a medium that occupies the space inside, tubing 2303, i.e. a hose that connects the actuator 2301 and the applicator 2302. The actuation lines can be entirely or partly flexible, rigid or can be a combination of rigid and flexible parts.

In yet another preferred embodiment of this invention and in reference to FIG. 16A, the displaceable medium comprises a series of spheres 2306 that fill the space inside the tubing or container tubing 2305 and are contained by means of two piston-like plugs, one 2307 at the proximal end of the actuator 2301 and the other 2308 at the distal end of the applicator 2302. The actuator 2301 translates the piston-like plug 2307, which in turn pushes and advances within the container tubing 2305 the plurality of spheres 2306, which in turn are displaced and further linearly displace the distal piston-like plug 2308, which in turn provides remote linear actuation at the distal end of the applicator 2302. Also, the radius Rsphere of the spheres as, compared to the inside or inner diameter ID Rtube of the container tubing 2305 is Rtube/2<=Rsphere<Rtube. Alternatively, Rsphere≈(but less) Rtube, as shown in FIG. 16B and FIG. 16C.

In this preferred embodiment of the invention and in reference to FIG. 16B and FIG. 16C, a ring or washer with an outside diameter (OD) Rring, 2310 and 2312, is placed between two adjacent spheres or one or more pairs of adjacent spheres. Preferably, this is implemented to eliminate, for example, but not limited to, the necessity of keeping the spheres centered, may eliminate friction forces between adjunct spheres, that can drive the spheres in opposite directions, and may eliminate friction between the spheres and the inside wall of the container tube 2305, as shown in FIG. 16C. The rings or washers may have a lateral internal diameter (ID) that keeps the spheres at a certain distance with a gap 2312 preventing them from rubbing each other.

In one aspect, as shown in FIG. 16B, the diameter Rring of the rings or washers 2310 is smaller than the ID of the containing tube Rring<Rtube. In another aspect, as shown in FIG. 16C, the outer diameter Rring of the rings or washers 2311 is slightly less than the ID of the container tube, i.e., Rring≈(but less) Rtube. In these preferred embodiments to the actuator, the actuation lines are constructed, based on knowledge of those skilled in this art. Particularly, all material used is preferentially compatible and safe for use with the particular imaging modality. Also, material is selected to minimize friction between all surfaces or points that two objects move relative to each other touch. In an non-limiting the inside surface of the container tubing maybe have low friction to the spheres or rings/washers or pistons as result of (i) the material the containing tubing is constructed in its entirety and/or (ii) the presence of a low friction layer that can be permanent or re-applicable.

Preferably, the spheres 2306 made of rigid, non-compressible, non-elastic, material as example, but not limited to, glass, high strength polymers, reinforced polymers, composites, stainless steal etc. The material of the spheres 2306, rings/washers 2310,2311, the container tubing 2305, or its internal surface when a layer is applied, are preferentially selected from among materials known in the art so that their relative frictions are minimized.

According to another embodiment, and in reference to FIG. 16D, a string or flexible wiring 2316 may pass through a channel made inside the spheres and along their lateral diameters allowing the implementation of a push-pull action line. In an aspect of this embodiment, the string or wire is anchored at its distal end.

Also, in these preferred embodiments of the invention and in reference to FIGS. 16E-16F representative parameters of the tubing 2305, spheres 2306, and rings, washers or bushings 2310 or 2311 components required for manufacture of the transmission line 2300 are illustrated. In FIG. 16E the transmission line, comprising the tubing, spheres, bushings, has a length LL. Each representative sphere has a diameter SpD and the tubing has an inner diameter TubD or ID Rtube as referenced in FIG. 16A. A representative bushing has a length BhL between spheres and an inner diameter BhD. These parameters also influence the performance of the line with respect to the degree of friction, delivered force, bandwidth of operation, and linearity. A clearance may be required so that SpD<TuD and to maintain alignment of the spheres. Reducing the number of spheres to reduce friction, the bushing length BhL may be increased. Longer bushings further reduce friction and increase efficiency of transmission.

Preferably, the tubing is made of flexible, non-expandable, i.e., does not change diameter under transverse forces, and axially non-stretched material. The latter two properties are important to maintaining linearity and non-compressibility of the lines. As such and with reference to the cross-sectional view in FIG. 16F, the tubing 2305 may further comprise an internal sleeve-like component 2317 that provides lubrication and an external sleeve 2319 that provides stiffness along the transverse plane, which is non-expandable. The external sleeve may comprise standard or modified materials and manufactured similarly to the pneumatic or hydraulic lines.

Figure 17A:
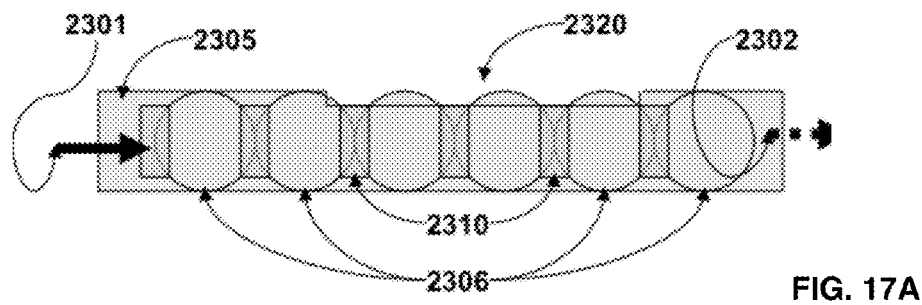
Figure 17B:
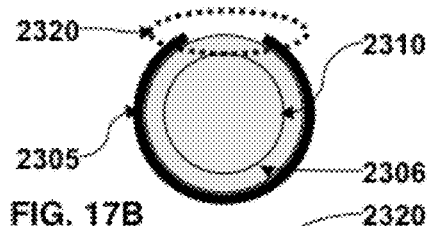
Figure 17C:
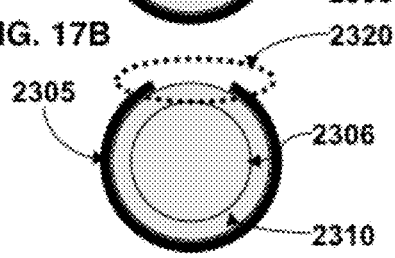

In yet another preferred embodiment of this invention and in reference to FIGS. 17A-17G the container tube may comprise openings and a key/link. The container tube 2305, as shown in FIG. 17A, has one or a plurality of openings 2320 that has an arc that is appropriately selected to be "small" enough as to (i) prevent the spheres 2306 and the rings/washers 2310 from falling out of it, and (ii) does not affect in anyway, such as dislocating the alignment, the translation motion of the rigid-liquid. In alternative aspects there may be a cut through the actuation line with an opening 2320 when the Rsphere is larger than the Rring, as shown in FIG. 17B, and when the Rsphere is smaller than the Rring, as shown in FIG. 17C. The "rigid-liquid" method provides a unique benefit, particularly as compared to traditional pneumatic and/or hydraulic actuators, of introducing by appropriate mechanical manufacturing practices known in the art, one or a plurality of openings 2320 along the length of the container tube to transfer actuation This property offers unique design and manufacturing capabilities for implementing actuation.

A piece/part 2325, herein referred to as the key/link and having a plug-like configuration extends outside the opening 2320 and further is part of block 2326 that moves inside the container tube 2305, as shown in FIG. 17D, or is an extension of one or a plurality of ring/washer 2327, as shown in FIG. 17E, in a way that as the "rigid-liquid" advances inside the container tube 2305 it translates the block 2326 and/or the ring/washer 2327, and as a result translates the key/link 2325 along the axis of the actuation line and in synchrony with the rigid-liquid. Preferably, the key/link 2325 is linked to an implement 2328, which preferentially resides outside the container tube/actuation line, and translates parallel to the actuation line and in synchrony to the motion of the rigid-fluid motion inside the container tube/actuation line.

Figure 17F:
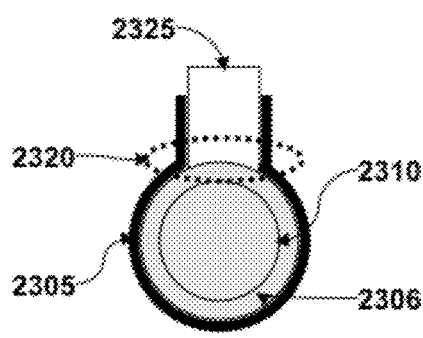
Figure 17G:
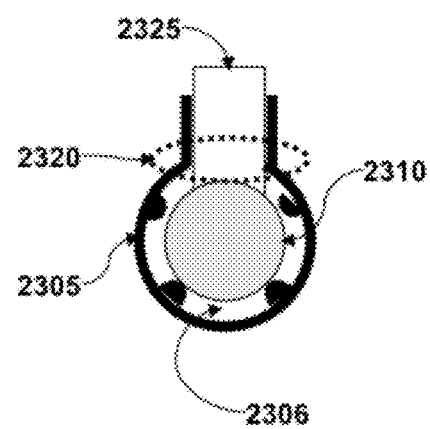

The actuated implement 2328 slides on rails that may or may not relate to the motion of the rigid-liquid. As shown in FIG. 17F, the actuated implement 2328 is, or it is linked to, 1) the applicator of the robotic manipulator and provides translation of this applicator along the linear DoF, 2) the mechanical structure of one of the DoF of the applicator of the robotic manipulator and provides translation along this axis, 3) the moving element of a position encoder for measuring the exact translation caused by the actuation, 4) the moving element of any form of position measuring device, for example but not limited to the reflective element of a light based measuring device, for measuring the exact translation caused by the actuation, 5) a fiducial marker compatible to the uses imaging modality thereby allowing monitoring the motion of this particular point in space, and 6) any other type of applicator or device that needs to translate in synchrony to the "rigid-fluid" for any purpose. The actuated implement 2328 is linked to a mechanical assembly for converting translation actuation, provided by the actuation line, to other type of motions such as but not limited to rotational or translational vertical or to an angle relative to the axis of translation of the actuation line. The block 2326 that moves inside the container tube 2305 and carries the "key/link" 2325 can be alternatively implemented to be smaller than the ID of the container tube 2305 and slides onto a plurality of rails 2330 that extend along its traveling length, as shown in FIG. 17G

Figure 18A:
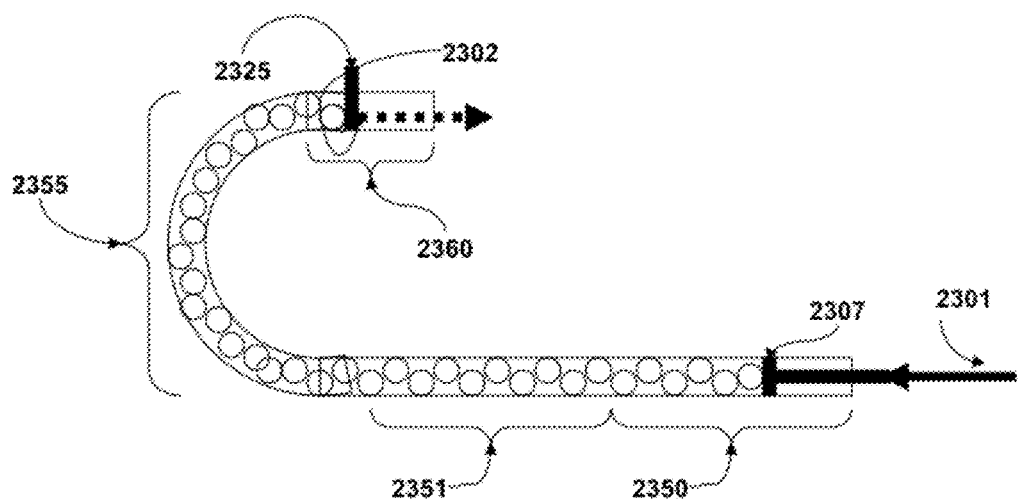
FIGS. 18A-18B: Depicts configurations of the hose, which can be rigid or flexible or any combination of rigid and flexible hoses.

In yet another preferred embodiment of this invention and in reference to FIGS. 18A-18B and FIGS. 19A-19B, the container tubing has one or more portion(s) that is (are) rigid or solid, i.e. not-flexible and may comprise the rigid-liquid as spheres and/or may comprise pistons. For example, the container tubing may be flexible container tubing with spheres, rigid container tubing with spheres or rigid container tubing with piston. In this embodiment, as shown in FIG. 18A, rigid container tubing together with a flexible tubing 2355 is used preferably at the various areas of the actuation line. In non-limiting examples the combination of tubing may be used 1) at the proximal end 2350 of the line where the actuation piston assembly 2307 is located, 2) at the distal end 2360 of the line where the delivery piston or "key/link" assembly 2325 is located, 3) at any part of the actuation line that does not need to be flexible 2351, and preferentially transverses long straight zones or predefined non-straight ones or 4) at any part of the actuation line that for any reason is used for delivering actuation or for monitoring the operation of the line as discussed in the previous embodiment pertinent to the application of the key/link 2315.

Figure 18B:
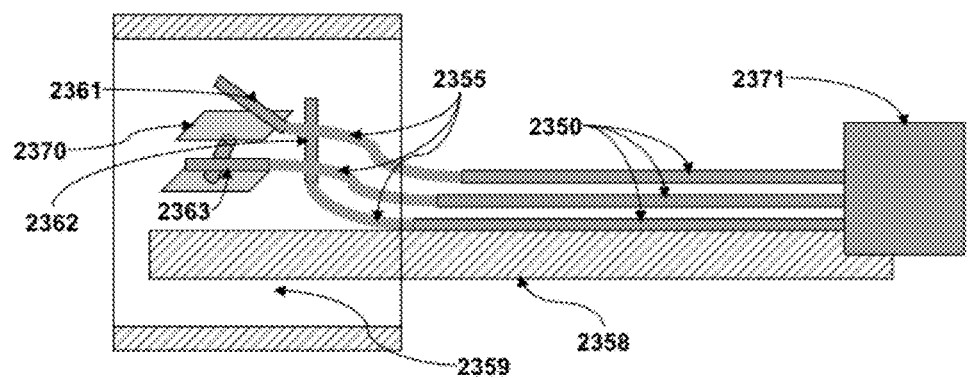

Also, as shown in FIG. 18B, the implementation of a plurality of actuation lines to actuate the plurality of the DoF of a robotic manipulator 2370 that resides inside the bore 2359 is based on several features. Implementation is based on a plurality of straight and rigid container tubes that extend from the site of the actuators 2371 to the proximity of the robotic manipulator 2370 and those tubes are preferentially compacted, packed and secured onto the patient couch 2358 of the imaging scanner. Also, the distal-ends of the plurality of the above mentioned straight and rigid portions of the actuation lines, i.e. the ends at the proximity of the robotic manipulator, are connected to a corresponding plurality of flexible container tubes 2355 that their distal ends are further anchored onto the moving portions of the DoF of the robotic manipulator 2370. In addition, the distal ends of the plurality of the flexible container tubes 2355 are further connected to a plurality of rigid container tubes 2361, 2362, 2363 that contain the actuation unit for the corresponding DoF of the robotic manipulator.

Figure 19A:
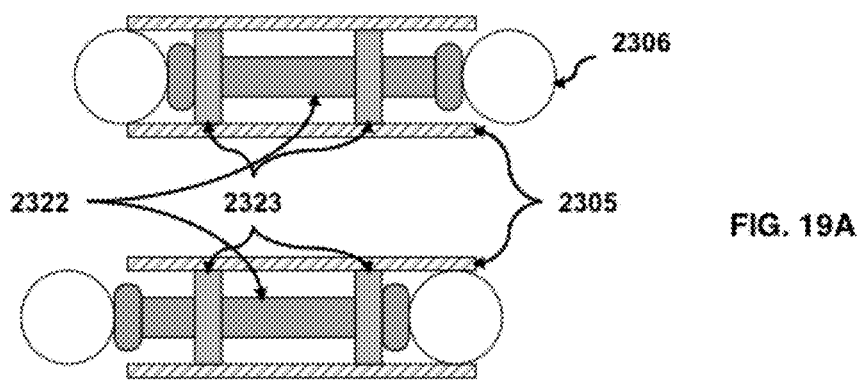

In yet another preferred embodiment of this invention and in reference to FIG. 19A, the spheres in any straight portion of the tubing can be substituted with a piston 2321 that rides linearly along the axis of the tubing 2305, comprising of 1) a rigid tube 2322 that its length is at least the length of the piston plus the distance required for the actuation of the corresponding DoF, 2) a piston constructed of appropriate material to minimize bending or any flexion of its body, 3) a plurality of bearings 2323 along the length and attached onto the tubing for low-friction linear motion of the piston, as well as support of the piston body to further eliminate any flexion of the piston. This implementation is in particularly beneficial for reducing friction. According to this embodiment, the plurality of the straight actuation lines 2350 in FIG. 18B may have such pistons instead of spheres.

Figure 19B:
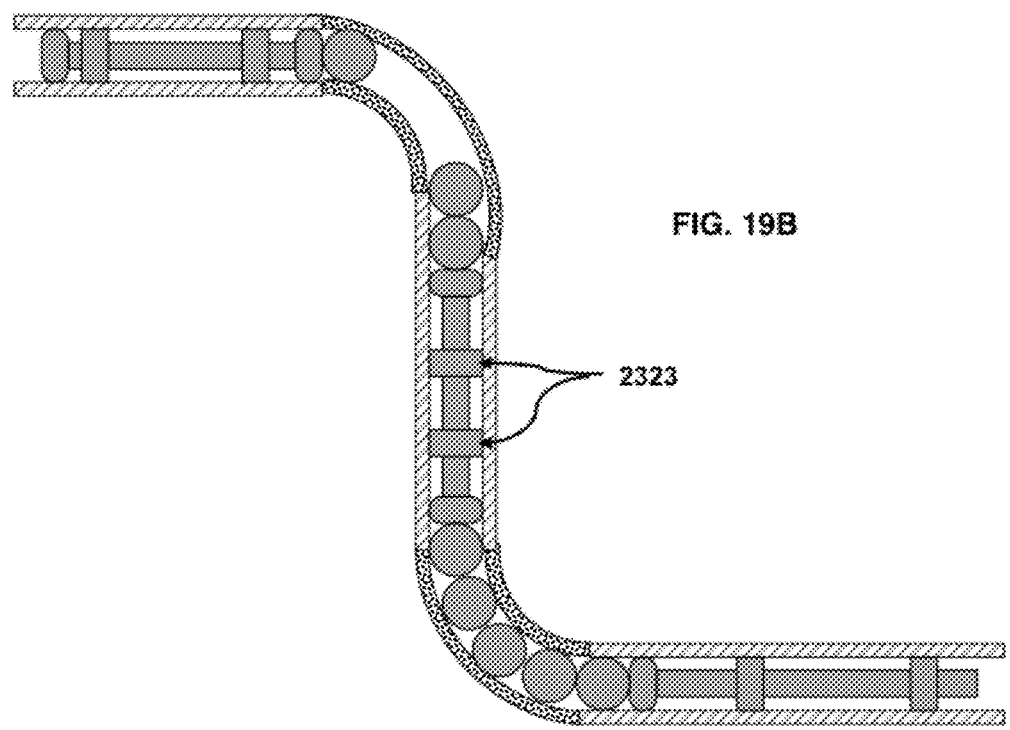

According to this embodiment, FIG. 19B illustrates example of such actuation line with a combination of flexible tubing 2305 with spheres and rigid straight tubing 2305 with pistons 2321. In this case the actuation comprises, starting from the proximal end, 1) a computer-controlled motorized or manual powered actuation mechanism, 2) a piston assembly that is anchored onto the actuation mechanism at its one end, 3) a piston assembly that is long and transverses the distance from the actuation mechanism to the center of the imaging scanner where the area of the patient is located to perform the procedure, 4) an other end of the piston that enters into a rigid container tubing or segment thereof, 5) the rigid container tubing attached to a flexible container tubing or a segment thereof of the same ID, 6) the distal end of the flexible container tubing is attached to another rigid tubing of the same ID, and 7) the first rigid, the flexible and the second rigid container tubing filled with actuation spheres. Also, multiple such set ups are combined and axially deployed to actuate multiple degrees of freedom of an actuated manipulator to perform a medical intervention or other procedure that need actuation, such as, but not limited to the movement of another modality probe.

FIGS. 19C-19E illustrate preferred implementations of the robotic device and its actuation with the rigid liquid transmission lines 2300 comprised of 1) a plurality of rigid tubes 2322 with pistons 2321 that extend from the power unit 2324, to the vicinity of the actuated parts of the robot on the robot base 1510, 2) a plurality of flexible tubes filled with spheres and bushings that continue the transmission path from the distal end of the rigid tubes to the robot. The rigid tubes/piston combinations are used for the portion of the actuation lines that are not moving and the flexible tubes are used to the portion of the line that needs to move or flex or bend in order to transmit actuation to the actuated, and thus moving parts, of the robot. FIG. 19C illustrates the motor disposed on the end of patient couch 2358, FIG. 19D illustrates the motor placed behind the wall of an MR scanner room 2321 where the wiring passes through the scanner room wall via an appropriate conduit such as a waveguide 2332 and FIG. 19E illustrates a manually operated motor disposed on the side edge of the patient couch.

Figure 20E:
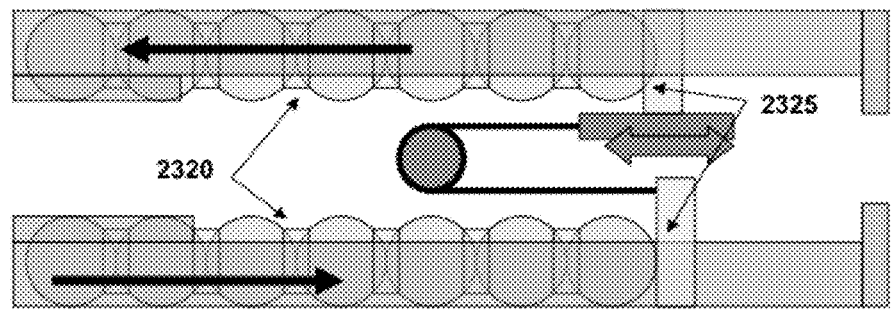
Figure 20F:
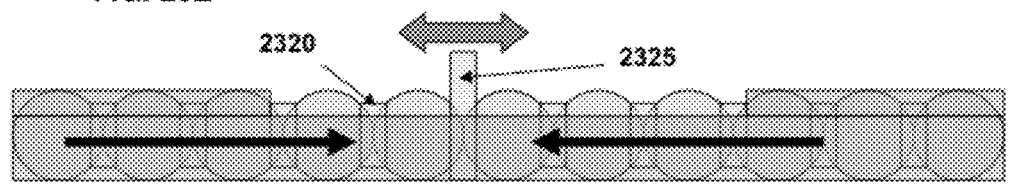
Figure 20G:
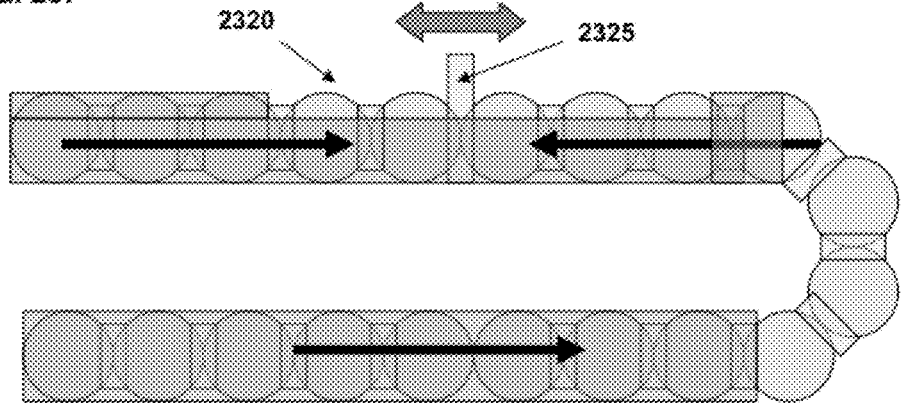

In these embodiments and in reference to FIGS. 20A-20H examples of linking the "rigid liquid" actuation lines to the actuated components are shown. The key link 2325 can be linked to an actuated implement 2328 through the one or a plurality of openings 2320 in the rigid liquid actuation lines. In one aspect, as shown in FIG. 20A, the key link and actuated component are linked for linear actuation without return. In another aspect, as shown in FIG. 20B, the linkage enables linear actuation with return with a resisting or loaded spring 2380. In yet another aspect, as shown in FIG. 20C, the linkage enables a conversion of linear to rotational actuation and vise versa via a rack-and-pinion actuated component. In yet another aspect, as shown in FIG. 20D, the linkage enables a conversion of linear to rotational actuation and vise versa via a lever actuated component. In yet another aspect, as shown in FIG. 20E, the linkage enables a conversion of linear to rotational actuation and vise versa via a timing-belt chain actuated component. In these aspects, as shown by the arrows, rotation is achieved either by pushing in the same direction or by pushing together from opposite direction. In yet another aspect, as shown in FIG. 20F and FIG. 20G, actuation of the implement is via bi-directional linear actuation.

Figure 20H:
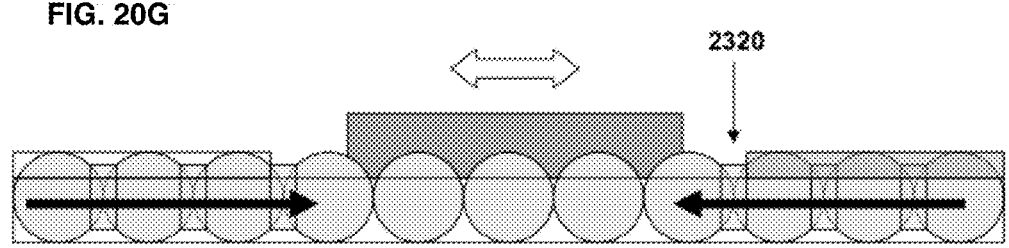

According to this embodiment the path of the transmission line can be embedded into the structure of the robot as shown in FIG. 20H. The double-headed arrows show that the path of the transmission line, represented by a structure or component that is embedded into the robot structure, into the spheres are translating and entering and existing at the same position of the device. This has the benefit of directing the transmission line to enter and exit from the same site of the robot to further facilitate compactness and functionality in its deployment. Moreover the link or structure or component can further engage directly onto the spheres with an appropriate shaping of the interface. For example, the link itself can separate the spheres.

Figure 21C:
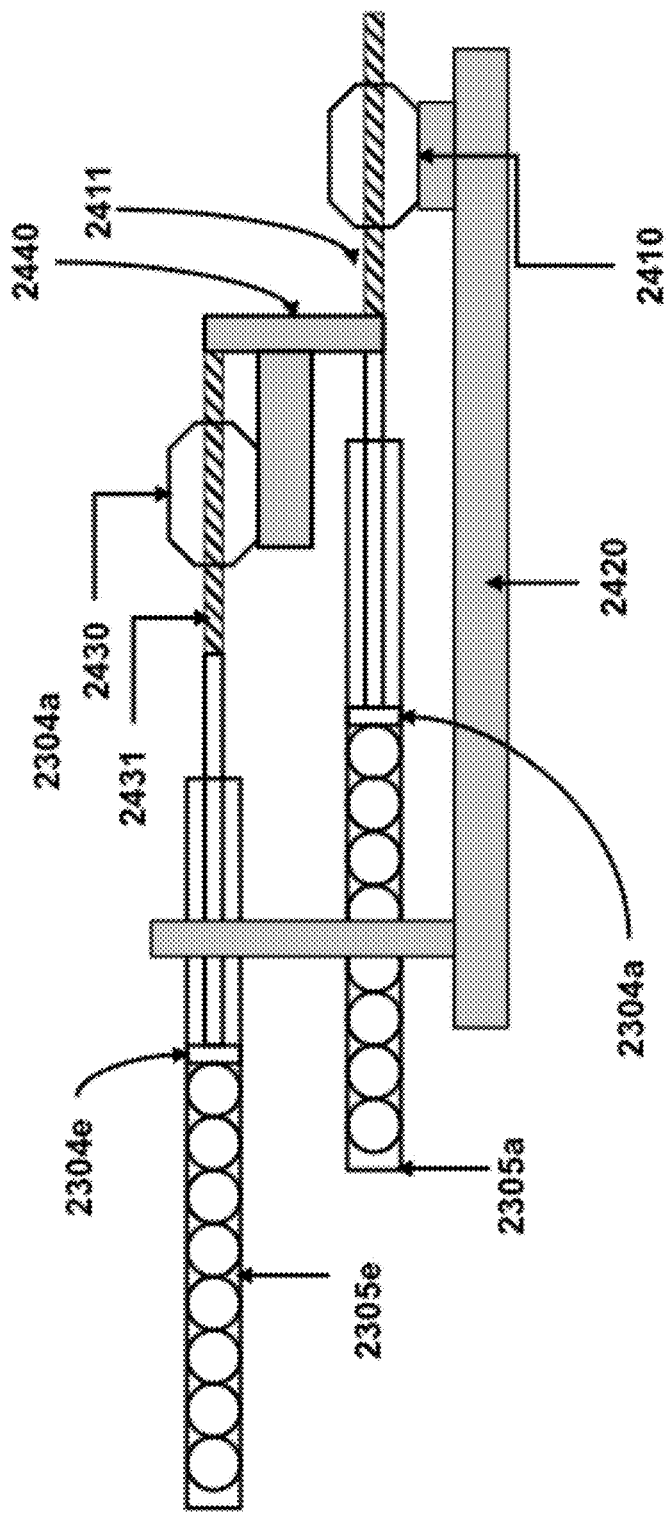

In yet another preferred embodiment and in reference to FIGS. 21A-21C, methods for actuating multiple lines of rigid liquid lines are depicted. A general set-up for linear actuation of two lines is shown in FIG. 21A. A linear motor 2410 with a motor screw 2411 is linearly coupled to actuation pistons 2304a,b. The actuation pistons are movably disposed within container tubes 2305 comprising the rigid-liquid actuation spheres 2306. The linear motor and container tubes are supported by base 2420. The minimum tube length is equal to the stroke of the piston. The container tube can be any combination of rigid or flexible tubing. The pistons move linearly along the tube in a reciprocal motion, as shown by the block arrows, to actuate the rigid-liquid assembly.

FIG. 21B depicts the set-up of FIG. 21A except that two pairs of two pistons 2304a,b,c,d are linearly coupled to the motor screw 2411, via couplers 2412a,b, comprising the linear motor 2410. Each pair of pistons moves uniformly and linearly in a reciprocal motion along the respective tubes, as shown by the block arrows, during actuation.

FIG. 21C depicts coupled multi-degrees of freedom actuation. Base 2420 supports the first linear motor 2410, motor screw 2411, piston 2304a, and tube 2305a configuration as in FIG. 21A. Base 2420 also supports a second tube 2305e at its distal end. A second base 2440 supports a second linear motor 2430, motor screw 2431 and piston 2304e, disposed within the second tube 2305e. The second base 2440 is moved by the first linear motor 2410 while the second linear motor 2430 moves the piston 2305e. Thus, the first linear motor actuates the first piston 2305a and, because it moves the second base 2440, the second piston 2305e also is moved, thereby providing coupled actuation.

In yet another preferred embodiment powered actuation can be done, but not limited to, a plurality of electric motors unmodified or modified (1-2). If the guidance modality is MRI, an unmodified motor and its wiring may need to be enclosed into appropriate electromagnetic shielding to eliminate electromagnetic interference. Moreover, if the motors are manufactured of ferromagnetic or paramagnetic materials must be anchored to prevent their unwanted movement due to the magnetic field of the MRI scanner. A modified electric motor, may be specifically manufactured by non ferromagnetic or paramagnetic materials and in addition without a permanent magnet, rather using the magnetic field of the MRI scanner. At this case, the exact performance, e.g. torque and rotational speed, of the motor(s) will depend on the strength of the main magnetic field $B_O$ of the MR scanner at the particular position of the motor(s).

In the case of specially made motors, they are equipped with 1) a Hall probe to measure the magnetic field at the exact location of the motor, and 2) a sensors of rotational speed, for example, an optocoupler. Their signals are sampled, processed and send to the control unit of the robot where are used in order to adjust the voltage supplied to the windings of the motor to regulate torque and rotational speed, via as example an embedded processor and a closed-loop control routine. A linear relation is expected between the applied voltage and the achieved rotational speed and delivered torque for a particular range of voltage values. The unit may further incorporate calibration routines that run the motors at the set location of the robot in order to calibrate its operation for the particular MR scanner and set-up and/or to diagnose the performance of the robot. The calibration may include but not limited to, changing stepwise the voltage and measuring the delivered torque and rotational speed, generating a response curve and automatically or with input by the operator setting the appropriate voltage to the motor. Furthermore the motors may incorporate appropriate gears to delivered the appropriate reduction ratio of its rotational speed for powering the transmission lines.

Figure 22A:
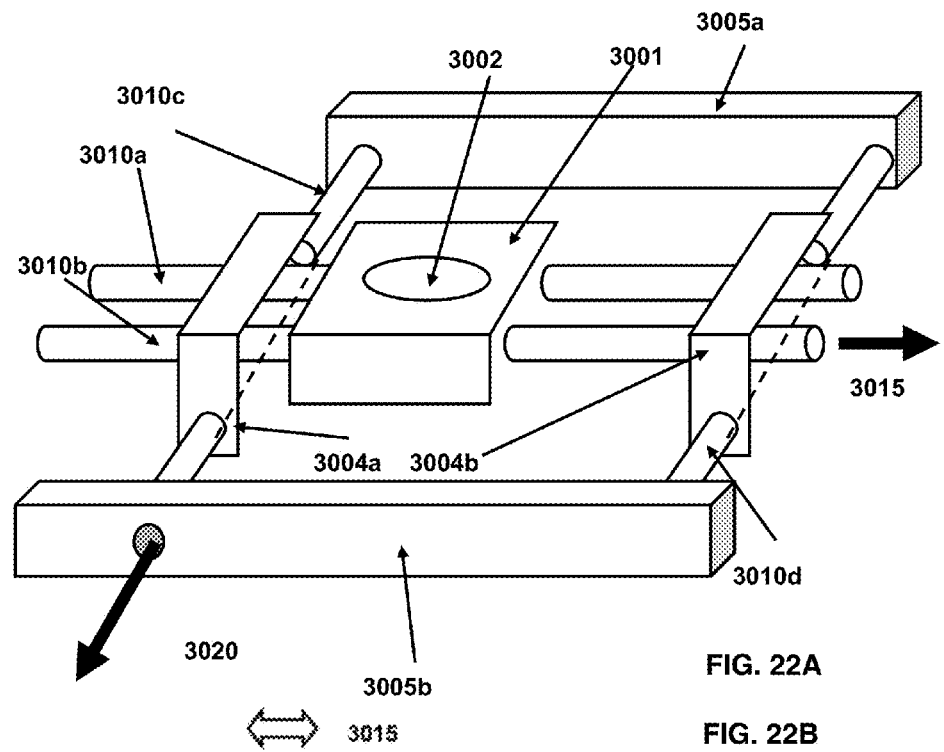
FIGS. 22A-22B: Schematic for the staging of the robotic device and rigid liquid actuation assembly for motion along X- and Z-axes.
Figure 22B:
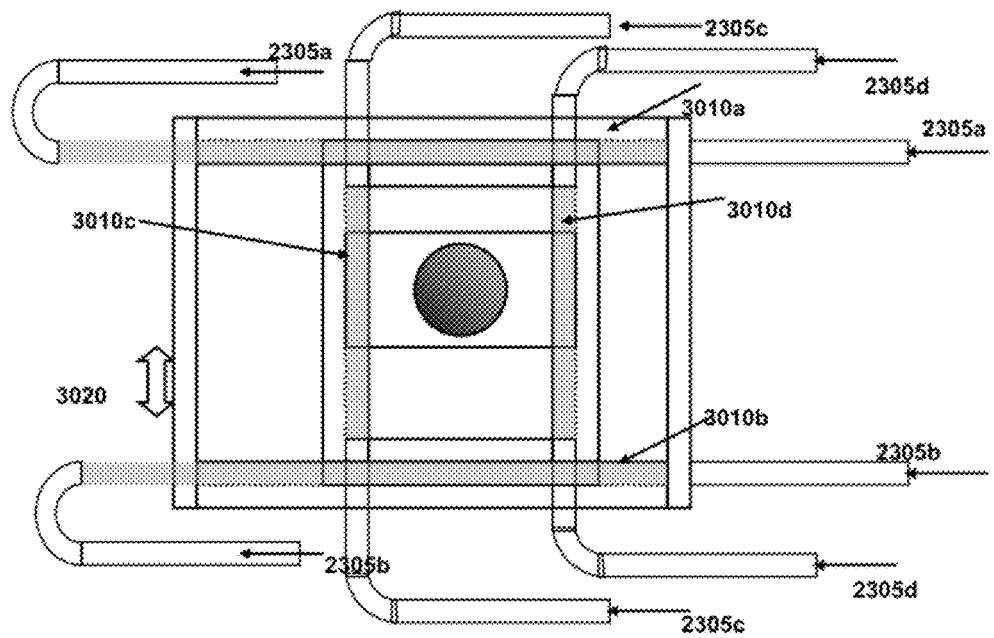

In yet another preferred embodiments there are provided examples of staging the robotic device for rigid liquid actuation. In this preferred embodiment, the rigid-liquid actuation assembly actuates the robotic manipulator for motion along the X- and Z-axes, as shown in FIG. 22A. The stage 3001 comprises an opening 3002 for the robotic manipulator. The stage moves between stage blocks 3004a,b on rails 3010a,b along the MRI z-axis 3015. The rails 3010c,d enable actuation along the MRI x-axis 3020 between end blocks 3005a,b. The rails comprise the container tubes for the rigid liquid actuation assembly. Also, in this embodiment, as shown in FIG. 22B, a top assembled view of the stage illustrates that the container tubes 2305a,b,c,d comprising the rails 3010a,b,c,d are depicted as comprising rigid and flexible, bendable components within the same tube.

Figure 23A:
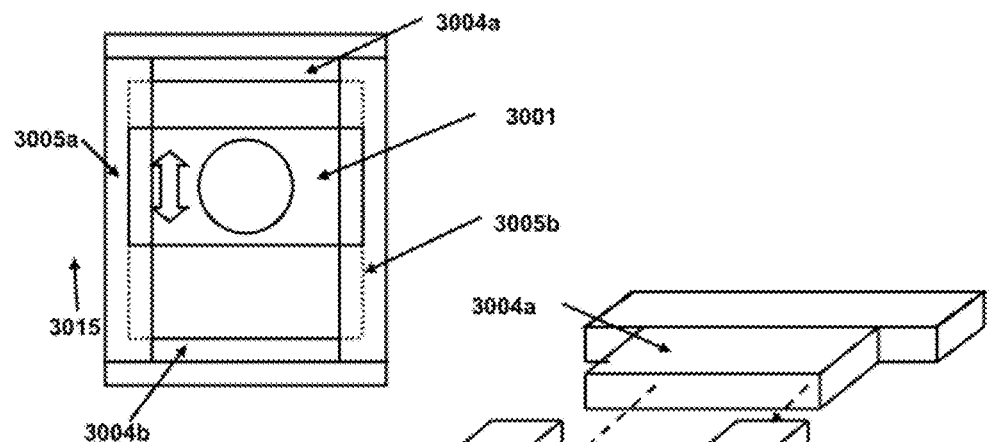
Figure 23B:
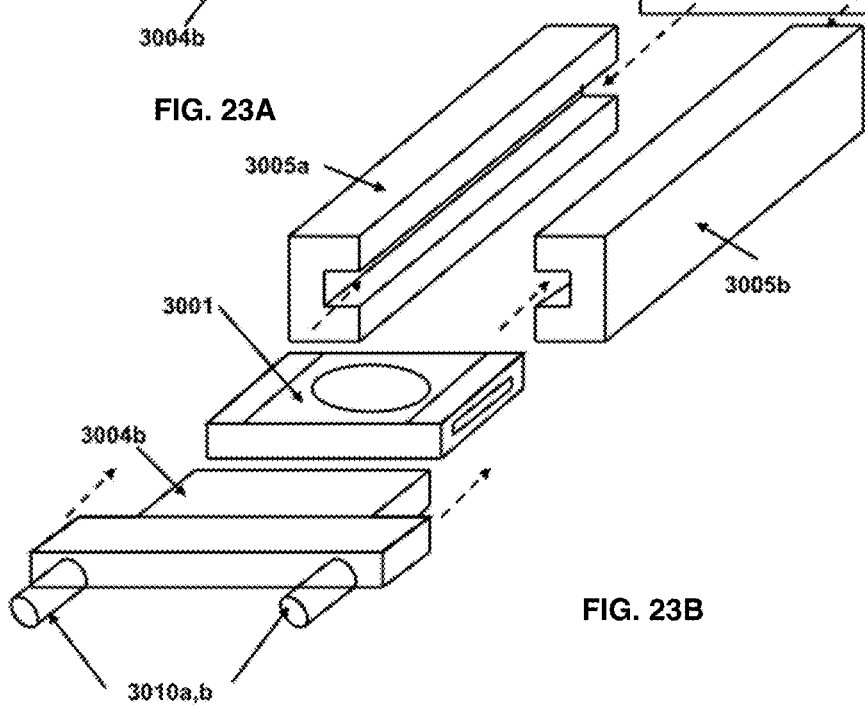
Figure 23C:
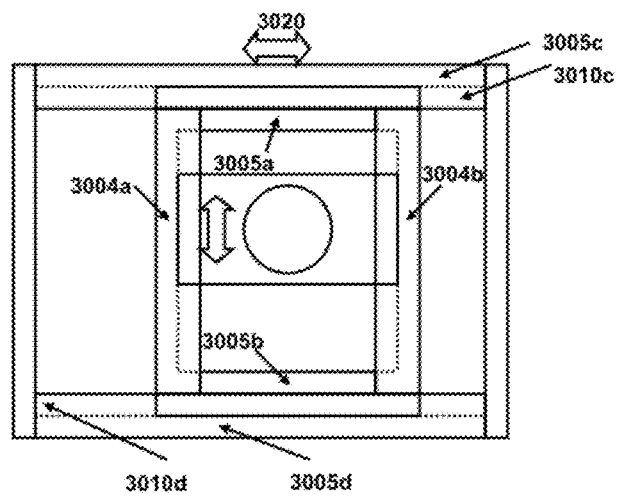
Figure 23D:
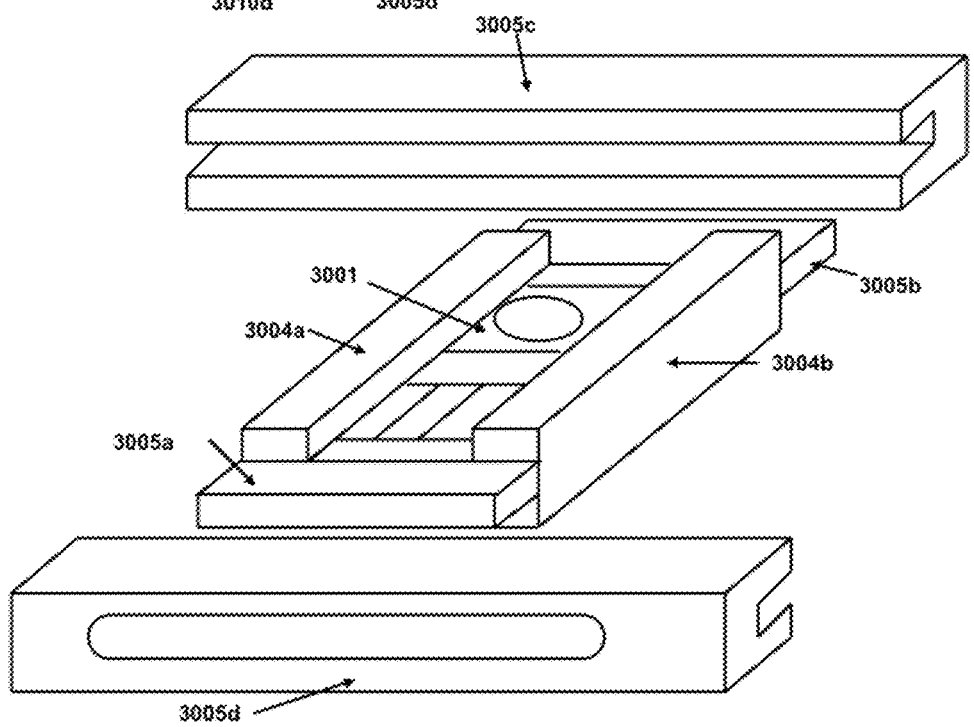

Also, in a related embodiment, as shown in FIGS. 23A-23B, are assembled and exploded views of a stage for motion along the MRI z-axis 3015. The stage 3001 moves within stage blocks 3004a,b along rails 3010a,b in the designated direction 3015 along the z-axis. The stage blocks are held in place with end blocks 3005a,b. Still in this related embodiment FIGS. 23C-23D further depict the end blocks 3005c,d with rails 3010c,d along which the end blocks 3005a,b move along the MRI x-axis 3020. The stage and the end blocks comprise a stage block. The stage and the end blocks comprise a stage block 3030 (see FIG. 24A). The components can be fastened together with, for example, screws and nuts. The shaded areas indicate those portions of the stage that are contained within the rails.

Figure 23E:
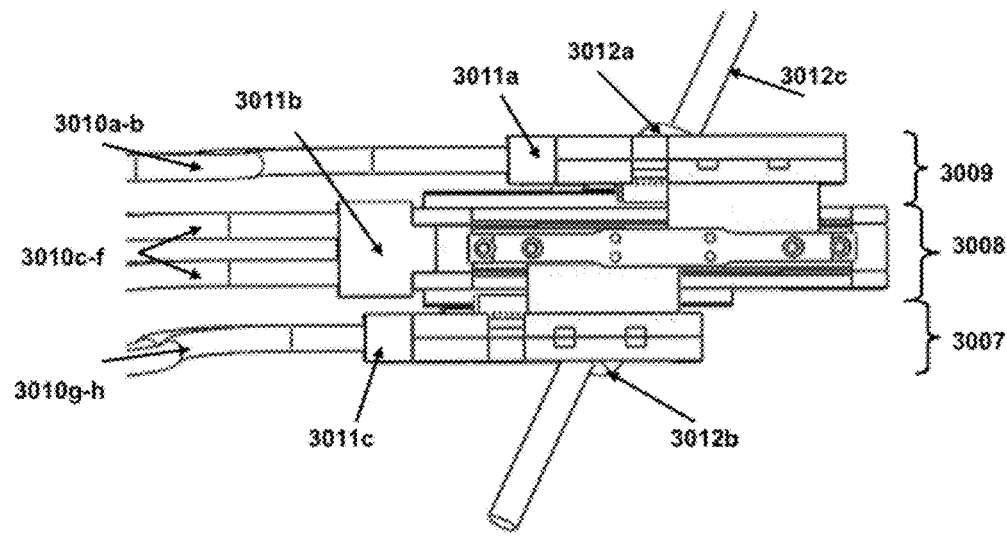

According to this embodiment, FIGS. 23E-23L show designs of a 4 DOF prototype robot that uses the rigid liquid transmission to actuate its 4 DOF. This is one representative way that such a robot can be implemented and constructed, based on the above described embodiments. FIG. 23E is a side view of the robot that comprises 1) three stages: 3007 that carries one DOF orthogonal to the axis of the DOF's of stage 3008 and parallel to the axis of 3009, 3008 that carries two DOF parallel to each and 3009 that carries one DOF orthogonal to the axis of the DOF's of stage 3008, 2) two universal passive joints 3012a and 3012b that carry the device 3012c, 3) a plurality of solid liquid transmission lines, in this case eight of them 3010a-h that are paired to provide bidirectional actuation of the DOF with the particular implementation of the embodiment in reference to FIG. 20G, 4) connections 3011a,b,c, for physically linking the transmission lines 3010a-h to the channels onto the stages 3007 to 3009. The DOF of this device are in appropriate orientations to provide the equivalent maneuverability with of two parallel 2D stages as discussed herein for setting the position and orientation in the 3D space of the interventional device 3012c relative to the axes defined by the plane of the device and an axis orthogonal to it.

Figure 23F:
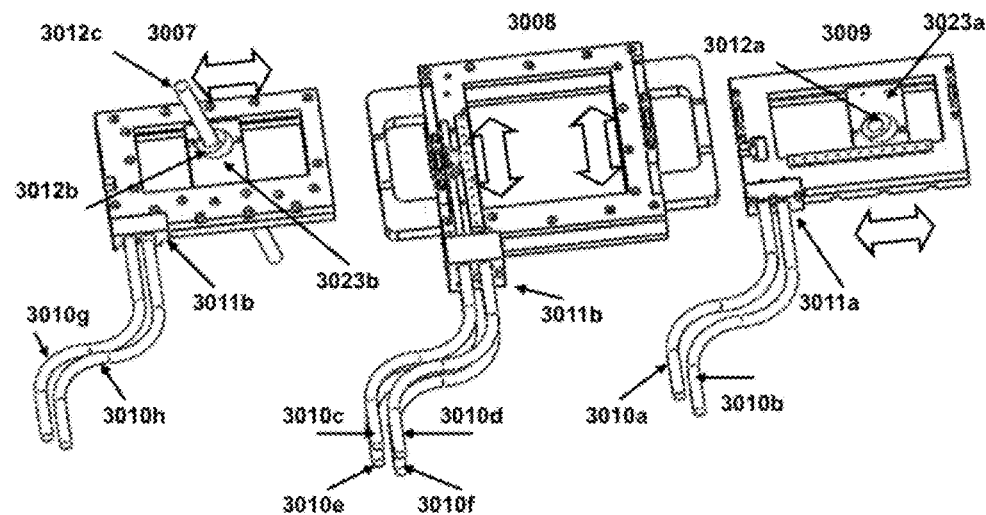

In this embodiment FIG. 23F illustrates the three stages 3007, 3008 and 3009 further depicting the four DOF of the device indicated with the block arrows and the two carriages 3023a,b that carry the two universal joints 3012a,b. FIG. 23G shows the middle stage 3008 further depicting the mechanical links 3016a and 3016b between the solid liquid transmission and the actuated parts that at this case are the two stages 3007 and 3008. The stage is manufactured in three layers 3013a,b and 3014. This sandwich-like method was used for low-cost and easier CNC creation of channels and other parts. Layers 2013a and 2013b are mirror images to each other relative to a plane that is parallel to and passes in the center of layer 3014. Similarly, the two surfaces of layer 3014 are mirror images to each other relative to a plane that is parallel to and passes in the center of layer 3014. This symmetry is implemented since each DOF of stage 3008 actuates one for the stages 3007 and 3009 that are interfaced to stage 3008 on each one of its sides (see FIG. 20E). Moreover in one aspects of this embodiment two DOF on stage 3008 independently and linearly move the other two stages. In another aspect stages 3007 and 3009 that have one DOF independently move the carriages 3023a,b along directions orthogonal to the axes of the two DOF on stage 3008.

Also, FIG. 23H and inset FIG. 23I show the details of stage 3008 by removing layer 3013a. Actuation lines 3010c and 3010d actuate the motion of the entire stage 3009 and lines 3010e and 3010f actuate the motion of the entire stage 3007. Particularly, in one aspect and in reference to the bi-directional transmission in FIG. 20G, the solid fluid (spheres) enters into the body of the robot supplied by tube 3010c and moves in the channel 3017 cutout into the body of the robot. The channel further directs the solid fluid via a 180 degrees turn returning it back to the other tube 3010d. In another aspect and in reference to FIG. 20h, the spheres of the solid liquid transmission directly engage the mechanical link 3016a that has a tooth-like interface. One major benefit of the leak-less solid-liquid transmission actuation versus pneumatic or pneumatic ones, openings are freely cutout to link the transmission with the actuated parts, sandwich-like structures are implemented and there is not need to provision piston travel. This enables a simpler manufacturing and maintenance at a lower cost. FIG. 23J shows the middle stage 3008 further depicting the two tubes 3010a and 3010b for bi-directional motion of the actuated part that is the carriage 3023a. The stage is manufactured with two layers 3021 and 3022.

FIG. 23K and inset FIG. 23L show the details of stage 2009, which is a mirror to stage 2007, by removing layer 3021, depicting similar aspects pertinent to the embodiments of this invention also described in reference to FIG. 23H. A channel 3024 has been cut into the body of the two layers 3021 and 3022 of stage 3009 to generate a path for the spheres of the solid liquid transmission. The actuated part carriage 3023a has a tooth-like interface so the spheres of the transmission engage directly to it.

An example of this implementation a working configuration was achieved using a 0.65±0.5 mm clearance with off-the-shelf nylon tubing (7 mm ID) and glass or HDPE 6.35 mm spheres. Bushings (6 mm OD, 4.5 mm ID, 3 mm length) were interleaved with the spheres to maintain alignment. Inside the frame-embedded channels (see FIG. 20H) successful actuation without bushings was achieved with a clearance of ~0.3 mm and a curved path bend with a radius of 12 mm. With standard NEMA 23 stepper motors and 7 m long, straight or spooled transmission lines with a bend diameter of ~33 cm, achieved accuracy of 1.3±0.6 mm, an almost undetectable backlash, and a bandwidth of 14 Hz for ±32 mm. Motors outside the MR scanner room resulted to no SNR degradation. The prototype was made with computer numerical control (CNC) machining out of the resin Ultem® and polyether ether ketone PEEK®, which have superior strength and lower friction coefficients.

Figure 24A:
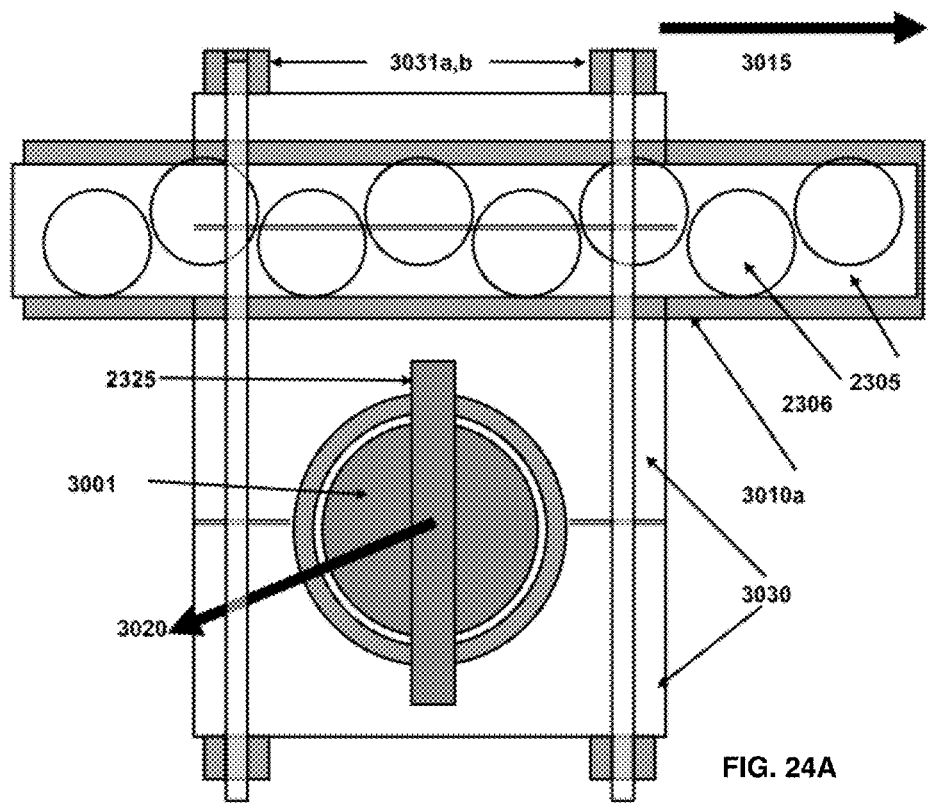
FIGS. 24A-24B: Depict the disposition of the actuators to actuate the robotic manipulator.
Figure 24B:
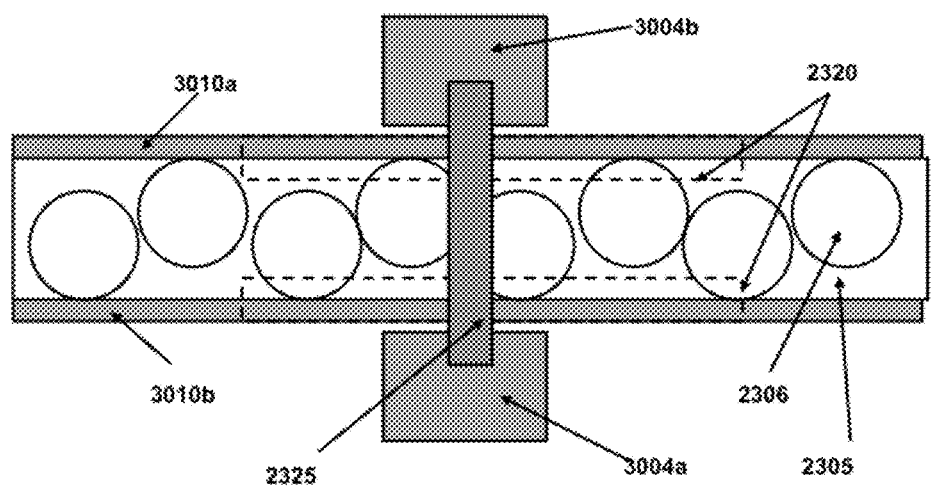

In addition in this embodiment, FIGS. 24A-24B depict the disposition of the actuators in relationship to the stage block of the robotic manipulator for actuation along the z-axis and x-axis. A top cross-sectional view, as shown in FIG. 24A, depicts the stage block 3030 and the screws/nuts 3031a,b holding the components of the stage block together. The direction of movement along the z-axis 3015 and x-axis 3020 is depicted. The rail 3010a, which contains the actuation spheres 2306 and comprises a container tube 2305 containing the spheres, enables the stage 3001 or stage block 3030 to move along its length. The container tube has 2 slits or openings 2320 (see FIG. 24B) through which the key link 2325, connected to the stage 3001, passes. In FIG. 24B, the key link 2325 is shown linking the actuation spheres 2306 to the stage block 3030 through the openings 2320.

Figure 25A:
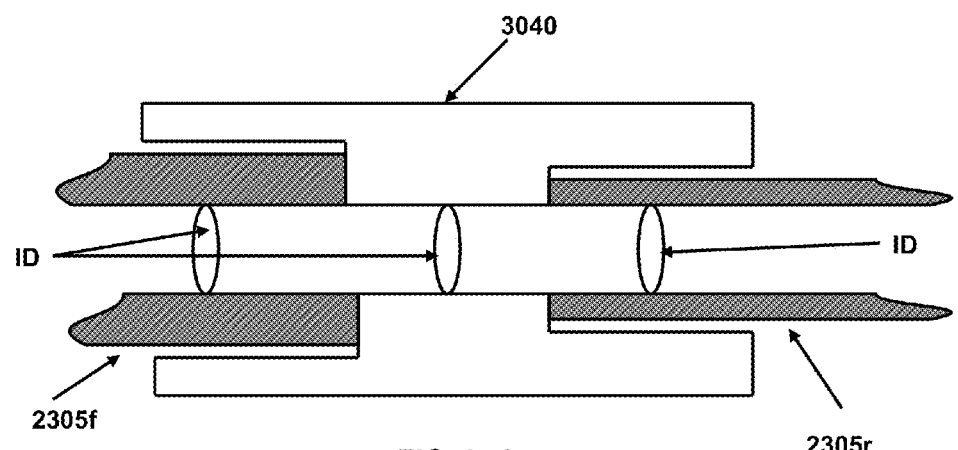
FIGS. 25A-25B: Depicts coupling flexible to rigid tubing.
Figure 25B:
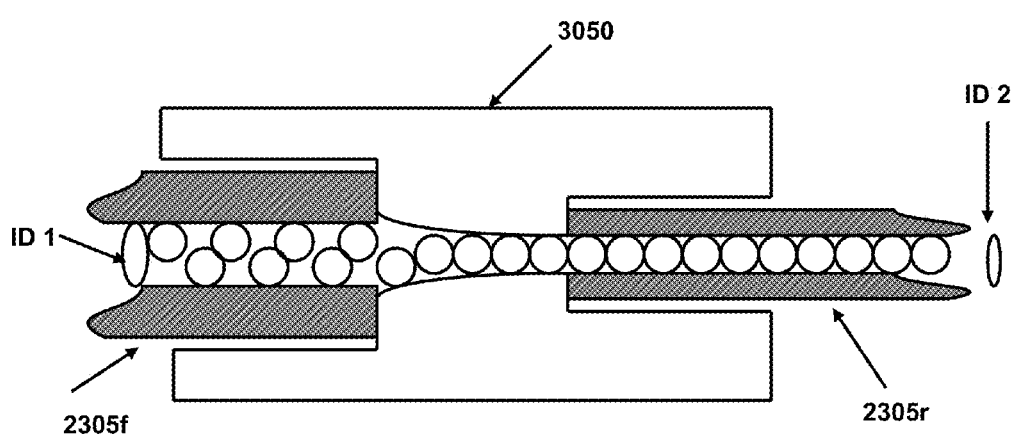

Furthermore, as shown in FIGS. 25A-25B, the sizes of flexible and rigid tubing need not be identical for them to be coupled. A standard coupler 3040 is well-suited to join a segment of flexible container tubing 2305f to a segment of rigid container tubing 2305r which have the same inner diameter ID, as shown in FIG. 25A. When the flexible tubing 2305f has an inner diameter ID1 that is greater than the inner diameter ID2 of the rigid tubing of the rigid flexible tubing 2305r, then a funnel-like coupler 3050 is utilized to gradually reduce the ID1 until it is equal to the ID2 of the rigid segment at the point where they are coupled.

In these preferred embodiments, the robotic manipulator is actuated manually by the operator, i.e. using man-power to actuate the different degrees of freedom (DoF) of the robotic device. With manual actuation, no power-assisting means are used for the actuation of the DoF of the slave manipulator, such as but not limited to, electromagnetic, DC or stepper or other type of motors. For the purpose of this invention, those manual actuation means will be herein referred as the manual actuation unit or MAU. Particularly, manual actuation preferred for the implementation of low cost systems and for having the operator residing by the scanner couch, and in particular an MRI scanner. Manual activation can comprise manual actuation with no electronics and software, manual actuation with electronics and software for the control of the imaging scanner, manual actuation with electronics and software for interfacing to the operator imaging information by means of i) an add-on to the imaging scanner or ii) using the hardware/software of the imaging scanner, manual actuation as bypass to a power-assisting one, and passive, assisted manual actuation by means of a hydraulic assembly for amplifying the power supplied by the operator.

Also, the manual actuation assembly can be connected to the rigid-fluid actuation lines in parallel to a power-assisted setup, e.g. with electromagnetic motors) with means of mechanical by-pass so that the operator can bypass the power-assisted setup as to provide means for direct human interventions and resuming total manual actuation and control as needed per the procedure or as a mechanism of addressing malfunctions or loss of power or other detrimental occupancies related, but not limited, to the power-assisted setup. In addition, the MAU may further be linearly connected to a hydraulic power amplifier to amplify the force applied by the operator. Furthermore, a weight or other type of assisting method can be used to make the actuation line with less resistance as felt to the operator, by setting the assisting force exactly between the maximum static frictions.

Figure 26A:
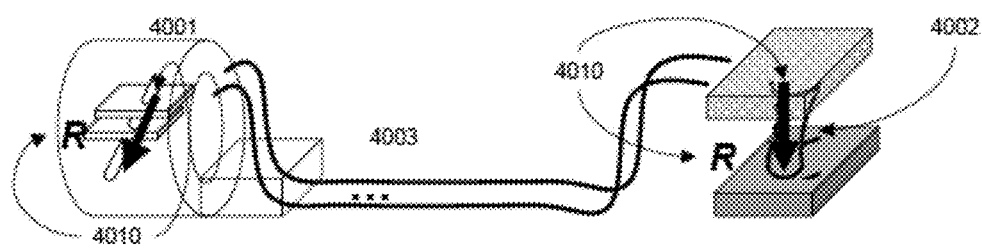
FIGS. 26A-26B: Schematics depicting actuation of the robot manipulator via manual power provided by the operator.
Figure 26B:
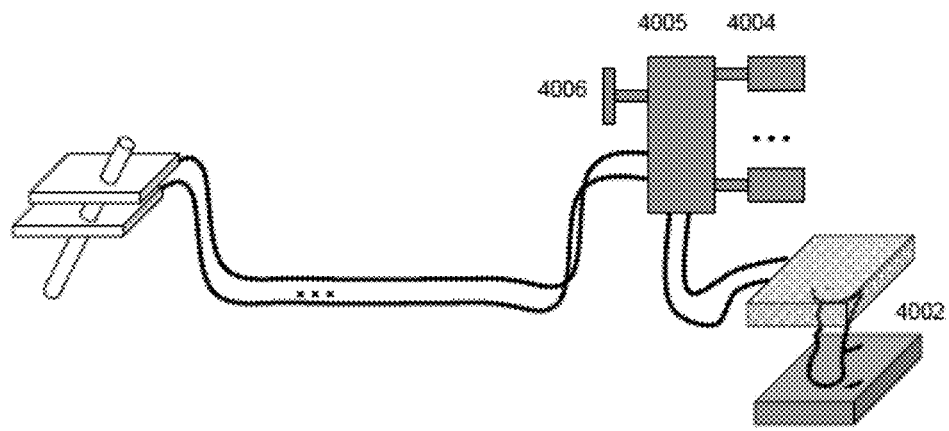

In yet another preferred embodiment of this invention and in reference to FIGS. 26A-26B, the actuation of the manipulator 4001 is manual, i.e. with power provided by the operator by means of a MAU, for example, but not limited to, the movement of one or more hand-actuated handles 4002 or one or one or more foot-activated pedals, i.e., the manual actuation assembly (MAA), or any combination of those two above or any other mean of manual actuation. In one aspect of this preferred embodiment, as shown in FIG. 26A, the manual actuation from the MAU is transmitted to the robot 4001 via a plurality of actuation lines 4003, their number determined by the exact kinematics of the actuated robotic manipulator. Also, the actuation lines 4003 are entirely or partially based on the rigid-fluid method and are of any combination of rigid or flexible container lines. Also, the MAU may resemble, but is not limited to, the kinematic structure of the robotic manipulator; this choice is in particularly desirable for providing intuitiveness and easiness/straightforwardness in construction, operator learning curve and operation.

In a preferred aspect of this embodiment, as shown in FIG. 26B, the manual actuation assembly father connects to the appropriate assembly of rigid fluid actuation lines that are used for the remote actuation of the DoF of the slave manipulator 4001. The slave manipulator 4001 is actuated manually with the manual power provided by the operator who manipulates the MAA 4002. The motion of the MAA causes the actuation of, for example, the rigid-liquid lines 4003 which subsequently transmit this actuation to the slave manipulator. In another aspect the manual actuation assembly is at a distance from the master manipulator, for example, but not limited to, outside the scanner room or behind a protective wall or obstacle as needed by the particular imaging modality, as example when sued with CT or fluoroscopic x-ray guidance, or by the procedure itself. In another aspect the manual actuation assembly is in close proximity to the patient table and its distance from the slave manipulator and the patient is optimized, preferentially minimized, to reduce friction and/or bring the operator at close proximity to the patient. This is particularly suitable for imaging modalities such as ultrasound and MRI.

Figure 27A:
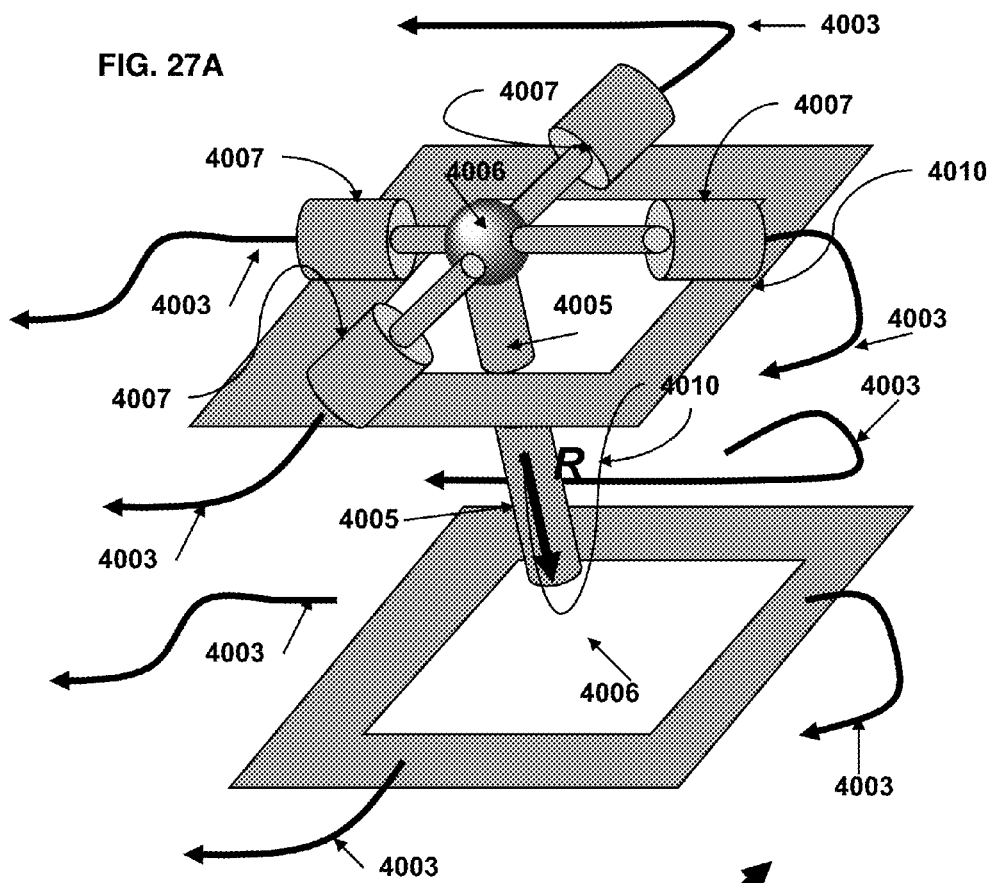
FIGS. 27A-27C: Various architectures of the manual-actuation unit (MAU).
Figure 27B:
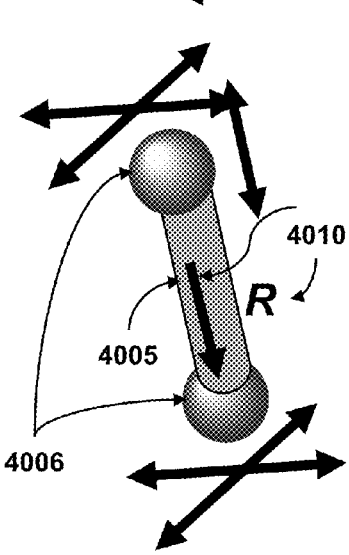
Figure 27C:
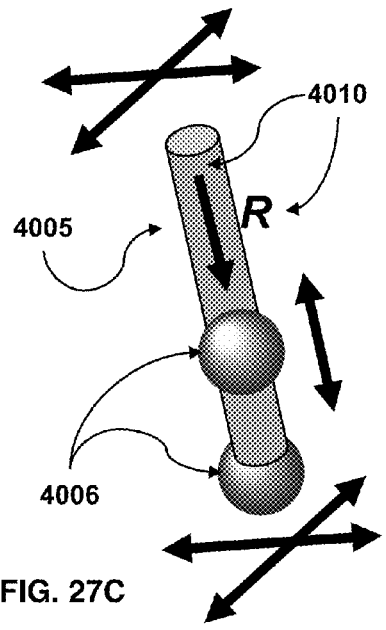

In yet another preferred embodiment of this invention and in reference to FIGS. 27A-27C, architectures of the MAU are depicted. In this preferred embodiment, as shown in FIG. 27A, the MAU is a handle 4005 with two points on its body appropriately connected by means of two mechanical links 4006 so that the handle can move in the 3d space to define the orientation of a vector R 4010 that is parallel to the path along which the robotic manipulator advances the say interventional tool that carries on its end-effector. The two mechanical links 4006 are further mechanically linked to a plurality of actuation lines 4003 via appropriate mechanical implements 4007, such as but not limited to piston-like entities, in order to transfer manual actuation from the moving hand of the operator to the remote robot 4001. The two mechanical links 4006 are universal joints or 3D joints allowing angulation of the handle and, via the actuation lines, the corresponding motion of the remote robot 4001.

In this embodiment at least one of the mechanical links 4006 allows or enables the free and passive sliding of the handle, as to adjust for accommodating the fact that the angulation of the handle requires a variable distance between the mechanical links 4006. Also, the MAU includes one or more foot-pedals to selectively brake one or more DoF. In addition the operator grip 4005 can be in-between the two mechanical links 4006, as shown in FIG. 27B, or outside the space in-between the mechanical links 4006, as shown in FIG. 27C.

In yet another preferred embodiment of this invention and in reference to FIGS. 28A-28D, a preferred arrangement or architecture of the manually-actuated robot is shown. In this arrangement the operator is standing or sitting on a heightadjustable chair by the side of the couch of the scanner on which the patient is located. The MAU is preferentially anchored, for example, but not limited to, on a mobile, but with caster and brakes, podium and/or onto the patient couch with lateral and vertical adjustments so the MAU is adjusted for better fitting the needs of the operator.

Also, the MAU, in addition to remotely actuating the robot, also controls the specific acquisition parameters of the imaging modality. The MAU controls the acquisition parameters of, for example, MRI scanner that include, but are not limited to, the number and orientation of the imaging planes, relative to the coordinate system of the MR scanner, and in order to better capture the area of the procedure, for example, planes that preferentially adjust on-the-fly their orientation to match and capture the motion of the end-effector of the robot, the targeted anatomy, and the anatomical structures along the path of maneuvering of the say interventional tool that is attached onto the end-effector.

In this embodiment, the MAU controls the acquisition parameters of, for example, an ultrasound scanner with mechanized ultrasound probe that include but are not limited to, the orientation of the imaging plane or planes relative to the patient body better capture the area of the procedure as example, but not limited to, planes that preferentially adjust on-the-fly their orientation to match and capture the motion of the end-effector of the robot, the targeted anatomy and the anatomical structures along the path of maneuvering of the say interventional tool that is attached onto the end-effector. Also, the MAU controls the acquisition parameters of, for example, an optical scanner with mechanized optical probe that include but are not limited to, the orientation of the imaging plane or planes relative to the patient body better capture the area of the procedure as example, but not limited to, planes that preferentially adjust on-the-fly their orientation to match and capture the motion of the end-effector of the robot, the targeted anatomy and the anatomical structures along the path of maneuvering of the say interventional tool that is attached onto the end-effector.

In this embodiment, as shown in FIG. 28A, the manual-actuation unit 4002 is further equipped with a plurality of position encoders 4021 on its DoF for measuring the exact movements that the operator enters by moving the handle. Also, the position encoders are placed onto each one of the actuation lines of the rigid-fluid lines at their distal end, or at any other position, to measure the translation of a point of the rigid-fluid or the particular DoF on the slave manipulator. The signals from the position encoders 4021 are transferred via wiring 4022 that interfaces by means of an appropriate type of interfaces 4023 to an electronic unit 4020. A physical connection by means of say, but not limited to, a dedicated Ethernet TCP/IP connection 4025 to the appropriate control unit 4024 of the imaging scanner say, but not limited to, an MR scanner 4027.

Also in this embodiment, as shown in FIG. 28B, the unit 4020 at least comprises, but is not limited to, interconnecting electronic components. The unit 4020 may comprise a central processing unit 4030, or a microprocessor with associated type of memory 4031 and removable storage. Also, the unit may comprise one or more electronic components 4032, with a plurality of input, for sampling the signals from the plurality of the position encoders and digitizing them in a form appropriate for use by the software of the electronic unit. These components can be counters or otherwise appropriate converters to quantify the motions ordered by the operator with the MAU. Optionally, but preferably, the unit may also comprise a plurality of additional input/output channels 4033, for example but not limited to, digital I/O, analog-to-digital converts. In addition, the unit may comprise one or more interfaces, such as, but not limited to, a plurality of Universal Serious Bus—USB 4034 and at least one, but in generally a plurality of, Ethernet interfaces 4035. Optionally, but preferably, the unit may also comprise appropriate bus 4036 for expansion with additional cards for additional tasks. Furthermore, the unit may comprise means for the operator to enter parameters or select choices, such as, but not limited to, a LCD display connected by an appropriate interface 4037, keyboard, mouse, touch-sensitive screen, or via an external PC connected by but not limited to a USB port or Ethernet. Further still, the unit may comprise a power inlet 4038 for direct input from the power supply of the facility 4039 and, optionally, but preferably, via a back-up battery unit 4040.

In addition in this embodiment, as shown in FIG. 28C, the MAU electronic unit also includes a video card 4062 which can be part of a single board implementation of the MAU electronic unit. Alternatively, as shown in FIG. 28D, the video card 4062 can comprise an add-on to the MAU electronic unit, using a suitable bus 4036 on the board.

In these preferred embodiments, the central processing unit or microprocessor and the associated electronic components can be part of the same board (see FIG. 29B) or multiple boards with connectivity and expandability such as boards as example but not limited to of the PC104 standard. Also, the software can be implemented on a single unit based on a field-programmable gate array (FPGA) as an integrated circuit. In addition the operation of the electronic unit 4020 is based on reconfigurable and expandable software 4041 that resides in part or in its entirety, in the RAM of the CPU or an external removable memory unit, such as but not limited to an SD card or an external hard drive, or in the memory of the FPGA, if this is used.

Figure 29A:
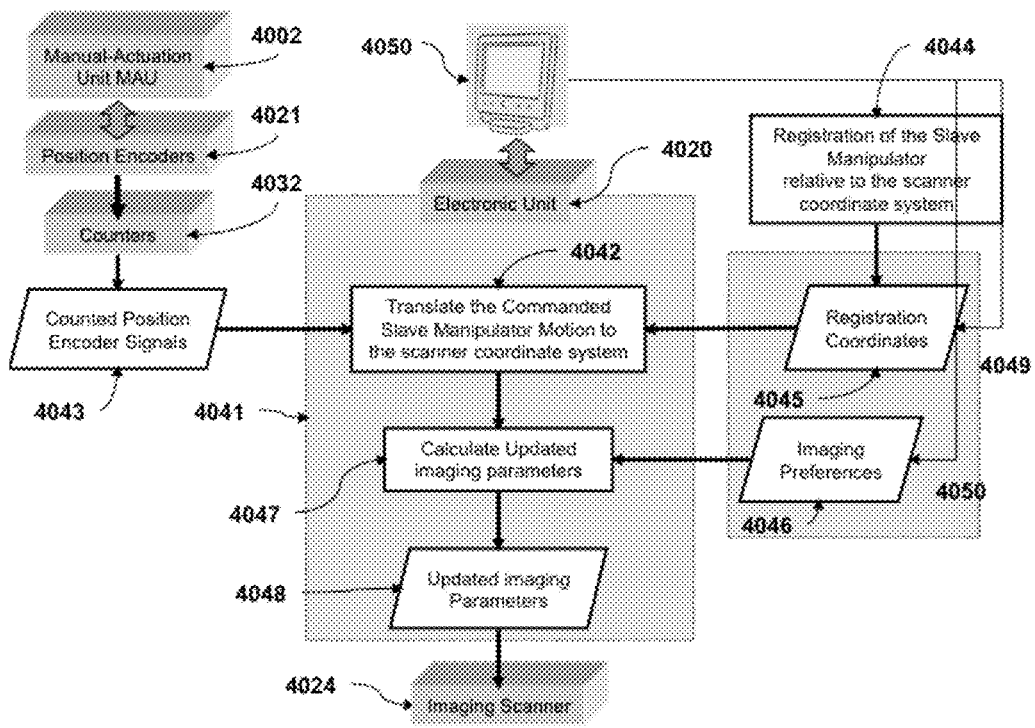
FIGS. 29A-29B: Details of the hardware and software of the MAU electronic unit.
Figure 29B:
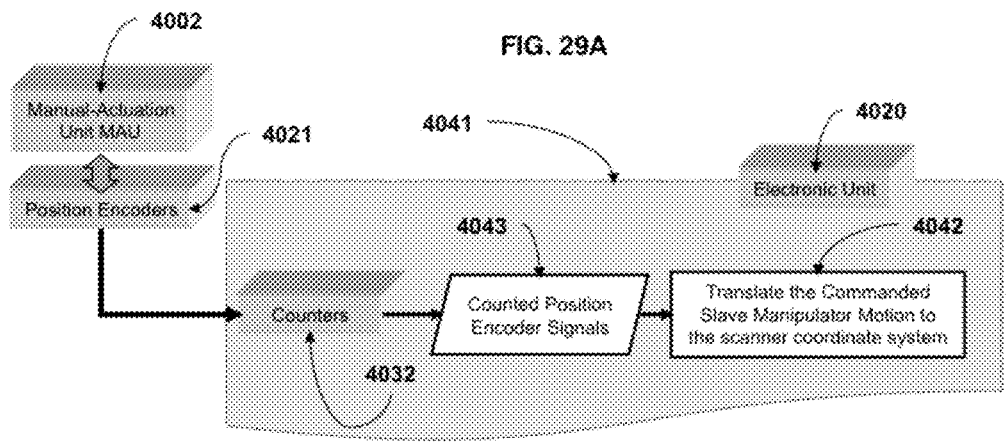

In yet another preferred embodiment and in reference to FIGS. 29A-29B, the software 4041 that runs in the electronic unit 4020 includes software modules, that are interconnected via pipelines, for exchanging raw and/or processed data, performing processes, and tasks is illustrated. In this preferred embodiment, as shown in FIG. 29A, the software may comprise a module for entering the selections of the operator, and this module receives this data via a type of human-machine-interface such as but not limited to a touch-screen 4050. These data can be, but are not limited to, the coordinates of the initial registration of the robot 4049 and the preferred way the imaging parameters will be changed 4050. This module may have appropriate graphical objects to direct the operator for electing options.

Also, the software may comprise a module 4032 for sampling the signals generated by the position encoders 4021 on the MAU 4002, converting them to the appropriate form and measuring the exact movement of the corresponding DoF made by the operator on the MAU. The output of this module are the digitized and counted signals of the position encoders 4043. In addition the software may comprise a module 4042 for translating the digitized signals 4043 from the encoders of the MA to spatial coordinates relative to the coordinate system of the imaging scanner. This module uses the coordinates 4045 of the initial registration of the robot relative to the coordinate system of the imaging scanner.

Furthermore, the software may comprise a module 4047 for calculating the updated imaging parameters 4048 in a form that is compatible for input to the imaging scanner, and according to the format that the OEM of the scanner specifies. This module uses the imaging preferences 4046 that the operator pre-selects or selects on-the-fly via, as example but limited to, via the touch screen interface 4050.

Further still the software may comprise a module for sending the updated parameters 4048 on-the-fly to the imaging scanner 4024.

Alternatively, to the separate implementation of the position encoder signal digitization 4043 and counting component 4032 and associated software, as shown in FIG. 29B, the module 4032 comprising counters and the output 4043 of the digitized and counted signals of the position encoders 4021 can comprise a single board implementation.

Figure 30:
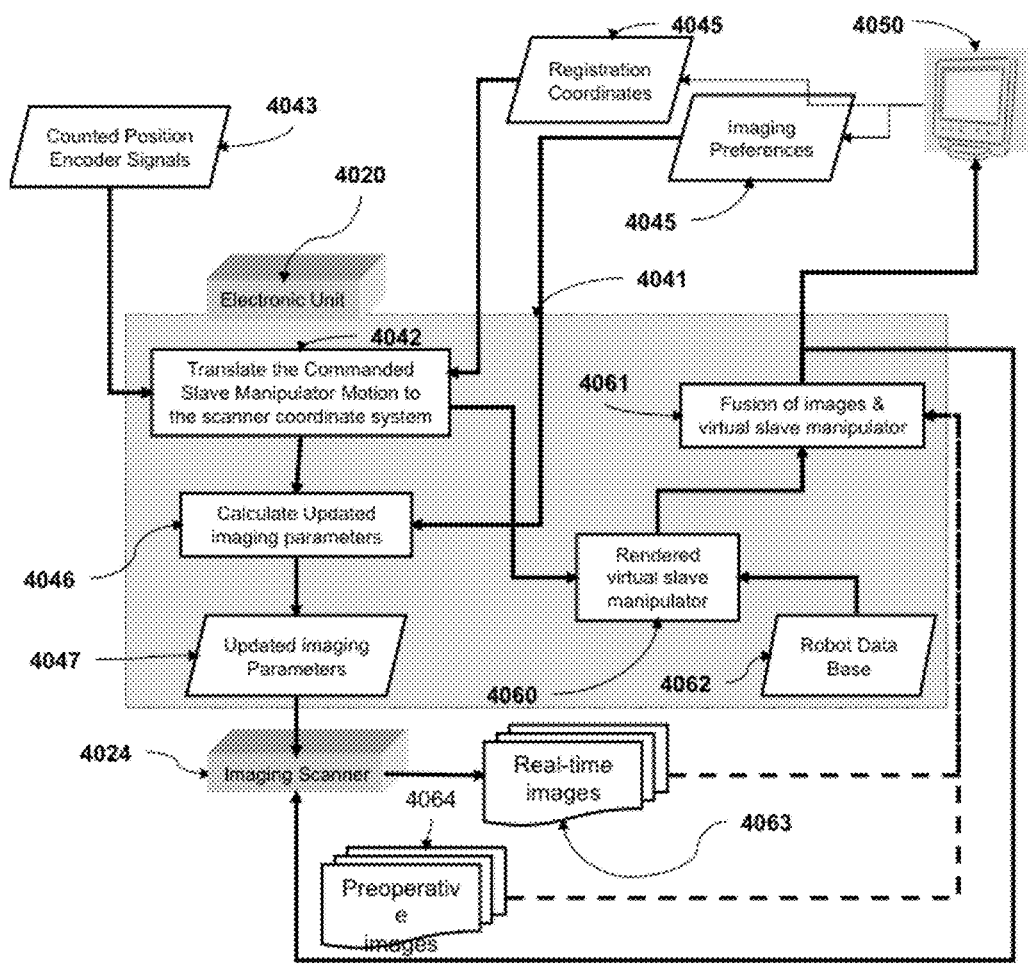
FIG. 30: The software modules of the MAU electronic unit, the flow of data and commands, and their interconnectivity and interfacing.

In yet another preferred embodiment and in reference to FIG. 30, the MAU electronic unit 4020 may further include additional hardware components and software modules to perform the generation, update and presentation to the operator of a visualization interface that fuses images and robot guidance information. In a non-limiting example, the software further may comprise a module 4060 that graphically renders a virtual representation of the robot, or the robot applicator, or the robot end-effector or parts of them in the coordinate system of the imaging scanner. This module receives all pertinent information about the position of the robot from the module that translates the MAU movements to the imaging scanner coordinate system. This module also receives information about the geometric features and dimensions of the robot from a date base 4062 stored on board the unit or from an external memory medium.

Figure 31A:
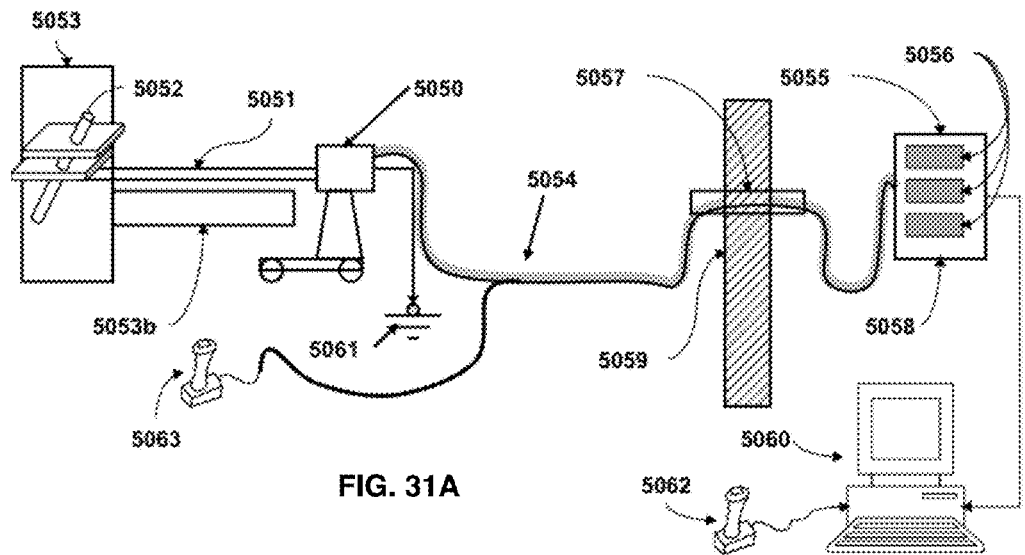
FIG. 31A-31E: Depict various site plans with the motors inside the MR scanner room

Also the software further may comprise a module 4061 that generates a visualization scene by fusing (1) the rendered robot what is generated by module 4060 with a feed of real-time intraoperative images 4063 that are received by the Unit directly from the imaging scanner 4024. In addition the software further may comprise a module 4061 may alternatively receive and use for the above stated purpose pre-operatively collected images. In this preferred embodiment the MAU electronic unit 4020 may be an add-on or a plug-in or plug-and-play type of unit for the imaging scanner. Also, the MAU can be utilized to remotely actuate the robot, to connect the MAU to the robotic manipulator, and to control, for example, a MR scanner shown In yet another preferred embodiment of this invention and in reference to FIGS. 31A-31E, the site setup is configured for when the robotic manipulator is actuated with power assistance using a power actuation unit PAU. The PAU 5050 is located inside the shielded MR scanner room 5059, as shown in FIG. 31A. In this embodiment, the PAU 5050 is located to a position appropriately close to the robotic device 5052 that resides inside the scanner 5053 and links to it with appropriate actuation lines 5051 or may be located to a position appropriately distant from the isocenter of the MR scanner to minimize effects of the constant or switching magnetic fields of the MR scanner. Also, the PAU 5050 can be anchored onto the patient couch of the MR scanner 5053b. Alternatively, the electronics and power supplies 5056 of the robot and PAU are located outside the shielded MR scanner room.

The wiring 5054 that connects the PAU 5050 to the plurality of electronics and power supplies 5056 is preferably shielded with appropriate conductive material as known to the specialists in the art. In addition the plurality of electronics 5056 are further connected to a computer for controlling the robot and planning and executing the procedure that may include interfacing to a plurality of human-computer interfacing, such as but not limited to a joystick or other force-feedback device 5062,5063, that can reside outside the MR scanner room 5062 and be accessible by the operator or inside the MR room. Furthermore, the shielded wiring 5054 passes through the shielded wall 5059 of the MR scanner room via an appropriate conduit, for example, but not limited to, a waveguide 5057 or filtered sockets or other means as known in the of MR installation.

Figure 31B:
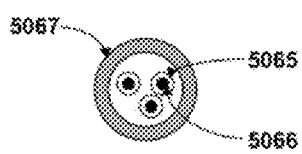
Figure 31C:
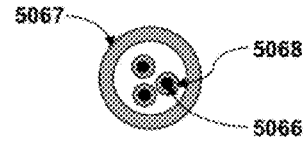

Also in this embodiment, as shown in FIG. 31B, the wiring 5054 may be composed of a plurality of wires that are each one individually shielded with an appropriate shield 5065 around its core conductor 5066, to eliminate interference and cross-talk among the individual wires and are encased into an external shield 5057 to reduce or eliminate interference to the MR signal. Alternatively, as shown in FIG. 31C, the wiring 5054 may comprise a plurality of wires that have a conventional sheath around them 5068 around its core conductor 5066, to eliminate interference and cross-talk among the individual wires and are encased into an external shield 5067 to reduce or eliminate interference to the MR signal.

Figure 31D:
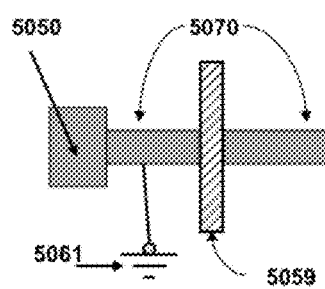
Figure 31E:
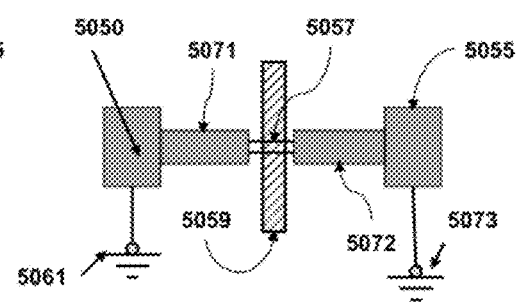

In addition in this embodiment, as shown in FIG. 31D, a continuous shield 5070 encloses the PAU 5050 and the electronics box 5055 passing through the shielded wall of the MR scanner and further may be or maybe not grounded to the ground 5061 of the MR scanner. Alternatively, as shown in FIG. 31E, two separate continuous shields 5071 and 5072 are employed. Shield 5071 encloses and shields the components inside the MR scanner room, including, but not limited to, the PAU 5050 and its wiring 5054. The second shield 5072 encloses and shields the components outside the MR scanner room and, preferably, where the operator is located, shields, for example, but not limited to, the electronics box 5055. The two shields terminate and interface to the waveguide 5057 and may have one or more grounds, such as one ground 5061 inside the MR scanner room and the other ground 5073 to the portion outside the M\R scanner room. Any combination of grounds can be used as known to the artisans.

Figure 32:
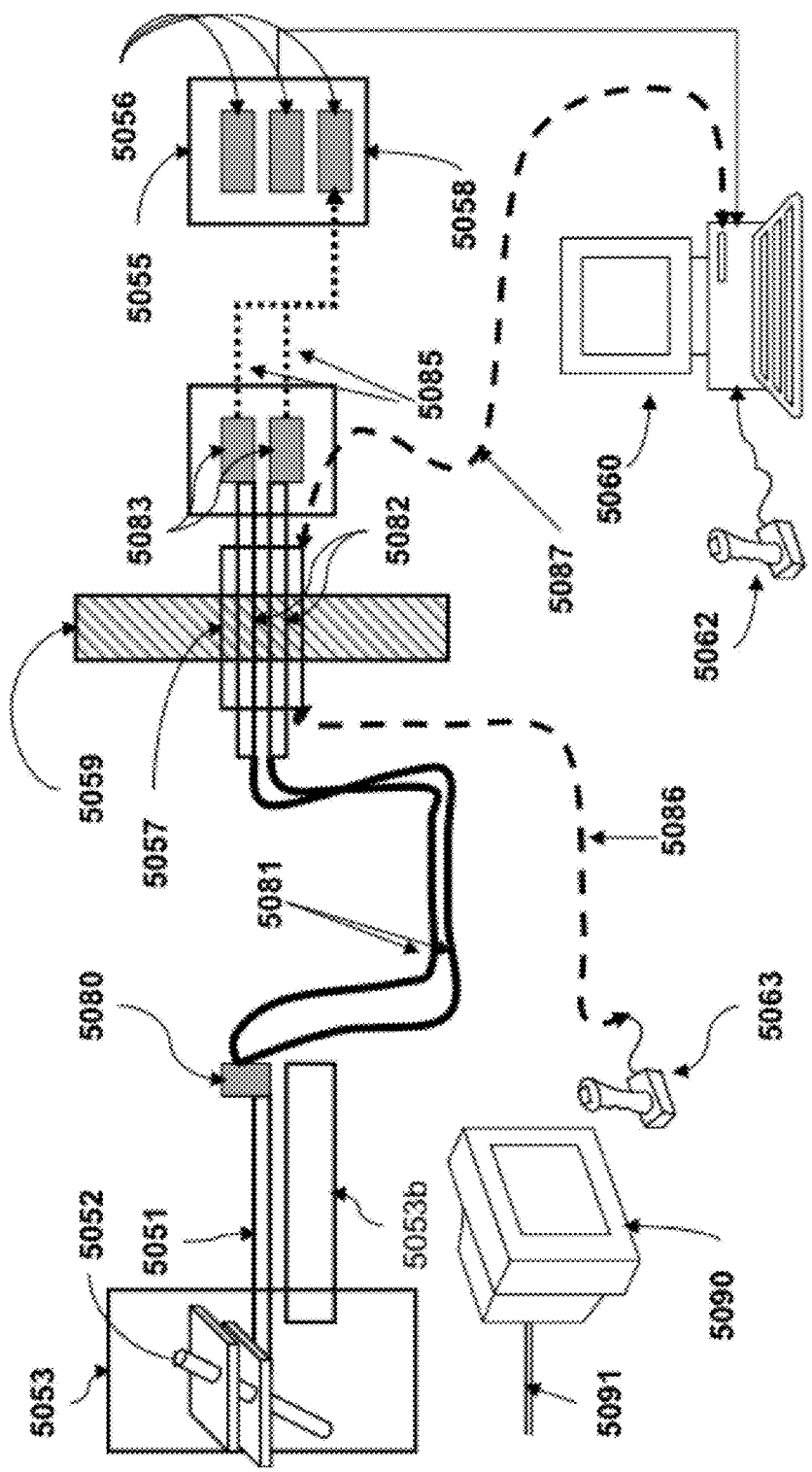
FIG. 32: Depicts a site plan with the motors outside the MR scanner room; the simplicity of this approach further exemplifies the commercial and practical value of the system.

In yet another preferred embodiment of this invention and in reference to FIG. 32, the site setup also is configured for when the robotic manipulator is actuated with power assistance using a power actuation unit PAU the PAU is located outside the shielded MRI scanner room. In this preferred embodiment the motors 5083 of the PAU are placed behind the shielded wall 5059 of the MR scanner room and preferentially at position close to or aligned to the waveguide 5057 of the shielded wall 5059. This arrangement may preferentially used to minimize noise form the PAU to the MR images and effects of the magnetic field of the MR scanner to the operation of PAU. It may further be preferred for a lower cost system.

Also, the actuation lines 5082 transverse the waveguide 5057 from the outside to the inside of the MR scanner room, and preferentially connected with extension actuation lines 5081 from the vicinity of the inside side of the waveguide to the area close to the patient couch 5053b, where it links via appropriate links 5051, such as, but not limited to, pistons and/or to the robotic manipulator 5052 that resides inside the MR scanner 5053. This is a preferred means for transmitting actuation from the PAU that resides outside the MR scanner room to the robot that resides inside the MR scanner. This transmission line may comprise any combination of rigid or flexible container tubing" with pistons or rigid-fluid transmission or any combination of the above.

In addition the plurality of electronics 5056 that may be inside an RF shielded enclosure 5055 are further connected to a computer 5060 for controlling the robot and planning and executing the procedure that may include interfacing to a plurality of human-computer interfaces that may include any combination of interfacing means, such as but not limited to visualization display 5060b, a joystick or other force-feedback device or combination of such 5062, that can reside outside the MR scanner room 5062 and be accessible by the operator or inside the MR room 5063 and be connected via appropriate shielded lines 5086 and 5087 via the waveguide 5057 or other means of filtered transversing of the shielded wall 5059. When the operator resides inside the MR scanner room, images and other information pertinent to the operation are displayed on a visualizations screen connected 5091 to the MR scanner or preferentially to the processing unit that resides inside the electronics box 5058 or the computer 5060.

Figure 33:
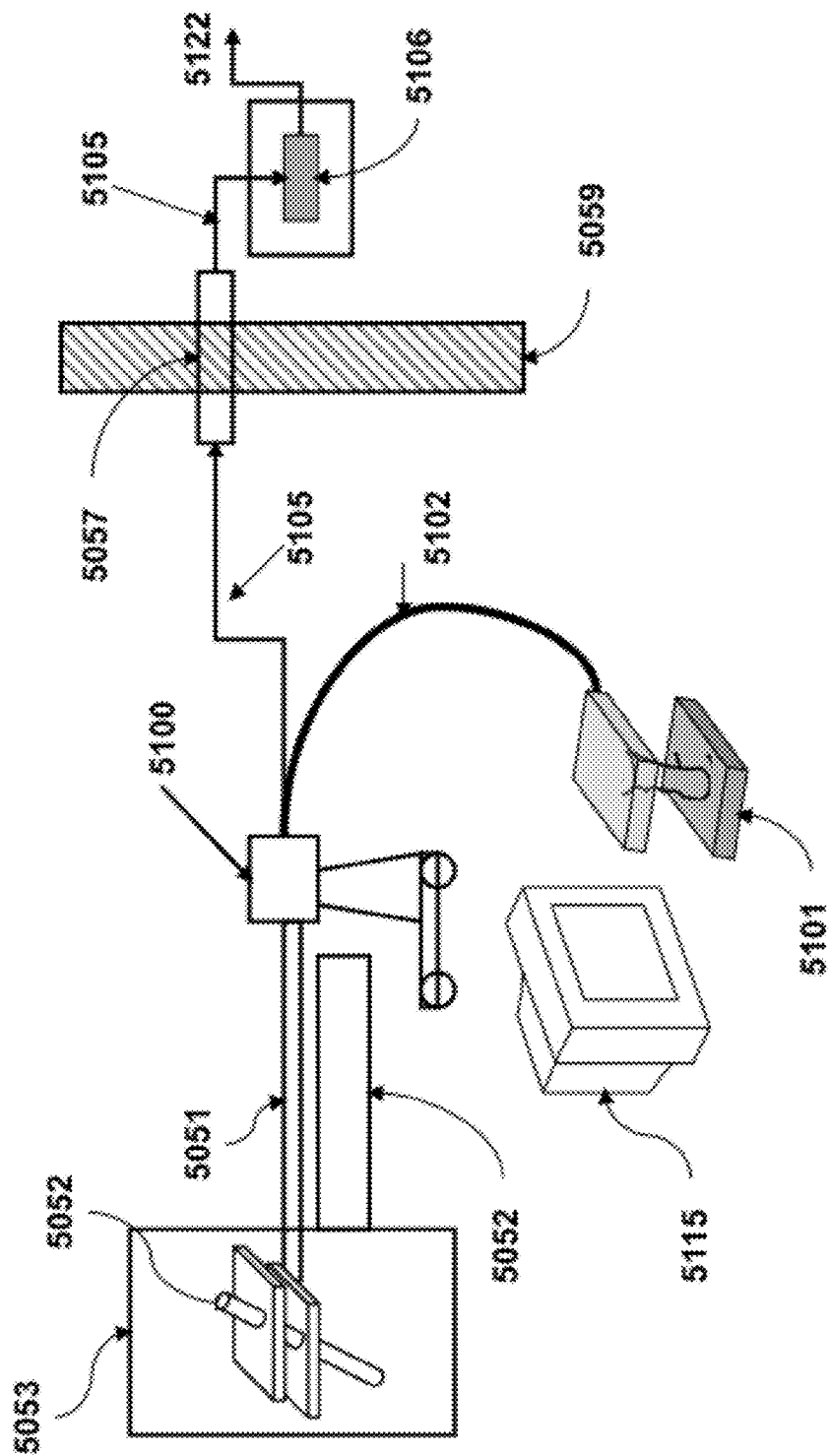
FIG. 33: Site planning with an MAU

In yet another preferred embodiment of this invention and in reference to FIG. 33, site set up Is configured for the manual actuation of the robot with a manual-actuation unit (MAU). In this preferred embodiment, the robot 5052 is actuated with a manual actuation unit (MAU) 5101 that resides inside the MR scanner room. This setup is particularly preferred for using manual-actuation and with the operator by the patient couch. In this embodiment the MAU 5101 is connected to the robot 5052 via an appropriate transmission set-up that entails any appropriate combination of rigid-fluid rigid 5051 and/or flexible actuation lines 5102. Also the position encoder signals are sent via a shielded or not shielded cable 5105, through the waveguide 5057 of the shielded wall 5059, to a processing unit 5106, that performs different tasks as described elsewhere in this invention, that include, but are not limited to, sending processed signals to the MR scanner 5122 and/or receiving MR images/data and sending renderings to a visualization display 5115 inside the MR scanner room by the operator.

In yet other preferred embodiments of this invention and in reference to FIGS. 34A-34I, the robot further incorporates sensors that are mounted onto the robotic manipulator and preferably onto the second 1051 and third 1052,1053 units. Types of such sensors are relevant to guidance of the robot and to performing the interventional or surgical procedure. There are two such categories of sensors.

The first level of sensors is at the macroscopic level and provide information about the local anatomy. Ultrasound (US) sensors are particularly pertinent to this category. A US probe may be mounted onto the distal end of the robot and it is used for two tasks. It is utilized as sonar, for 3D or planar mapping the tissue boundaries that surround the robot and preferentially forward of the robot. This takes advantage of the very high speed of collecting the ultrasound data, thus it is in particularly useful to the art of robot maneuvering and control and can be a supplement to the primary guiding modality. Of particular interest to this invention is, but not limited to, the combination of MRI or CT or fluoroscopy as the primary guidance modality supplemented with the robot-mounted US probe for ultrafast sensing the tissue boundaries forward to the probe. It is further disclosed that for the sonar application of the US, the space between the US probe and the surface of the surrounding tissue should be filled with appropriate medium, such as the natural blood of the cavity inside which the robot operates, such as but not limited to the ventricles or the atria of the heart. The ultrasound probe can be a linear array or a single crystal element.

The second level of sensors comprises a morphologic sensor to image inside the tissue in front of and around the distal tip of the robot. In this case the robot is substantially pressing or touching the active area of the probe onto the tissue of interest as to generate the appropriate contact for transmitting ultrasound waves into the tissue and receiving the echoes for generating the ultrasound images.

In this preferred embodiment, as shown in FIG. 34A, in MR scanning the primary guiding modality is combined with sensing with the robot mounted sensor along a line of site $A_1$ to $A_2$ and with a wide FOV-MRI of the area of the procedure (AoP). In one aspect, as shown in FIG. 34B, an optical sensor or probe that may comprise an extendable needle is utilized. In another aspect, as shown in FIG. 34C, the sensor is on the surface of the end-effector and operates with direct surface-to-surface contact with the tissue, for example, with optical methods or high-resolution ultrasound. In yet another aspect, as shown in FIG. 34D, the probe can be actuated to image a cone-like or funnel-like 3D area forward of the probe. This can be performed, for example, but not limited to, utilizing a cable that rotates sensor +/−90 degrees.

Also in this preferred embodiment, as shown in FIG. 34E, the distal end of the end-effector may further carry a mechanism for deploying a sensor or a tool 5200 where its length (L) is in generally longer than the diameter (D) of the third Unit 1052,1053 and its active side 5202 is along its long dimension (L). This mechanism that can be actuated by means of bicycle-cable arrangement or by a hydraulic or other means. In one aspect, as shown in FIG. 34F, carrying the sensor or the tool 5200 is carried alongside the third unit 1052/1053. In another aspect, as shown in FIGS. 34G-34I, the sensor or the tool 5200 is rotated orthogonal to the axis of the third unit 1052/1053 through a series of motions, e.g., as those depicted by the block arrows, such that its active side 5202 is facing forward to the robot so its workspace or field-of-view is 1054 looking forward to collect information forward of the third robot Unit.

In all these preferred embodiments, the robot plays a dual role. It places the tools of the art at the area of the procedure. Also it is a mechanical link for spatially co-registering the information collected by the robot-mounted sensors and the primary guiding modality. During co-registration the robot is substantially registered to the primary guiding modality or the laboratory coordinate frame. Also each position at which data are collected by the robot-mounted sensors is recorded. This position is then translated to the laboratory coordinate frame by means of the kinematic structure, i.e., forward kinematics, of the robotic manipulator In yet another preferred embodiment there is provided means for image-based control of the robot and real-time tracking of tissue. The control logic is configured to precisely follow a moving trajectory that is updated on-the-fly and to control the amount of force exerted during this maneuvering. This is enabled by utilizing an impedance control strategy and integrating it with a visuo haptic human-machine interface.

For example the end-effector may be controlled to reach and hold a position in the center of the aortic annulus for deploying a prosthetic valve. Such maneuvering entails three types of spatial and temporal constraints. Kinematic constraints are imposed by the specific design of the robot, that is, the robot behaves like a constrained under-actuated and hyper-redundant dynamic system (3) Dynamic constraints on the motion envelope of the device are imposed by the dynamic AoP which is parameterized in the form of dynamic access corridors and guidance trajectories. Time constraints may arise from computational delays from the MR and US data processing routines. These must be considered to avoid over-compensation and delay instabilities. These constraints, together with the required task space and range of motion, are incorporated in the control algorithms.

Moreover, for the control logic, adaptive control schemes are implemented to reach zero steady-state error, which leads to tracking of the moving target with a minimum error, and to compensate for flexing due to forces from the moving blood in the LV. This is accomplished in a linear-parameter-varying (LPV) framework as a systematic control design method for dealing with systems with highly nonlinear dynamic behavior (4-5). A parameterized environment model is obtained in the form of dynamic trajectories and dynamic access corridors from MR and US data. With multi-thread processing any computational delays in the feedback loop can be considered and quantified. In this adaptive control scheme, the gains are adapted using a gain-scheduling LPV approach. The controllers are 1) model-based, 2) anti-windup, i.e., there are spatial limits on the distal tip position, 3) provide zero steady-state error, i.e., minimum error when tracking the trajectory and 4) compensate for external forces.

For the robot linearized models are constructed from the state-space structure: $\dot{q}(t)=A(\rho(t))q(t)+B(\rho(t))u(t-\tau_u(t))+D(\rho(t))w(t)$, where $q(t)$ is the configuration space (joint positions and velocities), $u(t-\tau_u(t))$ is the delayed torque input, $w(t)$ any unknown disturbance torques, $\rho(t)$ the parameterized trajectory and $\tau_u(t)$ the variable input delay. The adaptive controller then provides a torque feedback $u(t)=F(\rho(t))q(t)$ to minimize the tracking error. For this system, stability despite variable delays, can be guaranteed through the use of a parameter-dependent Lyapunov functional of the form $$V(x, t) = x^T(t)P(\rho(t))x(t) + \int_{t-\tau_u}^{t} x^T(\xi)Qx(\xi)d\xi.$$

The sampled-data implementation of the control law in the variable sampling rate case is as described previously (6-7). To achieve safety, the constraint imposed by the dynamic corridors is incorporated in the task space and range of motion constraints by appropriate definitions as a set of inequality constraints.

Figure 35:
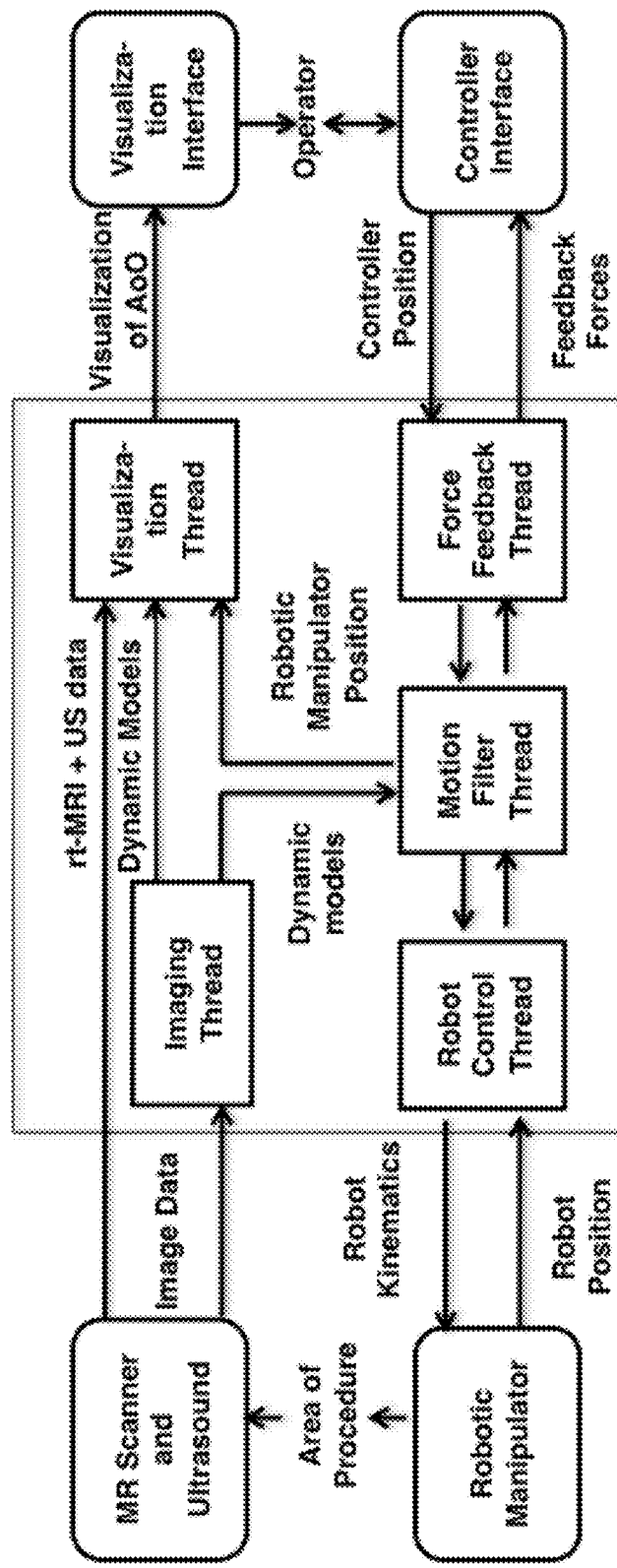
FIG. 35 depicts the data processing and control software core architecture.

A general architecture for the data processing and control software core is depicted in FIG. 35. The core comprises various threads which are linked to a controller interface and to a visualization interface, both of which can be under operator control. The controller interface interfaces with a force feedback thread, a motion filter thread and a robot control thread which directly or indirectly interact with and control the robotic manipulator and monitor its position. The robotic manipulator links positions the end-effector at the area of procedure for MRI and ultra sound procedures. The MR and US units transmit image data to the imaging thread and visualization thread and subsequently to the visualization interface and operator. The imaging thread also transmits the received data as dynamic models to the motion filter thread which sends the robotic manipulator position to the visualization thread to be incorporated with the imaging data.

Figure 36A:
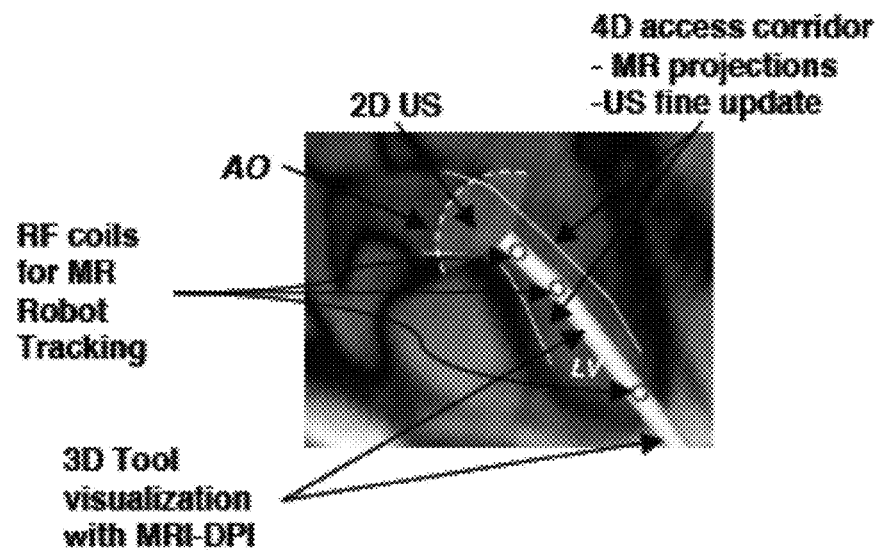
FIGS. 36A-36D are examples of robot control and data collection in real-time.
Figure 36B:
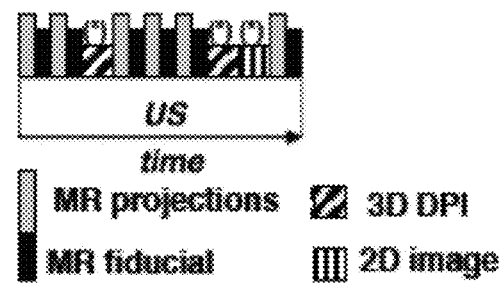
Figure 36C:
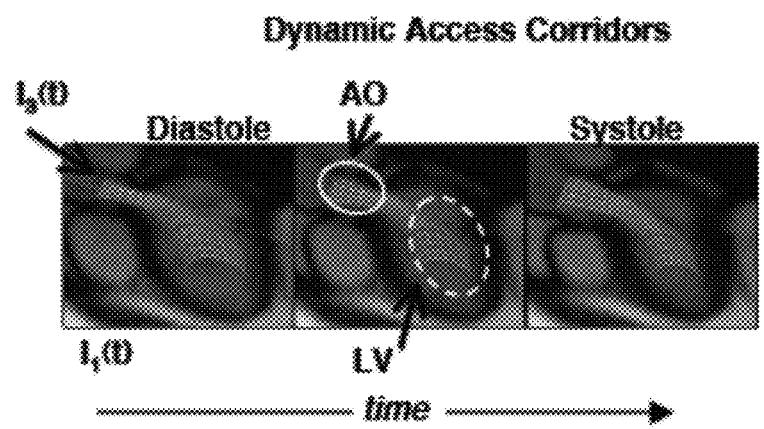
Figure 36D:
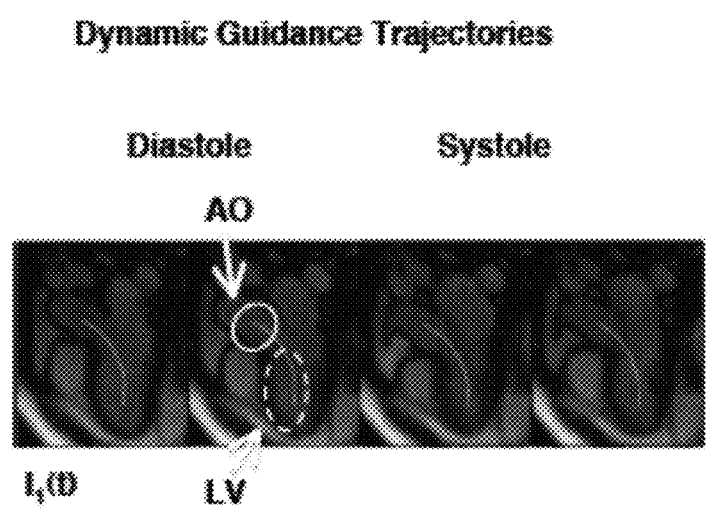

For example, as shown in FIG. 36A, automated or semi-automated control of the robot is based on the assessment of the area of surgery using a combination of magnetic resonance imaging and ultrasound data collected in real-time. Moreover, magnetic resonance and ultrasound methods can be interleaved during the procedure. Also, as shown in FIG. 36B, MR projections, MR 3D DPI, MR fiducial coils, MR 2D imaging and ultrasound can be interleaved where MR 3D DPI and MR 2D imaging are started by the operator. In addition, as shown in FIGS. 36C-36D the processing and control core of the robot incorporates a dedicated thread that generates dynamic virtual fixtures (DVF) on-the-fly from MR and ultrasound real-time data. These fixtures are used by the robot control and by the human-interface threads. The DVF can be one or both of a forbidden region or of guidance.

Figure 37A:
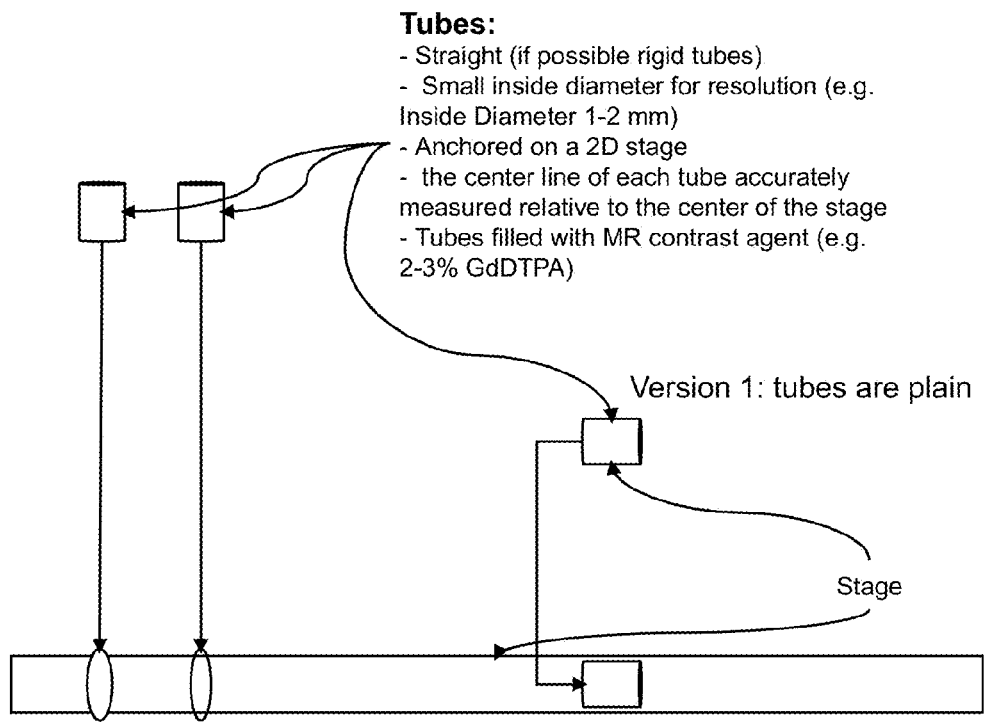
FIGS. 37A-37G: Robot registration to the MRI scanner coordinate system.
Figure 37B:
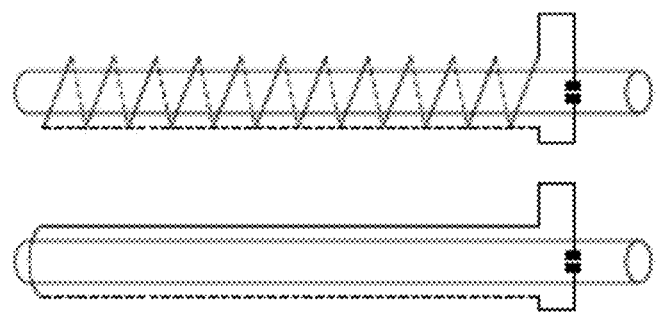

In addition, two methods for rapid automated or semiautomated or manual registration of the robot to the MRI scanner coordinate system are shown in FIGS. 37A-37G. According to this embodiment, straight tubes are embedded or anchored at known positions onto the stage and, as shown in FIG. 37A, are preferentially orthogonal to each other and along the edges of the stage. The particular edge of the stage is identifiable by the number of tubes along this stage, for example, two parallel tubes. Also, as shown in FIG. 37B, the tubes may be surrounded by an inductively coupled RF coil tuned to the particular frequency of operation for the MR scanner to be used with low flip angle imaging methods to better suppress the signal of the background tissue during registration and to eliminate the signal of the marker (tube) during standard imaging.

Figure 37C:
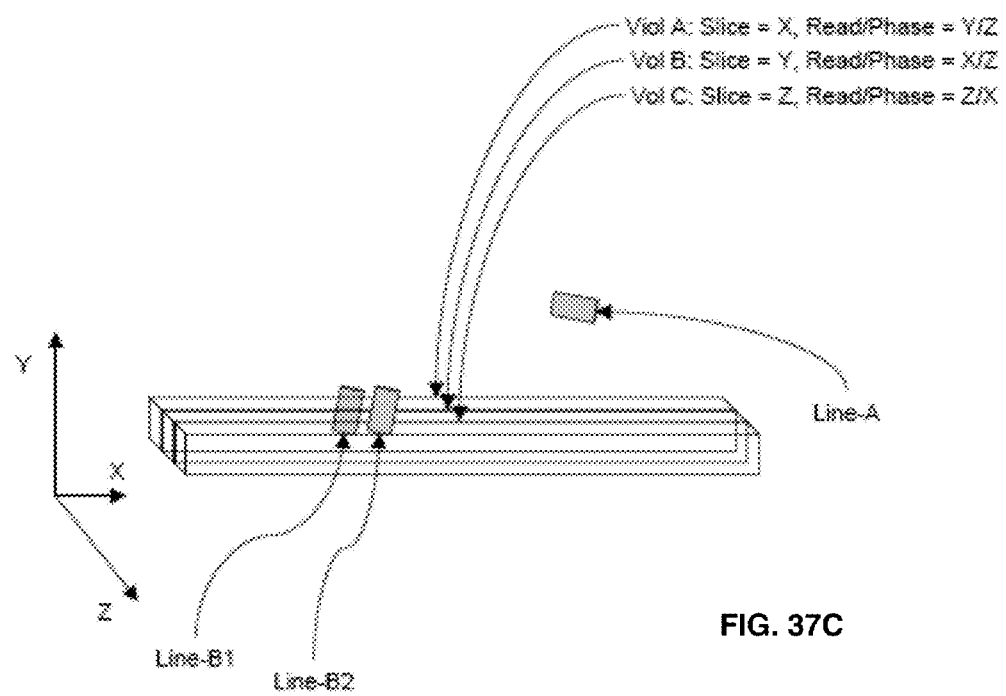
Figure 37D:
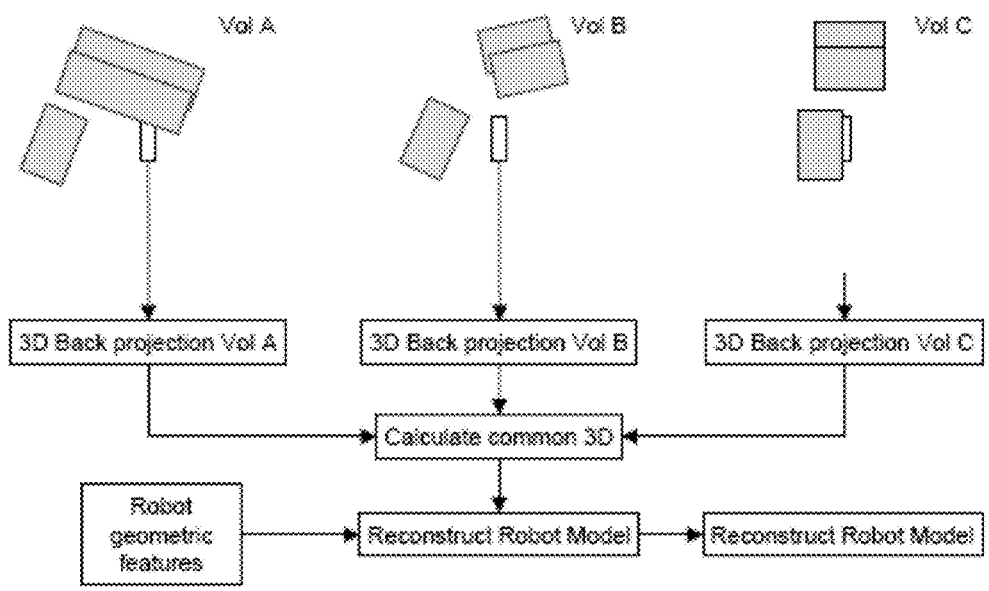
Figures 37E, 37F:
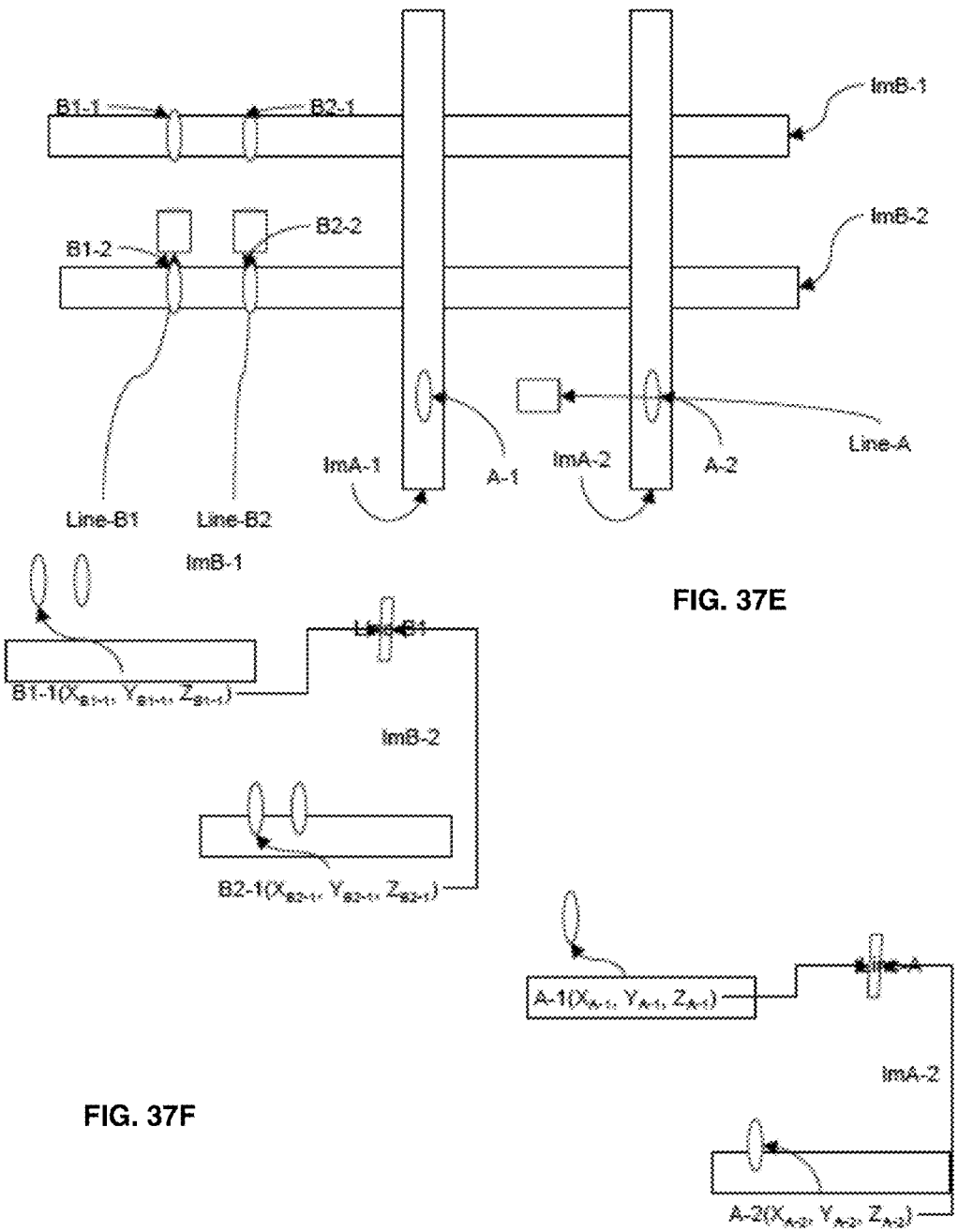
Figure 37G:
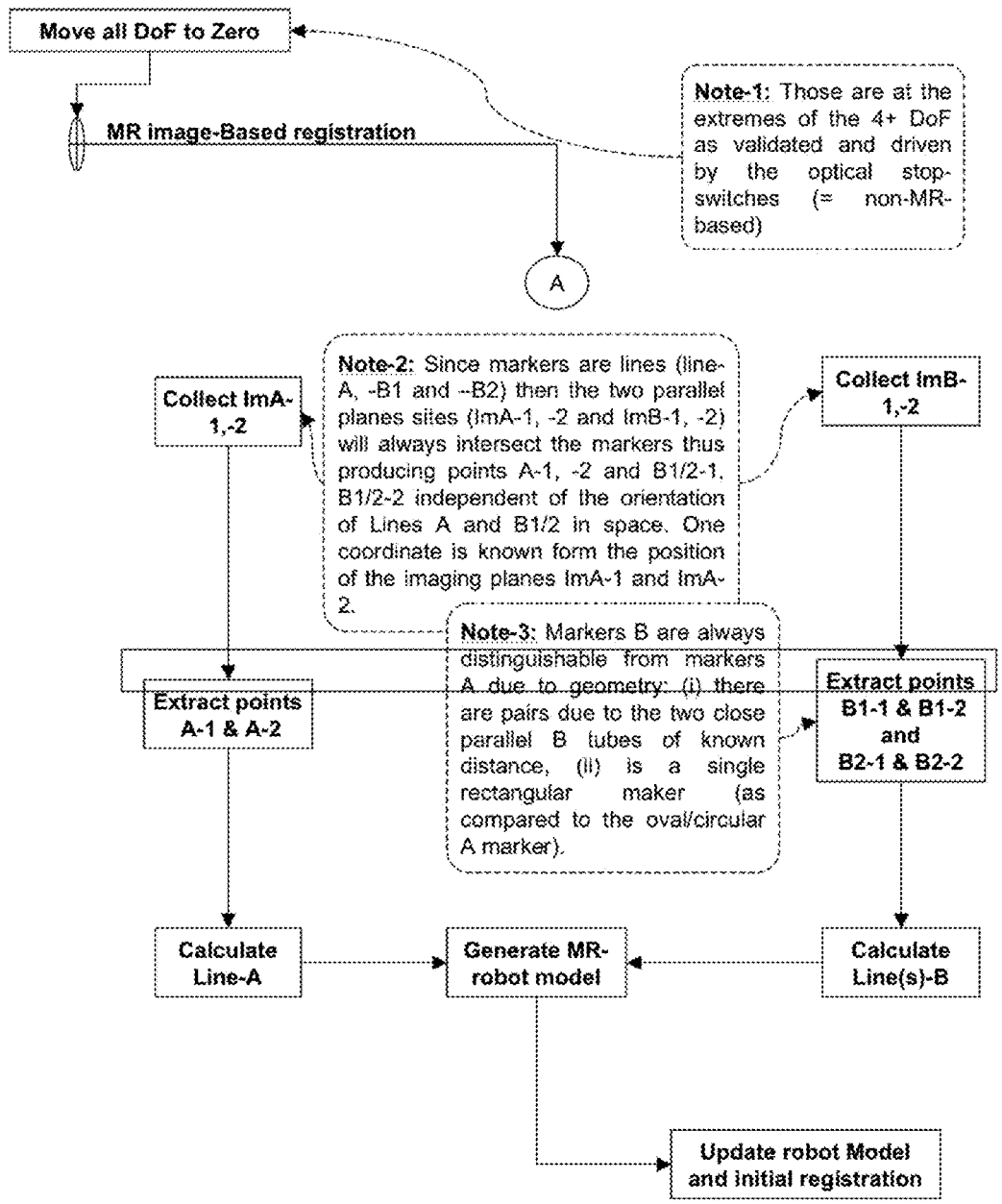

Registration is then performed, as shown In FIGS. 37C-37D, by the collection of three projections over large volumes A, B, C to include the tubes and along the three axes of the MR scanner (X, Y, Z) and reconstructing the tubes in 3D with algorithms, such as but not limited to back-projection algorithms. Alternatively, as shown in FIGS. 37D-37G, imaging planes, particularly, four imaging planes shown in FIG. 37D, are used to image the tubes and to reconstruct them in 3D. With either method, the robot is registered to the MR scanner. Additionally, to know the initial position of the interventional tool, the robot can have another tube along the direction of the interventional tool. Before registration the stage is brought at a pre-selected resting position, such as, but not limited to, the end of the DoF as validated by optical stop switches and/or position encoders.

According to this invention, the rigid-fluid actuation mechanism can be used for any application beyond the one described above, i.e. for medical robotic actuation, when specific conditions require the remote placement of the actuators. As example but not limited to, such actuation can be used at hazardous conditions for the operation of the actuator or when high electromagnetic interference is present, or any other reasons.

The following references are cited herein.
1. U.S. Publication No. 2010/0264918.
2. Bergeles et al., IEEE International Conference on Robotics and Automation (ICRA), pp. 690-695 (2013).
3. Veeramani et al. Smart Materials and Structures, 17:15037 (2008).
4. Mohammadpour, J. and Grigoriadis, K., Proc. AIAA Guidance, Navigation and Control Conference, Honolulu, Hi. (2008).
5. Rugh, W. and Shamma, J., (2000). Automatica, 36:1401-1425 (2002).
6. Tan, K. and Grigoriadis, K., Mathematical Problems in Engineering, 6:145-170 (2000).
7. Tan, K. and Grigoriadis, K., Proc. IEEE Conference on Decision and Control, pp. 4422-4427 (2000).

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

What is claimed is:

1. A robotic system for performing a robot-assisted procedure including diagnostic sensing, injection, ablation, aspiration, biopsy or a surgical procedure, comprising:
at least one instrument for performing the procedure;
at least one image-guided robotic manipulator device;
at least one flexible transmission tubing for actuating the robotic manipulator device which is mechanically linked thereto, and wherein said tubing contains within it several members having rounded surfaces which are aligned along the tubing adjacent one another and members are capable of moving apart from an adjacent member where a force is applied to a particular member in a direction away from said adjacent member;
at least one adjustable base mechanically linked to the robotic manipulator device, wherein said base or said robotic manipulator device can be oriented to an area where the procedure is performed;
at least one sensor configured to send and receive signals from an imaging system such that, following processing in at least one microprocessor, the robot manipulator device can guide the positioning of the base or positioning or manipulation of the instrument; and
wherein said microprocessor acts with software to interface with the imaging system, the robot manipulator device and the manipulation of the instrument so as to make the robotic system capable of performing the procedure.

2. The robotic system of claim 1, wherein said members are spherical in shape.

3. The robotic system of claim 1, wherein at least some of said members are separated from one another by spacers.

4. The robotic system of claim 3, wherein the spacers are rings or washers.

5. The robotic system of claim 3 wherein the spacers are rings or washers or are integral with the spheres.

6. The robotic system of claim 1, wherein the flexible transmission tubing has at least one bend in it.

7. The robotic system of claim 1, further including two or more stages movable with multiple degrees of freedom, disposed in a parallel relationship and mechanically linked and each stage contains at least one degree of freedom to orient the instrument.

8. The robotic system of claim 1, wherein the robotic manipulator device comprises:
at least one first unit configured for global positioning;
at least one second unit, one of said second units movably linked to the first unit;
at least one third unit comprising one or more surgical devices or modalities, one of said third units movably linked to one of the second units and deployable into a body via the second unit; and
a plurality of interfaces in electronic communication with the first, second or third units or a combination thereof and the computer, each of said units independently or in combination configured for co-registration thereof over the interface.

9. The robotic system of claim 8, further comprising one or more imaging or non-imaging sensors internally or externally disposed in relationship to a patient's body, said sensors registrable with the first, second or third units or a combination thereof.

10. The robotic system of claim 9, wherein the second unit, the third unit or both of the robotic manipulator device further comprises a rotating element rotatably linked to the one or more sensors.

11. The robotic system of claim 1, wherein the robotic manipulator device is image-guided during the surgery via registration with an imaging system coordinate system.

12. The robotic system of claim 11, wherein the imaging system comprises magnetic resonance imaging or spectroscopy or a combination thereof, ultrasound imaging, x-ray computed tomography, x-ray mammography, optical imaging, or video.

13. The robotic system of claim 1, wherein the robotic manipulator device further includes:
an actuation power source mechanically connected to the flexible transmission tubing and electronically connected to a robot control module comprising the microprocessor or to a manually controlled robot controller.

14. The robotic system of claim 1, wherein the flexible transmission tubing contains
a linearly translatable first plug-like component disposed at one or both ends of the flexible tubing, said plug in mechanical communication with the members having rounded surfaces such that a force moving the plug towards said members is transmitted through the members to the robotic manipulator device or to the base.

15. The robotic system of claim 1, wherein the flexible transmission tubing further comprises:
one or more openings disposed along the length thereof; and
a plug-like link positioned between two adjacent members and extending through the opening; or
a structure external to the flexible tubing movably engaged with one or more members through the opening.

16. The robotic system of claim 1, wherein the flexible transmission tubing further comprises:
an internal lubricating sleeve disposed between an inner surface of the flexible tubing and the members.

17. The robotic system of claim 13, wherein the flexible transmission tubing is further connected with a straight section of tubing containing one or more rigid pistons having bushings attached around their outer surface, where the pistons are linearly disposed in the straight tubing sections, said straight tubing sections in mechanical communication with the actuation power source such that actuation thereof is transmitted through the rigid pistons to the robotic manipulator device or to the base.

18. The robotic system of claim 1, wherein said members are spheres having diameters of not less than one-half of the inner diameter of the tubing.

19. The robotic system of claim 1, further including an external stiffening sleeve disposed around an outer surface of the flexible transmission tubing and extending partially or completely along the length thereof.

20. The robotic system of claim 1, wherein the microprocessor tangibly stores in memory software modules having processor-executable instructions to:
establish a plurality of interfaces among at least the robotic manipulator, an imaging modality to guide and operate the robotic manipulator, a plurality of imaging or non-imaging sensors to collect data about a condition of a tissue at an area of the procedure, a plurality of sensors to collect data about the robotic manipulator and to measure a motion of one or more degrees of freedom, and an operator of the system;
receive data collected from the imaging modality and the plurality of sensors and generate in real-time a model of the area of the procedure and, if needed, process the data;

generate and regulate type and timing of data collection and communicate instructions about the same to the data collection imaging or non-imaging sensors; and generate static or dynamic paths and trajectories for the robotic manipulator effective to avoid or resolve collisions and to accurately reach the tissue;

generate instructions for the control of the robotic manipulator and communicate the same to a robot control module;

send force and visual feedback to the operator; and receive commands from the operator.

21. A method for performing a robot-assisted surgical procedure under image guidance in real time on a patient, comprising the steps of:

positioning the robotic system of claim 1 proximate to the patient;

adjusting orientation and position of the base or the robotic manipulator device;

imaging the patient via the imaging system;

guiding in real time the base or the robotic manipulator to an area of the procedure on the patient via information electronically obtained by the imaging system; and performing the procedure on the patient via the image-guided robotic manipulator.

22. The method of claim 21, wherein positioning of the robotic manipulator is computer controlled or controlled manually by an operator.

23. The method of claim 21, wherein the imaging step comprises:

co-registering the robotic manipulator with the imaging system prior to the guiding step.

24. The method of claim 21, wherein the performing step comprises:

deploying the instrument registered with the robotic manipulator to the patient.

25. The robotic system of claim 1, wherein the flexible transmission tubing contains air, liquid or displaceable medium.

26. The robotic system of claim 1, wherein the imaging system is magnetic resonance, said robotic system housed within an MRI chamber.

27. The robotic system of claim 1 wherein the imaging system receives signals from contrast markers that are disposed on or around the robotic manipulator device so as to register said robotic manipulator device.

* * * * *